US009017956B2

(12) United States Patent
Bahn et al.

(10) Patent No.: US 9,017,956 B2
(45) Date of Patent: Apr. 28, 2015

(54) USE OF THE GENES IN THE HOG, RAS AND CAMP PATHWAY FOR TREATMENT OF FUNGAL INFECTION

(71) Applicant: Nutrex Technology Co., Ltd., Seoul (KR)

(72) Inventors: Yong-Sun Bahn, Seoul (KR); Young-Joon Ko, Seoul (KR); Shin-Ae Maeng, Seoul (KR); Kwang Woo Jung, Seoul (KR); Gyu Bum Kim, Gyeonggi-do (KR)

(73) Assignee: Nutrex Technology Co., Ltd., Seoul (KR)

( * ) Notice: Subject to any disclaimer, the term of this patent is extended or adjusted under 35 U.S.C. 154(b) by 0 days.

(21) Appl. No.: 13/862,666

(22) Filed: Apr. 15, 2013

(65) Prior Publication Data

US 2013/0237446 A1 Sep. 12, 2013

Related U.S. Application Data

(63) Continuation of application No. 13/143,921, filed as application No. PCT/KR2010/000137 on Jan. 8, 2010, now abandoned.

(30) Foreign Application Priority Data

Jan. 9, 2009 (KR) ........................ 10-2009-0001947
Dec. 18, 2009 (KR) ........................ 10-2009-0127206

(51) Int. Cl.

| | |
|---|---|
| ***C12Q 1/00*** | (2006.01) |
| ***A61K 38/00*** | (2006.01) |
| ***C08F 210/18*** | (2006.01) |
| ***A61K 8/63*** | (2006.01) |
| ***C12Q 1/48*** | (2006.01) |
| ***C07K 14/37*** | (2006.01) |
| ***C12Q 1/18*** | (2006.01) |
| ***C12N 15/10*** | (2006.01) |

(52) U.S. Cl.

CPC ................ *C12Q 1/485* (2013.01); *C07K 14/37* (2013.01); *C12Q 1/18* (2013.01); *G01N 2333/37* (2013.01); *C12N 15/1072* (2013.01)

(58) Field of Classification Search

None

See application file for complete search history.

(56) References Cited

U.S. PATENT DOCUMENTS 5,444,052 A * 8/1995 Pieringer et al. ................ 514/31
6,660,761 B2 * 12/2003 Khanuja et al. ............... 514/396
2006/0293381 A1 12/2006 Kojima et al.

OTHER PUBLICATIONS

Kontoyiannis et al. 2008 (Calcineurin Inhibitor Agents Interact Synergistically with Antifungal Agents In Vitro Against *Cryptococcus neoformans* Isolates: Correlation with Outcome in Solid Organ Transplant Recipients with Cryptococcosis; Antimicrobial Agents and Chemotherapy, 52(2):735).*

Bahn et al. 2006 (A Unique Fungal Two-Component System Regulates Stress Responses, Drug Sensitivity, Sexual Development, and Virulence of *Cryptococcus neoformans*; Molecular Biology of the Cell 17:3122-3135).*

Bahn et al. 2007 (Sensing the environment: lessons from fungi; Nature Reviews Microbiology 5:57-69).*

Bahn et al. (2006) Molecular Biology of the Cell 17:3122-3135 "A Unique Fungal Two-Component System Regulates Stress Responses, Drug Sensitivity, Sexual Development, and Virulence of *Cryptococcus neoformans*".

International Search Report for PCT/KR2010/000137 mailed Sep. 13, 2010, 3 pages.

Kojima et al. (2006) Microbiology 152:591-604 "Calcineurin, Mpk1 and Hog1 MAPK pathways independently control fludioxonil antifungal sensitivity in *Cryptococcus neoformans*".

Kontoyiannis et al. (2008) Antimicrobial Agents and Chemotherapy 52(2):735-738 "Calcineurin Inhibitor Agents Interact Synergistically with Antifungal Agents In Vitro against *Cryptococcus neoformans* Isolates: Correlation with Outcome in Solid Organ Transplant Recipients with Cryptococcosis".

* cited by examiner

*Primary Examiner* — J. Hines
*Assistant Examiner* — Mary Lyons
(74) *Attorney, Agent, or Firm* — Swanson & Bratschun, L.L.C.

(57) ABSTRACT

Provided herein are uses of genes for HOG, Ras and cAMP signal transduction pathways to treat fungal infection. To regulate the HOG pathway of *Cryptococcus neoformans*, roles of SSK1, TCO2, SSK2, PBS2, HOG1, ENA1 and NHA1 genes were investigated to find that a biosynthesis level of ergosterol is increased when these genes are inhibited. When the genes are inhibited, a large amount of ergosterol is distributed on a fungal cell membrane. Accordingly, since there are many working points of an ergosterol-binding antifungal agent, an efficiency of the ergosterol-binding antifungal agent can be considerably improved. To regulate the Ras and cAMP pathways of *Cryptococcus neoformans*, roles of RAS1, RAS2, CDC24, GPA1, CAC1, ACA1, PKA1, HSP12 and HSP122 genes were investigated to find that a sensitivity to a polyene- or azole-based drug is increased when these genes are inhibited. Therefore, an antifungal pharmaceutical composition including an inhibitor against the gene or protein encoded by the same can be used as an excellent combined antifungal agent which can reduce a conventional amount of an antifungal agent used and increase an efficiency.

4 Claims, 10 Drawing Sheets

USE OF THE GENES IN THE HOG, RAS AND CAMP PATHWAY FOR TREATMENT OF FUNGAL INFECTION

CROSS-REFERENCE TO RELATED APPLICATION

This application is a continuation of pending U.S. patent application Ser. No. 13/143,921, filed on Sep. 9, 2011, entitled "Use of the Genes in the Hog, Ras and cAMP Pathway for Treatment Of Fungal Infection," which application is a 35 U.S.C. §371 national phase application of PCT/KR2010/000137, filed on Jan. 8, 2010, which application claims priority to and the benefit of Korean Patent Applications No. 10-2009-0001947, filed on Jan. 9, 2009, and No. 10-2009-0127206, filed on Dec. 18, 2009, each of which are incorporated herein by reference in their entirety.

SEQUENCE LISTING

Incorporated by reference herein in its entirety is the Sequence Listing entitled "Sequence Listing," created Apr. 10, 2013, size of 167 kilobytes.

BACKGROUND

1. Field

The present invention relates to uses of genes for HOG, Ras and cAMP signal transduction pathways to treat fungal infection.

2. Description of the Related Art

The existence and proliferation of an organism in a specific environment is usually determined by an ability to react and adapt to various environmental stresses and maintain cell homeosis. Cells regulate a key process by performing a series of combined signal networks. Among these, a p38/Hog1 mitogen-activated protein kinase (MAPK) dependent signal pathway plays an important role to regulate a wide range of stress reactions in eukaryotes, for example, from yeasts to humans.

A stress-activated p38 MAPK in a mammal induces various stress-related signals limiting change in osmosis, UV radiation, programmed apoptosis, and adaptation to an immune response by generation of cytokine and control of inflammation. Similar stress-sensitive signal transduction systems have been discovered in other species. Fungi have p38-like MAPKs regulating various stress-related responses. In the budding yeast, *Saccharomyces cerevisiae* (*S. cerevisiae*), HogI MAPK regulates a stress-related response to osmotic shock, oxidative damage and heavy metal damage. The fission yeast, *Schizosaccharomyces pombe* (*S. pombe*), also has a homolog of HogI, Sty1 (also known as Spc1 and Phh1), which is associated with adaptation to various stresses including osmotic shock, heat shock, oxidative damage and heavy metal damage, carbon deficiency and UV radiation. Interestingly, StyI is also associated with growth control, reproduction and differentiation. Hog1 MAPK orthologs are also found in other ascomycete pathogenic fungi including *Candida albicans* (Hog1) and *Aspergillus fumigatus* (SakA), and known to mediate reactions induced by various environmental causes including osmotic shock, UV radiation, oxidative damage and high temperature.

A common molecular mechanism of the p38/HogI MAPK signal transduction network is highly conserved in many eukaryotic cells. While the p38/Hog1 MAPK is non-phosphorylated under normal growth conditions, it is activated by double phosphorylation of Thr and Tyr residues at a TGY motif using a MAPK kinase (MAPKK) activated through phosphorylation by a MAPKK kinase (MAPKKK) in a higher signal system in response to a specific environmental stress. Subsequently, the phosphorylated p38/Hog1 MAPKs are transferred to a nucleus after a dimer is formed to trigger activation of a transcription regulatory factor and induce overproduction of stress-preventing genes resistant to external stress conditions.

In spite of the conserved regulatory mechanism of the p38/Hog1 MAPK, fungi and mammals have developed a distinctive set of a higher regulatory systems. Particularly, fungi use a two-component-like phosphorelay system, which is not present in mammals, but found only in bacteria, fungi and plants. The fungal phosphorelay system is composed of three components including a hybrid sensor kinase, histidine-containing phosphotransfer protein (HPt), and a response regulator. The three components have not been observed in mammals, and thus are considered a good target for an antifungal agent.

Basidiomycetous, *Cryptococcus neoformans* (*C. neoformans*), also uses a stress-activated Hog1 MAPK system to adapt to various environmental stresses including osmotic shock, UV radiation, heat shock, oxidative damage, toxic metabolites and antifungal agents. *C. neoformans* is a human pathogenic fungus found everywhere in the world, causing cryptococcal disease in the skin and lungs and cryptococcal encephalomeningitis in immunocompromised patients. While *C. neoformans* var. *grubii* (antigen-type A) is the most frequently found (>90% of environmental and clinical strains), *C. neoformans* var. *neoformans* (antigen-type D) is common only in a specific region in Europe, but not frequently found (<10%). However, it has been confirmed that *C. gattii*, known as *C. neoformans* of antigen-types B and C, are primary pathogens attacking normal people who have no immune problems.

However, it is inferred that, compared with other fungal Hog1 MAPK systems, the Hog1 MAPK pathway in *C. neoformans* is not characteristically developed only to correspond to various environmental stresses, but also to regulate production of two pathogenic factors such as an antiphagocytic capsule and an antioxidant melanine and sexual differentiation, and thus plays a critical role as an important signal transduction regulator in *C. neoformans* cross-talking to another signal transduction pathway. Recently, the inventors found that most Hog1 MAPKs in many *C. neoformans* strains are always phosphorylated under non-stress conditions, and rapidly dephosphorylated to activate the Hog1 MAPKs in response to the osmotic shock and treatment of an antifungal agent, fludioxonyl, which clearly contrasts with Hog1 MAPK systems in other fungi. Double phosphorylation at the TGY motif of Hog1 needs Pbs2 MAPKK. A fungus-specific phosphorelay system which is in a higher level of a Pbs2-Hog1 pathway is also found only in *C. neoformans*. The *C. neoformans* phosphorelay system includes 7 different sensor hybrid histidine kinases (TcoI-7), a Ypd1 phosphotransfer protein, and two reaction regulators (Ssk1 and Skn7). The Pbs2-Hog1 pathway is generally regulated by Ssk1, not by Skn7. Among the 7 Tco proteins, Tco1 and Tco2 play distinctive and overlapping roles to activate the Ssk1 and the Pbs2-Hog1 MAPK pathway. However, the Tco1 and Tco2 regulate some Ssk1 and Hog1-related phenotypes, and therefore other higher receptor or sensor proteins should be discovered. More recently, a protein, Ssk2 MAPKKK, serving as a linker between the phosphorelay system and the Pbs2-Hog1 MAPK pathway was identified by comparative analysis of a meiotic map between antigen-type D f1 brother strains, B3510 and B3502, showing different phosphorylation patterns of Hog1.

The most noticeable fact is that interchange of Ssk2 alleles between two *C. neoformans* strains showing different Hog1 phosphorylation patterns changes a phenotype controlled by constitutive Hog1 phosphorylation. Unlike *S. cerevisiae* and *S. pombe, C. neoformans* has single MAPKKK and Ssk2 regulating the Hog1 MAPK. While a downstream signal transduction network of the Hog1 MAPK pathway in *C. neoformans* has yet to be discovered, identification and characterization of the downstream signal transduction network of the Hog1 MAPK are needed to develop a target for a new antifungal agent.

In the past, fungal infections were mainly local infections such as athlete's foot, jock itch, or oral thrush, and rarely systemic infections. However, recently, systemic infections have become as frequent, coming in fourth in frequency among total infections occurring in hospitals.

The antifungal agents which have been developed so far may be classified into two major groups: those having an azole structure and those not having an azole structure. The azole-based antifungal agents include ketoconazole, fluconazole, itraconazole and voriconazole, while the non-azole-based antifungal agents include terbinafine, flucytosine, amphotericin B and caspofungin.

The ketoconazole, fluconazole, itraconazole and voriconazole having an azole structure have similar mechanisms to allylamine-based naftifine and terbinafine. These two different antifungal agents serve to inhibit enzymes required for the conversion of lanosterol into ergosterol, which is a main component of a fungal cell membrane. The azole-based antifungal agents inhibit a microsomal enzyme, and the acrylamine-based antifungal agents inhibit a squalene epoxidase, both having a similar effect to the above-mentioned antifungal agents. Flucytocin (5-FC) is a metabolic antagonist inhibiting the synthesis of a nucleic acid, which has an antifungal reaction by non-competitively antagonizing the cause of mis-coding a fungal RNA and DNA synthesis. Amphotericin B having a polyene structure has an antifungal reaction by binding to ergosterol in the fungal cell membrane to induce depolarization of the cell membrane and generating a hole to induce loss of the cell contents. An echinocandin-based antifungal agent, caspofungin, has a reaction reversibly inhibiting the formation of a fungal cell wall, and is different from those acting on the cell membrane described above.

The azole-based drug may lead to death caused by infection when being used on a patient having hypofunction of the liver, and thus a liver function test should precede administration. It is reported that flutocytosin has a dose-dependent bone marrow inhibiting action, liver toxicity, and can cause enterocolitis. Since such side effects are increased when renal insufficiency occurs, monitoring of a renal function is very important to a patient. In addition, flutocytosin is contraindicated for pregnant woman. A major toxicity of amphotericin B is a glomerulus renal toxicity induced by renal artery vasoconstriction, which is dose dependent. Therefore, when a lifetime cumulative dose is 4 to 5 g or more, a rate of permanent loss of the renal function is increased. Furthermore, the renal toxicities such as excessive loss of potassium, magnesium and bicarbonate due to toxicity of a renal tube and low production of erithropoietins may be generated. Moreover, as acute responses, symptoms such as thrombophlebitis, chills, shivering, and hyperpnea may be shown. Since the conventionally developed antifungal agents show various side effects according to kinds of drugs, development of a new therapy which can reduce such side effects and increase an antifungal effect is demanded.

Meanwhile, in pathogenic fungi distributed in the world, including *Aspergillus fumigatus, Candida albicans* (*C. albicans*) and *C. neoformans*, Ras- and cAMP-signal transduction pathways are evolutionarily conserved, and significantly functional and structural differences are still being found (Pukkila-Worley & Alspaugh, 2004, Rolland et al., 2002, Wong & Heitman, 1999, Thevelein & de Winde, 1999, Alspaugh et al., 1998, Lengeler et al., 2000, and Bahn et al., 2007). In *C. neoformans* causing fatal fungal encephalomeningitis, the cAMP-signal transduction pathway is important in producing and differentiating pathogenic factors (Idnurm et al., 2005). Like *S. cerevisiae* and *C. albicans*, it was confirmed that two major higher signal transduction regulators of adenylyl cyclase (Cac1), adenylyl cyclase-associated protein 1 (Aca1) and Gα subunit protein (Gpa1) regulate a cAMP-signal transduction pathway of *C. neoformans* (Bahn et al., 2004 and Alspaugh et al., 1997). The disruption of GPA1 genes leads to multiple phenotypes of cells, which include incomplete production of core pathogenic factors, melanin and a capsule, essential for survival and proliferation of *C. neoformans* in a host, and a decrease in mating, which is important in distribution of infectious spores (Alspaugh et al., 1997). Aca1 physically interacts with a Cac1 adenylyl cyclase, and does not regulate a basic level of cAMP but dominates most cAMP-dependent phenotypes by regulating the induction of cAMP (Bahn et al., 2004). A deletion mutant of CAC1 produces a phenotype more defected than a deletion mutant of gpa1Δ or aca1Δ, and gpa1Δ aca1Δ double deletion mutants are equivalent to the cac1Δ deletion mutant in phenotype (Bahn et al., 2004). This indicates that Cal1 is activated by both of Aca1 and Gpa1. In a lower signal system of the Cac1 of *C. neoformans*, two catalytic subunits of a protein kinase A (PKA), Pka1 and Pka2, and a regulatory subunit, Pkr1, are included. While Pka1 plays a dominant role for cAMP signal transduction in a background of an antigen-type A *C. neoformans* H99 strain, Pka2 also plays the same role in an antigen-type D *C. neoformans* JEC21 strain (Hicks et al., 2004). Nevertheless, a pka1Δ-pka2Δ double deletion mutant shows a phenotype the same as the cac1Δ deletion mutant, and the cAMP signal transduction from Cac1 is split into two PKA catalytic subunits (Bahn et al., 2004). Interestingly, the deletion of PDE1, not PDE2, repairs some phenotypes including the depletion of a melanin of the gpa1Δ deletion mutant, which indicates that different phosphodiesterases act in various fungi (Hicks et al., 2005).

It is revealed that two Ras proteins, Ras1 and Ras2, are found in *Cryptococcus*, and play common and distinctive roles (Alspaugh et al., 2000, D'Souza et al., 2001, and Waugh et al., 2002). Among these proteins, Ras1 is a major *C. neoformans* Ras protein supporting high-temperature growth and invasive growth essential for survival and growth in a host and stimulating sexual differentiation (Alspaugh et al., 2000). Though the ras2Δ deletion mutant does not have a recognizable phenotype, the overexpression of RAS2 somewhat inhibits most of the ras1 mutation phenotypes (Waugh et al., 2002). Like *S. cerevisiae*, disruption of the RAS1 and RAS2 genes affects cell viability at every temperature, which indicates that the Ras protein is essential for the growth of cells in general. Among various Ras-related phenotypes, only invasive growth and mating are cAMP-dependent, but high-temperature growth is cAMP-independent and a Ras1-specific phenotype (Alspaugh et al., 2000, Waugh et al., 2003). Interestingly, Cac1 does not bear a Leucine-rich repeat (LRR) domain, which is a binding site to a GTP-binding Ras in *S. cerevisiae* (Shima et al., 1997). Since an adenylyl cyclase/cyclase-related protein complex can provide a secondary Ras-binding site to activate the protein complex as shown in *S. cerevisiae* (Shima et al., 2000), Ras1 can still interact with an Aca1/Cac1 complex for activating the Ras1 in *C. neofor-*

*mans*. Recently, it has been reported that a GEF protein, Cdc24, is a Ras-effecter protein, and regulates the growth of *C. neoformans* at high temperature in a lower system of Ras1 and a higher system of Rho-like GTPase Cdc42 (Nichols et al., 2007). Consequently, *C. neoformans* cAMP-signal transduction pathway is regulated by three different higher signal regulators, Ras1, Gpa1 and Aca1.

Despite the presence of the common higher signal regulators (Ras1, Aca1 and Gpa1) of Cac1, functional correlation between the components and target gene regulated by each regulator in *C. neoformans* remains still unclear.

SUMMARY

The present invention provides to finding a new target gene to develop an antifungal agent by investigating a signal transduction network of HOG, Ras and cAMP pathways.

In one aspect, a use of an inhibitor against at least one protein or a gene coding for the same selected from the group consisting of Ssk1, Tco2, Ssk2, Pbs2, Hog1, Ena1 and Nha1 of *C. neoformans* to prepare an antifungal agent, an antifungal pharmaceutical composition including the inhibitor, and a method of treating fungal infection including injecting an effective amount of the inhibitor into a subject are provided.

In another aspect, a use of at least one protein or a gene coding for the same selected from the group consisting of Ssk1, Tco2, Ssk2, Pbs2, Hog1, Ena1 and Nha1 of *C. neoformans* to screen an antifungal agent, a composition for screening an antifungal agent including the protein or gene, and a method of screening an antifungal agent including contacting the protein or gene with a candidate material and determining whether the candidate material inhibits or stimulates an activity of the protein or gene are provided.

In still another aspect, a use of an inhibitor against at least one protein or a gene coding for the same selected from the group consisting of Ras1, Ras2, Cdc24, Gpa1, Cac1, Aca1, Pka1, Hsp12 and Hsp122 of *C. neoformans* to prepare an antifungal agent, an antifungal pharmaceutical composition including the inhibitor, and a method of treating fungal infection including injecting an effective amount of the inhibitor into a subject are provided.

In yet another aspect, a use of at least one protein or a gene coding for the same selected from the group consisting of Ras1, Ras2, Cdc24, Gpa1, Cac1, Aca1, Pka1, Hsp12 and Hsp122 of *C. neoformans* to screen an antifungal agent, a composition for screening an antifungal agent including the protein or gene, and a method of screening an antifungal agent including contacting the protein or gene with a candidate material and determining whether the candidate material inhibits or stimulates an activity of the protein or gene are provided.

In the present invention, to regulate a HOG pathway of *C. neoformans*, roles of SSK1, TCO2, SSK2, PBS2, HOG1, ENA1 and NHA1 genes are investigated to reveal that a biosynthesis level of ergosterol is increased when these genes are inhibited. Since a large amount of ergosterol is distributed on a fungal cell membrane when the genes are inhibited, an efficiency of an ergosterol-binding antifungal agent can be considerably increased due to many working points of the ergosterol-binding antifungal agents. In addition, in the present invention, to regulate Ras and cAMP pathways of *C. neoformans*, roles of RAS1, RAS2, CDC24, GPA1, CAC1, ACA1, PKA1, HSP12 and HSP122 genes were investigated to reveal that sensitivity to a polyene- or azole-based drug is increased when these genes are inhibited. Thus, an antifungal pharmaceutical composition including an inhibitor against the gene or protein encoded by the same can be used as an excellent combined antibacterial drug which can reduce an amount of a conventional antifungal agent used and increase efficiency.

BRIEF DESCRIPTION OF THE DRAWINGS

The above and other aspects of the inventive concept will become more readily apparent by describing in further detail exemplary embodiments thereof which reference to the accompanying drawings, in which.

DETAILED DESCRIPTION

Figure 1:
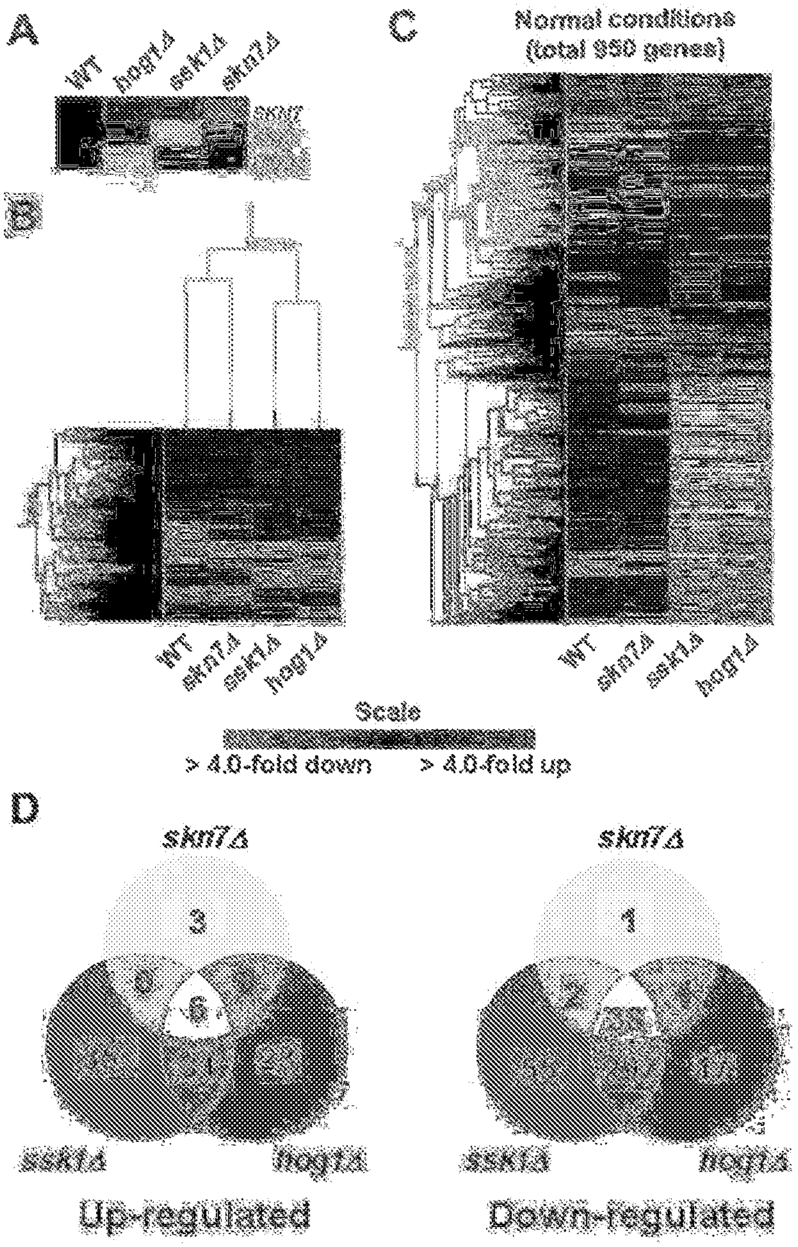
FIG. 1 shows identification of genes whose expression is regulated by Hog, Ssk1 and Skn7 of *C. neoformans* under normal conditions with no stress on the genome level (fold change is expressed by color)

Hereinafter, the present invention will be described in detail.

An antifungal pharmaceutical composition including an inhibitor against at least one protein or gene coding for the same selected from the group consisting of Ssk1, Tco2, Ssk2, Pbs2, Hog1, Ena1 and Nha1 of *C. neoformans* to prepare an antifungal agent is provided.

A HOG1 pathway is a cell signal transduction system regulating responses induced by various stresses. Particularly, since fungi use a two-element-like phosphorelay system composed of three elements such as a hybrid sensor kinase, a histidine-containing phosphotransfer protein (HPt) and a response regulator, which are not present in mammals, the inventors carried on an investigation of roles of genes involved in the HOG1 pathway to develop a target for a new antifungal agent. As a result, surprisingly, it was found that, in the regulation of the HOG pathway in *C. neoformans*, a biosynthesis level of ergosterol is increased when SSK1, TCO2, SSK2, PBS2, and HOG1 genes are inhibited. As will be confirmed in the following embodiments, when the genes are inhibited, a large amount of ergosterol is distributed on a fungal cell membrane and working points of the ergosterol-binding antifungal agent are also increased. Therefore, an efficiency of the ergosterol-binding antifungal agent can be considerably increased. In addition, when ENA1 and NHA1 genes, the expression of which is known to be regulated by the HOG signal transduction pathway, are inhibited, it is confirmed that, regardless of the change in ergosterol level, a sensitivity to polyene-based drugs such as amphotericin B and azole-based drugs are considerably increased. Thus, the antifungal pharmaceutical composition including an inhibitor against at least one protein selected from the group consisting of Ssk1, Tco2, Ssk2, Pbs2, Hog1, Ena1 and Nha1 of *C. neoformans* may be used as an excellent combined antibacterial drug which can reduce an amount of the conventional ergosterol-binding antifungal agent or azole-based antifungal agent used and increase efficiency.

Accordingly, a use of an inhibitor against at least one protein or gene coding for the same selected from the group consisting of Ssk1, Tco2, Ssk2, Pbs2, Hog1, Ena1 and Nha1 of *C. neoformans* to prepare an antifungal agent, an antifungal pharmaceutical composition including the inhibitor, and a method of treating fungal infection including injecting an effective amount of the inhibitor to a subject are provided.

In the specification, it is understood that SSK1, TCO2, SSK2, PBS2, HOG1, ENA1 or NHA1 used as a target to interrupt a HOG1 signal transduction system indicates an Ssk1, Tco2, Ssk2, Pbs2, Hog1, Ena1 or Nha1 protein, or an SSK1, TCO2, SSK2, PBS2, HOG1, ENA1 or NHA1 gene. Thus, it is understood that an SSK1, TCO2, SSK2, PBS2, HOG1, ENA1 or NHA1 inhibitor includes either an inhibitor against an Ssk1, Tco2, Ssk2, Pbs2, Hog1, Ena1 or Nha1 protein or an inhibitor against an SSK1, TCO2, SSK2, PBS2, HOG1, ENA1 or NHA1 gene.

In one exemplary embodiment, the inhibitor against at least one protein selected from the group consisting of Ssk1, Tco2, Ssk2, Pbs2, Hog1, Ena1 and Nha1 of *C. neoformans* may bind to the protein to inhibit an activity thereof, thereby interrupting signal transduction. In another exemplary embodiment, the inhibitor against at least one gene selected from the group consisting of SSK1, TCO2, SSK2, PBS2, HOG1, ENA1 and NHA1 of *C. neoformans* may inhibit expression of the gene to interrupt signal transduction. In the specification, the SSK1, TCO2, SSK2, PBS2, HOG1, ENA1 or NHA1 gene may be a DNA coding for the gene or mRNA transcripted therefrom. Thus, the inhibitor against the gene may bind to the gene itself to disturb transcription or bind to the mRNA transcripted from the gene to disturb translation of the mRNA.

In one exemplary embodiment, the Ssk1, Tco2, Ssk2, Pbs2, Hog1, Ena1 or Nha1 protein may have an amino acid sequence of SEQ ID NOs: 1-7 respectively, and the SSK1, TCO2, SSK2, PBS2, HOG1, ENA1 or NHA1 gene may have a nucleic acid sequence of SEQ ID NOs: 8-14 respectively or a cDNA sequence of SEQ ID NOs:15-21 respectively. However, this is merely an example of a sequence of *C. neoformans* antigen-type A H99 strain, and the sequence of the SSK1, TCO2, SSK2, PBS2, HOG1, ENA1 or NHA1 is not limited thereto.

In the specification, it is understood that the Ssk1, Tco2, Ssk2, Pbs2, Hog1, Ena1 or Nha1 protein or the SSK1, TCO2, SSK2, PBS2, HOG1, ENA1 or NHA1 gene includes a variant or fragment thereof having substantially the same activity as the protein or gene.

In one exemplary embodiment, the antifungal pharmaceutical composition may include at least one inhibitor against at least one protein selected from the group consisting of Ssk1, Ena1 and Nha1. SSK1 may be a good target to develop an antifungal agent because it is not only an important upstream reaction regulator of HOG1, but also a gene which is not found in mammals. Therefore, the SSK1 inhibitor may reduce a possibility of generating certain side effects and increase a biosynthesis level of ergosterol in a fungus, thereby improving the efficiency of an ergosterol-binding antifungal agent. Meanwhile, ENA1 and NHA1 are defined as lower-system target genes regulated by a HOG pathway. When these genes are inhibited, sensitivity to an azole-based drug such as fluconazole, ketoconazole and itraconazole is also considerably increased as well as that to a polyene-based drug such as amphotericin B. Therefore, the inhibitors simultaneously or independently inhibiting these genes may exhibit very high antifungal activities when used in combination with the polyene- or azole-based drug.

The inhibition of the Ssk1, Tco2, Ssk2, Pbs2 or Hog1 protein or gene improves the biosynthesis of ergosterol and increases the distribution of ergosterol on a fungal cell membrane. Thus, since binding targets of the ergosterol-binding antifungal agent disrupting the fungal cell membrane by being bound to ergosterol are increased, an effective amount of the ergosterol-binding antifungal agent may be reduced and a killing ability of the ergosterol-binding antifungal agent may be increased. In addition, the inhibitors against ENA1 and NHA1 considerably increase drug sensitivities to the azole-based antifungal agent as well as the polyene-based antifungal agent, and thus amounts of these drugs used can be reduced and a killing ability may be improved. Such an antifungal activity induced by the inhibition of SSK1, TCO2, SSK2, PBS2, HOG1, ENA1 or NHA1 may treat cryptococcal disease and encephalomeningitis by infection of *C. neoformans*.

Thus, in one exemplary embodiment, use of an Ssk1, Tco2, Ssk2, Pbs2, Hog1, Ena1 or Nha1 inhibitor to prepare a drug for treating a disease such as cryptococcal disease or encephalomeningitis, a pharmaceutical composition for treating a disease such as cryptococcal disease or encephalomeningitis including the Ssk1, Tco2, Ssk2, Pbs2, Hog1, Ena1 or Nha1 inhibitor, and a method of treating a disease such as cryptococcal disease or encephalomeningitis including injecting an effective amount of the Ssk1, Tco2, Ssk2, Pbs2, Hog1, Ena1 or Nha1 inhibitor to a subject are provided.

Other than cryptococcal disease or encephalomeningitis exemplified in the specification, diseases induced by fungal infection are well known in the art. In the specification, the inhibition of the Ssk1, Tco2, Ssk2, Pbs2, Hog1 protein or gene is revealed to improve the efficiency of the ergosterol-binding antifungal agent or azole-based antifungal agent, and thus those of ordinary skill in the art may inhibit the protein or gene to prevent or treat a disease induced by fungal infection.

In the specification, the "inhibitor of the Ssk1, Tco2, Ssk2, Pbs2, Hog1, Ena1 or Nha1 protein" used to interrupt a HOG1 signal transduction system includes all inhibitors binding to the Ssk1, Tco2, Ssk2, Pbs2, Hog1, Ena1 or Nha1 protein to interrupt signal transduction. For example, such an inhibitor may be a peptide or compound binding to the Ssk1, Tco2, Ssk2, Pbs2, Hog1, Ena1 or Nha1 protein. Such an inhibitor may be selected by a screening method to be described below in analysis of a protein structure, and may be designed using a known method in the art. In one exemplary embodiment, the inhibitor may be a polyclonal or monoclonal antibody with respect to at least one protein selected from the group consisting of Ssk1, Tco2, Ssk2, Pbs2, Hog1, Ena1 or Nha1 of *C.*

*neoformans*. Such a polyclonal or monoclonal antibody may be prepared using a method of preparing an antibody known in the art.

In the present invention, the "inhibitor against the SSK1, TCO2, SSK2, PBS2, HOG1, ENA1 or NHA1 gene" used to interrupt a HOG1 signal transduction system includes every inhibitor inhibiting the expression of the SSK1, TCO2, SSK2, PBS2, HOG1, ENA1 or NHA1 gene to interrupt signal transduction. For example, such an inhibitor may be a peptide, nucleic acid or compound binding to the gene. The inhibitor may be selected by a screening method shown below in cell-based screening, and may be designed using a known method in the art. In one exemplary embodiment, the inhibitor may be an antisense oligonucleotide, siRNA, shRNA, miRNA or vector including the same with respect to at least one gene selected from the group consisting of SSK1, TCO2, SSK2, PBS2, HOG1, ENA1 and NHA1 of *C. neoformans*. The antisense oligonucleotide, siRNA, shRNA, miRNA or vector including the same may be prepared using a known method in the art. In the specification, the "vector" refers to a gene construct including foreign DNA inserted into a genome coding for a polypeptide. The vector used herein is a vector in which a nucleic acid sequence inhibiting the gene is inserted into a genome, and may include a DNA vector, a plasmid vector, a cosmid vector, a bacteriophage vector, a yeast vector, or a viral vector.

A pharmaceutical antifungal pharmaceutical composition including an inhibitor against at least one protein or gene selected from the group consisting of SSK1, TCO2, SSK2, PBS2, HOG1, ENA1 and NHA1 of *C. neoformans* does not exhibit an antifungal activity alone, but increases a fungal killing ability of an antifungal agent in combination with the ergosterol-binding antifungal agent or azole-based antifungal agent. Therefore, the antifungal pharmaceutical composition may be sequentially or simultaneously injected with the ergosterol-binding antifungal agent or azole-based antifungal agent.

The ergosterol-binding antifungal agent refers to an antifungal agent binding to ergosterol on a fungal cell membrane to induce depolarization of the cell membrane and forming a hole to induce the loss of contents in a cell, thereby killing fungi. Such an ergosterol-binding antifungal agent is known in the art, and any ergosterol-binding antifungal agent considerably increases the antifungal effect when used with the antifungal pharmaceutical composition. In one exemplary embodiment, the ergosterol-binding antifungal agent may be a polyene-based antifungal agent. In one aspect, the polyene-based antifungal agent may be at least one antifungal agent selected from the group consisting of amphotericin B, natamycin, rimocidin, filipin, nystatin and candicin. In the preferable embodiment, the polyene-based antifungal agent is amphotericin B. Meanwhile, the azole-based antifungal agent may be at least one antifungal agent selected from the group consisting of ketoconazole, fluconazole, itraconazole and voriconazole.

In this aspect, an antifungal combined formulation including the antifungal pharmaceutical composition including the inhibitor of the present invention; and a known ergosterol-binding antifungal agent or azole-based antifungal agent are provided.

An antifungal pharmaceutical composition including an inhibitor against at least one protein or gene coding for the same selected from the group consisting of Ras1, Ras2, Cdc24, Gpa1, Cac1, Aca1, Pka1, Hsp12 and Hsp122 of *C. neoformans* to prepare an antifungal agent is also provided.

The inventors performed investigation on, rather than simply the genes involved in Ras and cAMP pathways, the roles of the genes involved in Ras and cAMP pathways, to develop a target for a new antifungal agent. The result newly revealed that, surprisingly, in the Ras and cAMP pathways of *C. neoformans*, when a RAS1, RAS2, CDC24, GPA1, CAC1, ACA1, PKA1, HSP12 or HSP122 gene is inhibited, a sensitivity to one of the polyene- or azole-based drugs, an itraconazole antifungal agent, is increased. As will be confirmed in the following exemplary embodiment, when the genes are inhibited, the sensitivity to the polyene- or itraconazole antifungal agent in a fungus may be considerably increased. Thus, the antifungal pharmaceutical composition including an inhibitor against at least one protein or gene coding for the same selected from the group consisting of Ras1, Ras2, Cdc24, Gpa1, Cac1, Aca1, Pka1, Hsp12 and Hsp122 of *C. neoformans* may be used as an excellent combined antibacterial drug which can reduce an amount of a conventional polyene-based or itraconazole antifungal agent used and improve an efficiency.

Therefore, use of an inhibitor against at least one protein or gene coding for the same selected from the group consisting of Ras1, Ras2, Cdc24, Gpa1, Cac1, Aca1, Pka1, Hsp12 and Hsp122 of *C. neoformans* to prepare an antifungal agent, an antifungal pharmaceutical composition including the inhibitor, and a method of treating fungal infection including injecting an effective amount of the inhibitor into a subject are provided.

In the present invention, it is construed that RAS1, RAS2, CDC24, GPA1, CAC1, ACA1, PKA1, HSP12 or HSP122 used as a target to interrupt the Ras- and cAMP signal transduction systems is a Ras1, Ras2, Cdc24, Gpa1, Cac1, Aca1, Pka1, Hsp12 or Hsp122 protein, or a RAS1, RAS2, CDC24, GPA1, CAC1, ACA1, PKA1, HSP12 or HSP122 gene. Accordingly, it is construed that a RAS1, RAS2, CDC24, GPA1, CAC1, ACA1, PKA1, HSP12 or HSP122 inhibitor includes every inhibitor against the Ras1, Ras2, Cdc24, Gpa1, Cac1, Aca1, Pka1, Hsp12 or Hsp122 protein or inhibitor against the RAS1, RAS2, CDC24, GPA1, CAC1, ACA1, PKA1, HSP12 or HSP122 gene.

In one exemplary embodiment, an inhibitor against at least one protein selected from the group consisting of Ras1, Ras2, Cdc24, Gpa1, Cac1, Aca1, Pka1, Hsp12 and Hsp122 of *C. neoformans* may be an inhibitor that binds to the protein to inhibit an activity, thereby interrupting signal transduction. In another exemplary embodiment, an inhibitor against at least one gene selected from the group consisting of RAS1, RAS2, CDC24, GPA1, CAC1, ACA1, PKA1, HSP12 and HSP122 of *C. neoformans* may be an inhibitor inhibiting expression of the gene, thereby interrupting signal transduction. In the present invention, the RAS1, RAS2, CDC24, GPA1, CAC1, ACA1, PKA1, HSP12 or HSP122 gene may be DNA coding for the gene or mRNA transcripted therefrom. Therefore, the inhibitor against the gene may bind to the gene to interrupt transcription or bind to mRNA transcripted from the gene to interrupt translation of the mRNA.

In one exemplary embodiment of the present invention, the Ras1, Ras2, Cdc24, Gpa1, Cac1, Aca1, Pka1, Hsp12 or Hsp122 protein may have an amino acid sequence of one of SEQ ID NOs: 22-30 respectively, and the RAS1, RAS2, CDC24, GPA1, CAC1, ACA1, PKA1, HSP12 or HSP122 gene may have a nucleic acid or cDNA sequence corresponding to the protein. However, the sequence just shows a sequence of a *C. neoformans* antigen-type A H99 strain, and thus the sequence of the RAS1, RAS2, CDC24, GPA1, CAC1, ACA1, PKA1, HSP12 or HSP122 is not limited thereto.

In the present invention, it is construed that the Ras1, Ras2, Cdc24, Gpa1, Cac1, Aca1, Pka1, Hsp12 or Hsp122 protein, or the RAS1, RAS2, CDC24, GPA1, CAC1, ACA1, PKA1, HSP12 or HSP122 gene includes a variant or fragment thereof having substantially the same activity as the protein or gene.

In one exemplary embodiment, the inhibitor may be an inhibitor against a Cac1 or Pka1 protein or gene.

Inhibition of the Ras1, Ras2, Cdc24, Gpa1, Cac1, Aca1, Pka1, Hsp12 or Hsp122 protein or gene coding for the same may increase a sensitivity to a polyene- or azole-based antifungal agent, and thus an effective amount of the polyene- or azole-based antifungal agent may be reduced and a killing ability of the antifungal agent may be increased. An antifungal activity caused by the inhibition of the Ras1, Ras2, Cdc24, Gpa1, Cac1, Aca1, Pka1, Hsp12 or Hsp122 may treat cryptococcal disease and encephalomeningitis induced by infection of *C. neoformans*.

Thus, in one exemplary embodiment of the present invention, use of a Ras1, Ras2, Cdc24, Gpa1, Cac1, Aca1, Pka1, Hsp12 or Hsp122 inhibitor to prepare a drug for treating diseases such as cryptococcal disease and encephalomeningitis, a pharmaceutical composition for treating diseases such as cryptococcal disease and encephalomeningitis including the Ras1, Ras2, Cdc24, Gpa1, Cac1, Aca1, Pka1, Hsp12 or Hsp122 inhibitor and a method of treating diseases such as cryptococcal disease and encephalomeningitis including injecting an effective amount of the Ras1, Ras2, Cdc24, Gpa1, Cac1, Aca1, Pka1, Hsp12 or Hsp122 inhibitor into a subject are provided.

Other than the cryptococcal disease and encephalomeningitis stated herein, diseases induced by fungal infection are well known in the art. In the present invention, it is revealed that the inhibition of the Ras1, Ras2, Cdc24, Gpa1, Cac1, Aca1, Pka1, Hsp12 or Hsp122 protein or gene coding for the same increases the sensitivity to a polyene- or azole-based itraconazole antifungal agent, thereby increasing the efficiency of the antifungal agent. Therefore, those of ordinary skill in the art can inhibit the protein or genes to prevent or treat a disease induced by the fungal infection.

In the present invention, the "inhibitor of the Ras1, Ras2, Cdc24, Gpa1, Cac1, Aca1, Pka1, Hsp12 or Hsp122 protein" used to interrupt the RAS or cAMP signal transduction system includes every inhibitor binding to the Ras1, Ras2, Cdc24, Gpa1, Cac1, Aca1, Pka1, Hsp12 or Hsp122 protein to interrupt signal transduction. For example, such an inhibitor may be a peptide or compound binding to the Ras1, Ras2, Cdc24, Gpa1, Cac1, Aca1, Pka1, Hsp12 or Hsp122 protein. The inhibitor may be selected by a screening method to be described below in analysis of a protein structure, and may be designed using a method known in the art. In one exemplary embodiment, the inhibitor may be a polyclonal or monoclonal antibody with respect to at least one protein selected from the group consisting of Ras1, Ras2, Cdc24, Gpa1, Cac1, Aca1, Pka1, Hsp12 and Hsp122 of *C. neoformans*. The polyclonal or monoclonal antibody may be constructed using a known method of constructing an antibody in the art.

In the present invention, the "inhibitor of the RAS1, RAS2, CDC24, GPA1, CAC1, ACA1, PKA1, HSP12 or HSP122 gene" used to interrupt the RAS or cAMP signal transduction system includes every inhibitor inhibiting the expression of the RAS1, RAS2, CDC24, GPA1, CAC1, ACA1, PKA1, HSP12 or HSP122 gene to interrupt signal transduction. For example, such an inhibitor may be a peptide, nucleic acid or compound binding to the gene. The inhibitor may be selected by a screening method to be described below in analysis of a protein structure, and may be designed using a method known in the art. In one exemplary embodiment, the inhibitor may be an antisense oligonucleotide, siRNA, shRNA, miRNA or a vector including the same with respect to at least one gene selected from the group consisting of RAS1, RAS2, CDC24, GPA1, CAC1, ACA1, PKA1, HSP12 and HSP122 of *C. neoformans*. Such an antisense oligonucleotide, siRNA, shRNA, miRNA or a vector including the same may be constructed using a known method in the art. In the present invention, the "vector" is a gene construct including foreign DNA inserted into a genome coding for a polypeptide. The vector related to the present invention may be a vector formed by inserting a nucleic acid sequence inhibiting the gene into the genome, which may be a DNA vector, plasmid vector, cosmid vector, bacteriophage vector, yeast vector or viral vector.

The antifungal pharmaceutical composition of the present invention including the inhibitor against at least one protein or gene coding for the same selected from the group consisting of Ras1, Ras2, Cdc24, Gpa1, Cac1, Aca1, Pka1, Hsp12 and Hsp122 of *C. neoformans* increases a fungal killing ability of the antifungal agent in combination with a polyene- or azole-based antifungal agent. Thus, the antifungal pharmaceutical composition of the present invention is sequentially or simultaneously injected with the polyene- or azole-based antifungal agent. The polyene- or azole-based antifungal agent is known in the art, and any one of the polyene- or azole-based antifungal agent significantly increases the antifungal effect when used with the antifungal pharmaceutical composition of the present invention. In one aspect, the polyene-based antifungal agent may be at least one of amphotericin B, natamycin, rimocidin, filipin, nystatin and candicin. In a preferable embodiment, the polyene-based antifungal agent may be amphotericin B. In one aspect, the azole-based antifungal agent may be at least one selected from the group consisting of ketoconazole, fluconazole, itraconazole and voriconazole.

In another exemplary embodiment, the antifungal pharmaceutical composition may be sequentially or simultaneously injected along with the inhibitor against at least one protein selected from the group consisting of SSK1, TCO2, SSK2, PBS2, HOG1, ENA1 and NHA1 of *C. neoformans*. As will be confirmed from the following exemplary embodiment, when expression of HOG1 is inhibited as well as expression of CAC1 or PKA1 of *C. neoformans*, the sensitivity to amphotericin B is proportionally increased. This is because genes of the cAMP pathway increase the sensitivity to amphotericin B by a mechanism different from that increasing the sensitivity to amphotericin B due to the increase in biosynthesis of ergosterol when the genes of the HOG pathway described above are inhibited.

According to the aspect, the present invention also provides an antifungal combined formulation including the antifungal pharmaceutical composition including the inhibitor of the present invention; and at least one antifungal agent selected from the group consisting of a polyene-based antifungal agent, an azole-based antifungal agent and an inhibitor against at least one protein or gene coding for the same selected from the group consisting of Ssk1, Tco2, Ssk2, Pbs2, Hog1, Ena1 and Nha1 of *C. neoformans*. Preferably, the antifungal combined formulation may include the antifungal pharmaceutical composition including the inhibitor of the present invention, a polyene-based antifungal agent, and at least one antifungal agent selected from the group consisting of inhibitors each against at least one protein or gene coding for the same selected from the group consisting of Ssk1, Tco2, Ssk2, Pbs2, Hog1, Ena1 and Nha1 of *C. neoformans*.

The antifungal pharmaceutical composition or antifungal combined formulation of the present invention may be prepared using a pharmaceutically suitable and physiologically available adjuvant, wherein the adjuvant may be a solubilizer such as a diluting agent, a dispersing agent, a sweetening agent, a binding agent, a coating agent, a blowing agent, a lubricant, a gliding agent or a flavoring agent.

The antifungal pharmaceutical composition of the present invention may be formulated into a pharmaceutical composition including at least one pharmaceutically available carrier other than an active component for administration.

In the composition formulated in a liquid-phase solution, a pharmaceutically available carrier may be suitable for sterilization and living organisms, and may be saline, sterilized water, Ringer's solution, buffered saline, albumine injection, dextrose solution, maltodextrin solution, glycerol, ethanol or a mixture of at least one thereof. When necessary, another conventional additive such as an antioxidant, buffer or bacteriostatic agent may be added. In addition, a diluting agent, a dispersing agent, a surfactant, a binding agent or a lubricant may be added, and thus the composition may be formulated in the form of an injectable formulation such as an aqueous solution, a suspension or an emulsion, a pill, a capsule, a granule or a tablet. Furthermore, the composition may be formulated using a suitable method in the art, which is disclosed in Remington's Pharmaceutical Science, Mack Publishing Company, Easton, Pa. according to diseases or components.

Types of a pharmaceutical formulation of the pharmaceutical composition of the present invention may include a granule, an acida, a coated tablet, a tablet, a capsule, a suppository, a syrup, a juice, a suspension, an emulsion, a drop or injectable liquid and a sustained-release formulation of an active compound.

The pharmaceutical composition of the present invention may be injected by a conventional method via an intravenous, intraarterial, abdominal, sternal, percutaneous, nasal, inhaling, local, rectal, oral, intraocular or intradermal route.

An effective amount of the active component of the pharmaceutical composition of the present invention indicates an amount required for preventing or treating a disease, or achieving an effect of inducing bone growth. Accordingly, the effective amount may vary depending on various factors such as kinds of a disease, severity of a disease, kinds and contents of the active component and other components contained in the composition, kinds of dosage forms and patient's age, weight, health, sex and dietary habits, injection times and routes, release rates of the composition, duration of treatment, and co-injected drugs. For adults, when the composition is injected one or more times a day, the dosages may be, but not limited to, 0.1 ng/kg to 10 g/kg for a compound, 0.1 ng/kg to 10 g/kg for a polypeptide, protein or antibody, and 0.01 ng/kg to 10 g/kg for an antisense oligonucleotide, siRNA, shRNAi or miRNA, respectively.

In the present invention, the "subject" may be, but not limited to, a human, orangutan, chimpanzee, mouse, rat, dog, cow, chicken, pig, goat or sheep.

Furthermore, the present invention provides a use of at least one protein selected from the group consisting of Ssk1, Tco2, Ssk2, Pbs2, Hog1, Ena1 and Nha1 of *C. neoformans* to screen an antifungal agent, a composition for screening an antifungal agent including the protein, and a method of screening an antifungal agent including contacting the protein with a candidate material and determining whether the candidate material inhibits or stimulates an activity of the protein.

The present invention also provides a use of at least one gene selected from the group consisting of SSK1, TCO2, SSK2, PBS2, HOG1, ENA1 and NHA1 of *C. neoformans* to screen an antifungal agent, a composition for screening an antifungal agent including the gene, and a method of screening an antifungal agent including contacting the gene with a candidate material and determining whether the candidate material inhibits or stimulates expression of the gene.

The present invention also provides a method of screening an antifungal agent by a yeast two-hybrid system capable of monitoring physical contact between SSK1 and SSK2, SSK1 and YPD1 or YPD1 and TCO2 proteins of *C. neoformans*. When this method is used, a large amount of the candidate materials can be screened quickly.

As described above, when SSK1, TCO2, SSK2, PBS2 or HOG1 of *C. neoformans* is inhibited, the HOG1 signal transduction system is interrupted, and thus biosynthesis of ergosterol is improved. Therefore, the material screened to inhibit the protein or gene may be used as an antifungal agent improving a fungal killing ability, along with an ergosterol-binding antifungal agent. The material screened to inhibit ENA1 or NHA1 may be used as an antifungal agent improving a fungal killing ability when used with an ergosterol-binding antifungal agent or azole-based antifungal agent.

The present invention also provides a use of at least one protein selected from the group consisting of Ras1, Ras2, Cdc24, Gpa1, Cac1, Aca1, Pka1, Hsp12 and Hsp122 of *C. neoformans* to screen an antifungal agent, a composition for screening an antifungal agent including the protein, and a method of screening an antifungal agent including contacting the protein with a candidate material and determining whether the candidate material inhibits or stimulates an activity of the protein.

The present invention also provides a use of at least one gene selected from the group consisting of RAS1, RAS2, CDC24, GPA1, ACA1, PKA1, HSP12 and HSP122 of *C. neoformans* to screen an antifungal agent, a composition for screening an antifungal agent including the gene, and a method of screening an antifungal agent including contacting the gene with a candidate material and determining whether the candidate material inhibits or stimulates expression of the gene.

The present invention also provides a method of screening an antifungal agent by a yeast two-hybrid system capable of monitoring physical contact between Gpa1 and Cac1, Cac1 and Aca1, Ras1 and Cdc24 or Ras2 and Cdc24 proteins of *C. neoformans*. When this method is used, a large amount of the candidate materials can be screened quickly.

As described above, when RAS1, RAS2, CDC24, GPA1, CAC1, ACA1, PKA1, HSP12 or HSP122 of *C. neoformans* is inhibited, the RAS or cAMP signal transduction system is interrupted, thereby increasing a sensitivity to a polyene- or azole-based antifungal agent. Thus, the material screened to inhibit the protein or gene may be used as an antifungal agent improving a fungal killing ability when used with the polyene- or azole-based antifungal agent.

Confirmation of the reaction between the protein or gene and the candidate material may be performed by a conventional method of confirming the reaction between a protein and a protein, a protein and a compound, DNA and DNA, DNA and RNA, DNA and a protein, DNA and a compound, RNA and a protein, or RNA and a compound. For example, a hybrid test for confirming a bond between the gene and a candidate material in vitro, a method of measuring an expression level of the gene through northern blotting, quantitative PCR or quantitative real time PCR after reaction of mammalian cell and a test material, a method of connecting a reporter gene to the gene to introduce the gene into a cell, reacting the cell with a test material and measuring an expression level of a reporter protein, a method of reacting the protein with a candidate material and measuring an activity, a yeast two-hybrid, searching for a phage-displayed peptide clone binding to an Idbf protein, high throughput screening (HTS) using a natural substance and a chemical library, drug hit HTS, cell-based screening or a screening method using a DNA array may be used.

The screening composition may include distilled water or a buffer stably maintaining the structure of a nucleic acid or protein, other than the protein or gene. In addition, the screening composition may include a cell expressing the protein or gene, or a cell containing a plasmid expressing the gene in the presence of a promoter regulating a transcription rate for an in vivo test.

In the screening method of the present invention, a test material may be individually a nucleic acid, a protein, a peptide, a different extract or natural substance or a compound assumed to have possibility as a drug inhibiting signal transduction through a HOG1 signal transduction system according to a conventional screening method or randomly selected.

The matters related to a genetic engineering technique in the present invention are made more clear by the literatures disclosed by Sambrook et al. [Molecular Cloning, A Laboratory Manual, Cold Spring Harbor laboratory Press, Cold Spring Harbor, N.Y. (2001)] and Frederick M. Ausubel et al. [Current protocols in molecular biology volume 1, 2, 3, John Wiley & Sons, Inc. (1994)].

While exemplary embodiments have been disclosed herein, it should be understood that other variations may be possible. Such variations are not to be regarded as a departure from the spirit and scope of exemplary embodiments of the present application, and all such modifications as would be obvious to one skilled in the art are intended to be included within the scope of the following claims.

EXAMPLES

Experimental Procedures

Strains and Growth Conditions

The *C. neoformans* strains used in this examples are listed in Table 1 [Bahn Y S, Geunes-Boyer S, Heitman J (2007) Eukaryot Cell 6: 2278-2289; Bahn Y S, Kojima K, Cox G M, Heitman J (2005) Mol Biol Cell 16: 2285-2300; Bahn Y S, Kojima K, Cox G M, Heitman J (2006) Mol Biol Cell 17: 3122-3135; Perfect J R, Ketabchi N, Cox G M, Ingram C W, Beiser C L (1993) J Clin Microbiol 31: 3305-3309; Kwon-Chung K J, Edman J C, Wickes B L (1992) Genetic association of mating types and virulence in *Cryptococcus neoformans*. Infect Immun 60: 602-605.].

The *C. neoformans* strains were cultured in YPD (yeast extract-peptone-dextrose) medium unless indicated separately.

TABLE 1

| Strain | Genotype | Parent |
|---|---|---|
| Serotype A | | |
| H99 | MATα | |
| KN99 | MATa | |
| CBN45 | MATα ras1Δ::NEO | H99 |
| CBN64 | MATα ras1Δ::NEO RAS1::NAT | CBN45 |
| MWC12 | MATα ras2Δ::URA5 | H99 |
| CBN32 | MATα cdc24Δ::NEO | H99 |
| CBN33 | MATα cdc24Δ::NEO CDC24::NAT | CBN32 |
| YSB6 | MATα aca1Δ::NAT-STM#43 | H99 |
| YSB51 | MATα ras1Δ::NAT-STM#150 | H99 |
| YSB53 | MATα ras1Δ::NAT-STM#150 | H99 |
| YSB64 | MATα hog1Δ::NAT-STM#177 | H99 |

TABLE 1-continued

| Strain | Genotype | Parent |
|---|---|---|
| YSB123 | MATα pbs2Δ::NAT-STM#213 | H99 |
| YSB261 | MATα ssk1Δ::NAT-STM#205 | H99 |
| YSB264 | MATα ssk2Δ::NAT-STM#210 | H99 |
| YSB349 | MATα skn7Δ::NAT-STM#201 | H99 |
| YSB278 | MATα tco1Δ::NAT-STM#102 | H99 |
| YSB281 | MATα tco2Δ::NAT-STM#116 | H99 |
| YSB324 | MATα tco1Δ::NAT-STM#102 tco2D::NEO | YSB278 |
| YSB284 | MATα tco3Δ::NAT-STM#119 | H99 |
| YSB417 | MATα tco4Δ::NAT-STM#123 | H99 |
| YSB286 | MATα tco5Δ::NAT-STM#125 | H99 |
| YSB348 | MATα tco7Δ::NAT-STM#209 | H99 |
| YSB73 | MATα ras1Δ::NEO | H99 |
| YSB42 | MATα cac1Δ::NAT-STM#159 | H99 |
| YSB83 | MATα gpa1Δ::NAT | H99 |
| YSB188 | MATα pka1Δ::NAT | H99 |
| YSB194 | MATα pka2Δ::NAT-STM#205 | H99 |
| YSB200 | MATα pka1Δ::NAT pka2Δ::NEO | YSB188 |
| YSB174 | MATα aca1Δ::NAT-STM#43 ras1::NEO | YSB278 |
| YSB182 | MATα cac1Δ::NAT-STM#159 ras1::NEO | H99 |
| YSB156 | MATα hog1Δ::NAT-STM#177 cac1::NEO | H99 |
| YSB112 | MATα ura5 pka1::URA5 hog1::NATSTM#177 | H99 |
| YSB58 | MATa aca1Δ::NEO | KN99 |
| YSB79 | MATa cac1Δ::NEO | KN99 |
| YSB81 | MATa hog1Δ::NEO | KN99 |
| YSB175 | MATα aca1Δ::NEO ras1Δ::NATSTM#150 | YSB58 |
| YSB187 | MATα cac1Δ::NEO ras1Δ::NATSTM#150 | YSB79 |
| YSB606 | MATα gre2Δ::NAT-STM#224 | H99 |
| YSB607 | MATα gre2Δ::NAT-STM#224 | H99 |
| YSB609 | MATα pkp1Δ::NAT-STM#224 | H99 |
| YSB610 | MATα pkp1Δ::NAT-STM#224 | H99 |
| YSB599 | MATα hsp12Δ::NAT-STM#224 | H99 |
| YSB600 | MATα hsp12Δ::NAT-STM#224 | H99 |
| YSB603 | MATα hsp122Δ::NAT-STM#224 | H99 |
| YSB604 | MATα hsp122Δ::NAT-STM#224 | H99 |
| YSB590 | MATα ena1Δ::NAT nha1::NEO | AI167 |
| YSB591 | MATα ena1Δ::NAT nha1::NEO | AI167 |
| YSB586 | MATα nha1Δ::NEO | H99 |
| YSB587 | MATα nha1Δ::NEO | H99 |
| YSB588 | MATα nha1Δ::NEO | H99 |
| Serotype D | | |
| JEC21 | MATα | |
| B-3501 | MATα | |
| YSB267 | MATα pbs2Δ::NAT-STM#213 | JEC21 |
| YSB139 | MATα hog1Δ::NAT-STM#177 | JEC21 |
| YSB338 | MATα ssk2Δ::NAT-STM#210 | JEC21 |
| YSB340 | MATα ssk2Δ::NAT-STM#210 | B-3501 |

Each NAT-STM# indicates the $Nat^r$ marker with a unique signature tag.

DNA Microarray Array Analysis

For total RNA isolation used in DNA microarray, the wild-type H99, hog1Δ (YSB64), ssk1Δ (YSB261), and skn7Δ (YSB349), ras1Δ (YSB51), aca1Δ (YSB6), gpa1Δ (YSB83), cac1Δ (YSB42) and pka1Δ pka2Δ (YSB200) mutant strains were grown in 50 ml YPD medium at 30° C. for 16 hr. Then 5 ml of the overnight culture was inoculated into a 100 ml of fresh YPD medium and further incubated for 4-5 hr at 30° C. until it approximately reaches to the 1.0 of optical density (OD) at 600 nm (OD600 nm=1.0). For zero-time samples, 50 ml out of the 100 ml culture was sampled and rapidly frozen in liquid nitrogen. To the remaining 50 ml culture, 50 ml of YPD containing 2 M NaCl, 40 μg/ml fludioxonil (PESTANAL, Sigma, 100 mg/ml stock solution in dimethylsulfoxide), or 5 mM H2O2 was added (final concentration of 1 M NaCl, 20 μg/ml fludioxonil, or 2.5 mM H2O2, respectively). During incubation in each stress-inducing medium, 50 ml of the culture was sampled at 30 and 60 min, pelleted in a tabletop centrifuge, frozen in liquid nitrogen, and lyophilized overnight. The lyophilized cells were subsequently used for total RNA isolation. As biological replicates for DNA microarray, 3 independent cultures for each strain and growth condition were prepared for total RNA isolation.

Total RNA Preparation

For total RNA isolation, the lyophilized cell pellets were added with 3 ml volume of sterile 3 mm glass bead (SIGMUND LINDER), homogenized by shaking, added with 4 ml of TRizol reagent (Tri reagent, Molecular Research Center), and allowed to incubate at room temperature for 5 min. Then 800 μl of chloroform was added, incubated for 3 min at room temperature, transferred to the 15 ml of the round-bottom tube (SPL), and centrifuged by 10,000 rpm at 4° C. for 15 min (Sorvall SS-34 rotor). Two milliliter of the supernatant was transferred to the new round-bottom tube, added with 2 ml isopropanol, inverted several times, and allowed to incubate for 10 min at room temperature. Then the mixture was re-centrifuged by 10,000 rpm at 4° C. for 10 min, and its pellet was washed with 4 ml of 75% ethanol diluted with diethylpyrocarbonate (DEPC) treated water and centrifuged by 8,000 rpm at 4° C. for 5 min. The pellet was dried at room temperature and resuspended with 500 μl DEPC-treated water. Concentration and purity of total RNA sample were calculated by measuring OD260 nm and gel electrophoresis, respectively. For control total RNA (for Cy3 labeling), all of total RNAs prepared from wild-type, hog1Δ, ssk1Δ, skn7Δ, ras1Δ, aca1Δ, gpa1Δ, cac1Δ and pka1Δ pka2Δ mutant cells grown in conditions described above were pooled (pooled reference RNAs).

cDNA Synthesis and Cy3/Cy5 Labeling

For cDNA synthesis, total RNA concentration was adjusted to 1 μg/μl with DEPC-treated water, and 15 μl of the total RNA (15 μg) was added with 1 μl of 5 μg/μl oligo dT (5'-TTTTTTTTTTTTTTTTTTTTV-3') (SEQ ID NO:31)/pdN6 (Amersham) (1:1 mixture of 10 μg/μl, respectively), incubated at 70° C. for 10 min, and place on ice for 10 min. Then 15 μl of cDNA synthesis mixture {3 μl 0.1 M DTT, 0.5 μl RNasin [Promega], 0.6 μl aa-dUTP (5-(3-aminoallyl)-2'-deoxyuridine 5'-triphosphate)/dNTPs [a mixture of 6 μl dTTP (100 mM), 4 μl aa-dUTP (100 mM), 10 μl dATP (100 mM), 10 μl dCTP (100 mM), 10 μl dGTP (100 mM)], 1.5 μl AffinityScript reverse transcriptase (Stratagene), 3 μl AffinityScript buffer, 7 μl water] was added and incubated at 42° C. for 2 hrs. Then 10 μl of 1 N NaOH and 10 μl of 0.5 M EDTA (pH 8.0) were added and incubated at 65° C. for 15 min. After incubation, 25 μl of 1 M HEPES buffer (pH 8.0) and 450 μl of DEPE-treated water were added, and the whole mixture was concentrated through Microcon30 filter (Milipore) and vacuum-dried for 1 hr.

For Cy3 and Cy5 (Amersham) labeling of the prepared cDNA, Cy3 and Cy5 were dissolved in 10 μl DMSO and 1.25 μl of each dye was aliquoted into separate tubes. The cDNAs prepared as described above were added with 9 μl of 0.05 M Na-bicarbonate (pH 8.0) and incubate at room temperature for 15 min. The cDNAs prepared from pooled reference RNAs were mixed with Cy3 as a control and the cDNAs prepared from each test RNA (each experimental condition) were mixed with Cy5. Each mixture was further incubated at room temperature for 1 hr in the dark and purified by QIAquick PCR purification kit (QIAGEN).

Microarray Hybridization and Washing

*C. neoformans* serotype D 70-mer microarray slide containing 7,936 spots (Duke University) was pre-hybridized at 42° C. in 60 ml of pre-hybridization buffer [42.4 ml sterile distilled water, 2 ml 30% BSA (Sigma), 600 μl 10% SDS, 15 ml 20×SSC], washed with distilled water and isopropanol, and dried by brief centrifugation (110×g, 2 min) The Cy3- and Cy5-labeled cDNA samples were combined, concentrated through Microcon30 filter, and vacuum-dried. The dried cDNA samples were resuspended with 24 μl of 1× hybridization buffer [250 μl 50% formamide, 125 μl 20×SSC, 5 μl 10% SDS, 120 μl dH2O, total 500 μl], added with 1 μl polyA tail DNA (Sigma), further incubated at 100° C. for 3 min and allowed to cool for 5 min at room temperature. The microarray slides were aligned into the hybridization chamber (DieTech), removed of any dusts, and covered by Lifterslips (Erie Scientific). The Cy3/Cy5-labeled cDNA samples were applied in between Lifterslips and slides. To prevent slides from being dried, 10 μl of 3×SSC buffer was applied onto the slides, which were subsequently incubated for 16 hr at 42° C. After incubation, the microarray slides were washed with three different washing buffers [wash buffer 1 (10 ml 20×SSC, 600 μl 10% SDS, 189.4 ml dH2O, preheated at 42° C.), wash buffer 2 (3.5 ml 20×SSC, 346.5 ml dH2O), wash buffer 3 (0.88 ml 20×SSC, 349.12 ml dH2O)] for 2, 5, and 5 min, respectively, on the orbital shaker.

For each total RNA sample, 3 independent DNA microarray with 3 independent biological replicates were performed, including one-dye swap experiment.

Microarray Slide Scanning and Data Analysis

After hybridization and washing, the microarray slides were scanned by GenePix 4000B scanner (Axon Instrument) and the signals were analyzed with GenePix Pro (Ver. 4.0) and gal file (http://genome.wustl.edu/activity/ma/*cneoformans*). Since we used total RNAs isolated from serotype A *C. neoformans* strains, 70-mer oligonucleotide sequence printed on the serotype D *C. neoformans* slides was queried against serotype A *C. neoformans* genome database by blastp search (e-value cut-off: e-4) to find the corresponding serotype A gene ID. Using the serotype A gene sequence, each *S. cerevisiae* gene name or ID listed in the Tables was identified by blastp search (e-value cut-off: e-4).

For further hierarchical and statistical analysis, data transported from GenePix software were analyzed with GeneSpring (Agilent) by employing LOWESS normalization, reliable gene filtering, clustering (standard correlation and average linkage) and zero-transformation, and ANOVA analysis ($P<0.01$).

Ergosterol Assay

Ergosterol contents were measured as previously described in "Arthington-Skaggs B A, Jradi H, Desai T, Morrison C J (1999) Quantitation of ergosterol content: novel method for determination of fluconazole susceptibility of *Candida albicans*. J Clin Microbiol 37: 3332-3337", but with slight modification. Briefly, each *C. neoformans* strain was grown in 100 ml YPD medium for 24 h at 30° C. The 100 ml culture was splitted into two 50 ml cultures for duplicate measurement, pelleted in a tabletop centrifuge, and washed with sterile water. The cell pellet was frozen in liquid nitrogen and lyophilized overnight. The dried cell pellet was weighed for normalization of ergosterol contents, added with 5 ml of 25% alcoholic potassium hydroxide, and transferred to a sterile borosilicated glass screw-cap tube. Subsequently, the cells were incubated at 80° C. for 1 h and allowed to cool to room temperature. Then 1 ml of sterile water and 3 ml of heptane were added and vortexed for 3 min. Then 200 μl of the heptane layer is sampled and mixed with 800 μl of 100% ethanol, and its optical density (OD) was measured at both 281.5 nm and 230 nm. Ergosterol contents were calculated as the following: % ergosterol=[(OD281.5 nm/290)×F]/pellet weight−[(OD230 nm/518)×F]/pellet weight, where F is the ethanol dilution factor and 290 and 518 are the E values (in percentages per centimeter) determined for crystalline ergosterol and 24(28)dehydroergosterol, respectively.

Stress Sensitivity Test

Each strain was incubated overnight at 30° C. in YPD medium, washed, serially diluted (1 to $10^4$ dilutions) in $dH_2O$, and spotted (3 μl) onto solid YPD medium containing indicated concentrations of stress-inducing agents or antifungal drugs as previously described in "Bahn Y S, Kojima K, Cox G M, Heitman J (2005) Mol Biol Cell 16: 2285-2300." and "Bahn Y S, Kojima K, Cox G M, Heitman J (2006) Mol Biol Cell 17: 3122-3135". To examine antifungal drug sensitivity, the cells were spotted on agar-solid YPD media containing amphotericin B (Sigma), fluconazole (Sigma), itraconazole (Sigma), ketoconazole (Sigma) and fludioxonil. Then spotted cells were incubated at 30° C. for 2-4 days and photographed.

Disruption of cAMP-Signaling Dependent Genes

For gene disruption, information of genomic DNA structure (exon and intron) for each gene was obtained from serotype A *C. neoformans* genome database (http://www.broadinstitute.org/annotation/genome/*cryptococcus__neoformans*/MultiHome.html). The GRE2 (CNAG__02182.2), HSP12 (CNAG__03143.2), HSP122 (CNAG__01446.2) and PKP1 (CNAG__00396.2) genes were deleted by overlap PCR or double joint PCR (DJ-PCR) with split markers and biolistic transformation in the *C. neoformans* serotype A H99 strain as previously described (Bahn et al., 2005, Davidson et al., 2002). Primers for generation of the 5' and 3' flanking regions of each gene and dominant selectable nourseothricin resistant marker (NAT, nourseothricin acteryltransferase) were described in the supplemental table 1. Gold microcarriers beads (0.8~1.2-μm [Bioworld Inc] or 0.6-μm [BioRad]) were coated with gel-extracted deletion cassettes produced by overlap PCR and biolistically transformed into the strain H99. Stable transformants selected on YPD medium containing nourseothricin or G418 were subject to the first screening by diagnostic PCR with primers listed in Table 2. Positive mutants were further confirmed by Southern blot analysis using gene-specific probes prepared by primers listed in Table 2.

TABLE 2

| Primer Name | Sequence | Description |
|---|---|---|
| B79 | TGTGGATGCTGGCGGAGGATA (SEQ ID NO: 32) | Screening primer on ACT promtre |
| B1026 | GTAAAACGACGGCCAGTGAGC (SEQ ID NO: 33) | M13 forward (extended) |
| B1027 | CAGGAAACAGCTATGACCATG (SEQ ID NO: 34) | M13 reverse (extended) |
| B1614 | TGTTTAGCACCAGCGGAGTC (SEQ ID NO: 35) | HSP12-5' screening primer |
| B1615 | CACGATGAAAGTGCGTTGAAG (SEQ ID NO: 36) | HSP12 - left flanking primer 1 |
| B1616 | GCTCACTGGCCGTCGTTTTACACTGTCGGTGAAAG ATTGC (SEQ ID NO: 37) | HSP12 - left flanking primer 2 |
| B1617 | CATGGTCATAGCTGTTTCCTGAGAACGACAACCA GGAGTC (SEQ ID NO: 38) | HSP12 - right flanking primer 1 |
| B1618 | GCTCTGTGCTGACATTATCTGC (SEQ ID NO: 39) | HSP12 - right flanking primer 2 |
| B1707 | GAAAGTGCGTTGAAGTGATG (SEQ ID NO: 40) | HSP12 - probe primer 1 |
| B1708 | AGTAGAAGCAGCGGACTAAAG (SEQ ID NO: 41) | HSP12 - probe primer 2 |
| B1619 | GCGTAGTGGAGATTGGTTTC (SEQ ID NO: 42) | GRE2 - 5' screening primer |
| B1620 | ATCCCCTCCACTTTACCTCC (SEQ ID NO: 43) | GRE2 - left flanking primer 1 |
| B1621 | GCTCACTGGCCGTCGTTTTACAAGTCTCCCTTAGC GATAG (SEQ ID NO: 44) | GRE2 - left flanking primer 2 |
| B1622 | CATGGTCATAGCTGTTTCCTGACCACACCCCTGAA GAAAC (SEQ ID NO: 45) | GRE2 - right flanking primer 1 |
| B1623 | AACTGTTTCGTCTTGTGTGC (SEQ ID NO: 46) | GRE2 - right flanking primer 2 |
| B1705 | ATAGCAACTTCTTCCGTCG (SEQ ID NO: 47) | GRE2 - probe primer 1 |
| B1706 | TGTTGCCTGTGCTCACTTG (SEQ ID NO: 48) | GRE2 - probe primer 2 |
| B1629 | CCTCTGACAGCCACATACTG (SEQ ID NO: 49) | PKP1 - 5' screening primer |
| B1630 | AATGAAGTTCCTGCGACAG (SEQ ID NO: 50) | PKP1 - left flanking primer 1 |
| B1631 | GCTCACTGGCCGTCGTTTTACAATGGGATGAGAA CGCAC (SEQ ID NO: 51) | PKP1 - left flanking primer 2 |

TABLE 2-continued

| Primer Name | Sequence | Description |
|---|---|---|
| B1632 | CATGGTCATAGCTGTTTCCTGAGCATTTTCCAGCA TCAGC (SEQ ID NO: 52) | PKP1 - right flanking primer 1 |
| B1633 | GGTGTGGAACATCTTTTGAG (SEQ ID NO: 53) | PKP1 - right flanking primer 2 |
| B1711 | CTGGTTCATCTTGGGTGTC (SEQ ID NO: 54) | PKP1 - probe primer 1 |
| B1712 | TCTGAGCATACCACTCCTTTAC (SEQ ID NO: 55) | PKP1 - probe primer 2 |
| B1666 | TCTCATTCGCATCCTCTG (SEQ ID NO: 56) | HSP122 - 5' screening primer |
| B1667 | GTTGGGCAGATAATGTTTGTG (SEQ ID NO: 57) | HSP122 - left flanking primer 1 |
| B1668 | GCTCACTGGCCGTCGTTTTACACGGCGTCAGACAT TGTG (SEQ ID NO: 58) | HSP122 - left flanking primer 2 |
| B1669 | CATGGTCATAGCTGTTTCCTGACAAGAGAAGTCC ACTACTCAG (SEQ ID NO: 59) | HSP122 - right flanking primer 1 |
| B1670 | GCAAGGTAATGATGAGCG (SEQ ID NO: 60) | HSP122 - right flanking primer 2 |
| B1709 | GCGACTGAGATGTAGACCAAC (SEQ ID NO: 61) | HSP122 - probe primer 1 |
| B1710 | CTCGGAACGACATAATAAGC (SEQ ID NO: 62) | HSP122 - probe primer 2 |
| B1673 | CACACCTGGTAAGAGATAGCG (SEQ ID NO: 63) | NHA1 - left flanking primer 1 |
| B1674 | GCTCACTGGCCGTCGTTTTACAGTGGTAGAAGTA GGGCAGC (SEQ ID NO: 64) | NHA1 - left flanking primer 2 |
| B1675 | CATGGTCATAGCTGTTTCCTGACAGGGTCCAACA AGGATG (SEQ ID NO: 65) | NHA1 - right flanking primer 1 |
| B1676 | TGCTACGATTGTGGTCAGCC (SEQ ID NO: 66) | NHA1 - right flanking primer 2 |
| B1677 | GGACGAGACGAGTTATCAAAC (SEQ ID NO: 67) | NHA1 - screening primer |
| B1698 | CTTCATCAACTTGCGTGC (SEQ ID NO: 68) | NHA1 - probe primer |

Example 1

DNA Microarray Analysis of *C. neoformans* hog1Δ, ssk1Δ, and skn7Δ Mutants

To investigate Hog1 signaling pathway in *C. neoformans*, we performed comparative transcriptome analysis of serotype A wild-type (WT, H99) strain, hog1Δ, ssk1Δ, and skn7Δ mutants under both normal growth conditions and stressed conditions, such as in the presence of osmotic shock (1 M NaCl), oxidative stress (2.5 mM H2O2), and antifungal drug fludioxonil (40 μg/ml), by using DNA microarray analysis. We isolated total RNAs from cells growing in each stress condition after zero (non-stress condition), 30, and 60 min incubation. We prepared 3 independent RNA samples for each condition as biological replicates for DNA microarray analysis. As a control RNA for common Cy3 labeling, we used reference RNAs that were pooled from all RNA samples prepared in this study. We used 70-mer serotype D *C. neoformans* DNA microarray chips containing total 7,936 spots, based on information from the *C. neoformans* genome database.

For basic validation of our array quality, we monitored expression levels of HOG1, SSK1, and SKN7 genes, and known Hog1-regulated genes, such as GPP1 (Glycerol-3-phosphatase) and GPD1 (Glycerol-3-phosphate dehydrogenase), in our array data.

FIG. 1 shows identification of genes whose expression is regulated by Hog, Ssk1 and Skn7 of *C. neoformans* under normal conditions with no stress on the genome level (fold change is expressed by color). FIG. 1A shows relative expression levels of HOG1, SSK1, and SKN7 genes in each corresponding mutant compared to WT strain. FIG. 1B shows condition tree analysis result in WT, hog1Δ, ssk1Δ, skn7Δ mutant. FIG. 1C shows clustering analysis result of 950 genes which are exhibited significantly different expression patterns in hog1Δ, ssk1Δ, or skn7Δ mutants compared to WT (ANOVA test, P<0.01) under normal growth condition (YDP, 30° C.). FIG. 1D shows Venn diagram presenting HOG1, SSK1, and SKN7-dependent genes that include genes up- or down-regulated over 2 folds.

As expected, relative expression levels of HOG1, SSK1, and SKN7 genes in each corresponding mutant compared to WT strain were very low (FIG. 1A). In addition, expression of GPD1 (glycerol-3-phosphate dehydrogenase, CNAG_01745) and GPP1 (DL-glycerol-3-phosphatase, CNAG_01744) homologous genes, which are well-known Hog1- regulated stress defense genes in other fungi, was highly reduced (4.5-fold and 2.5-fold reductions, respectively) in hog1Δ and ssk1Δ mutants, further supporting the quality of our array data.

We monitored how HOG1, SSK1, and SKN7 mutations affect gene expression patterns in *C. neoformans* under unperturbed normal conditions. Among 7,936 spots monitored, 3,858 spots were found to be reliable based on Cross-gene error model (cutoff 10). Supporting the previous finding, the transcription profile of the hog1Δ mutant was considerably similar to that of the ssk1Δ mutant, based on the condition tree analysis (FIG. 1B). A total of 950 genes in the reliable genes exhibited significantly different expression patterns in hog1Δ, ssk1Δ, or skn7Δ mutants compared to WT (ANOVA test, $P<0.01$) (FIG. 1C), indicating that about 15% of the whole *C. neoformans* genes could be transcriptionally affected by perturbation of the two-component system and HOG signaling pathways even under unstressed, normal conditions. Among them, 559 genes exhibited more than 2-fold induction in at least one of the mutants (FIG. 1D). Several key findings were made as the following. First, a majority of the genes (555 genes, 99%) were up- or down-regulated by either Ssk1 or Hog1 under unstressed conditions while only 51 genes (9%) were regulated by Skn7. Among the Skn7-dependent genes, only 4 genes were found to be Skn7-specific (FIG. 1D). Thus it appears to be clear that HOG1 and SSK1 mutations alter genome-wide transcription profiles under normal conditions in a greater scale than the SKN7 mutation (FIG. 1D). Second, there exist significantly higher overlaps between Ssk1- and Hog1-dependent genes (422 out of 555 genes, 76%) than between Skn7- and Hog1-dependent genes (45 out of 467 genes, 10%), further corroborating that Ssk1 is the major upstream regulator of the Hog1 MAPK. Third, regardless of the significant overlap in genes regulated by Ssk1 and Hog1, there were a number of Ssk1-specific (90 genes) and Hog1-specific (40 genes) genes, strongly suggesting that Ssk1 and Hog1 are not strictly in the linear pathway and could have other target(s) or upstream regulators, respectively (FIG. 1D). This explains why the ssk1Δ mutant exhibits slightly different phenotypes (i.e. higher sensitivity to hydrogen peroxide) compared to hog1Δ mutants and Hog1 can still be phosphorylated in the absence of Ssk1 response regulator under exposure to NaCl.

Genes regulated by Hog1 and Ssk1 cover a wide variety of functional categories, including energy production and conversion, amino acid/carbohydrate/lipid transport and metabolism, translational and protein biosynthesis, post-translational modification, signal transduction, stress-defense mechanisms, and others (Supplementary table 2), indicating that active remodeling of various aspects of cellular functions could occur simply by perturbation of the HOG pathway even without external stresses. Furthermore it should be noticed that more than one third of Hog1 and Ssk1-dependent genes do not have any functional orthologs in other organisms, indicating that *C. neoformans* appears to develop many *cryptococcus*-specific Hog1/Ssk1-dependent genes.

Among Ssk1- and Hog1-regulated genes identified by our array analysis, several groups of genes provided novel insights into the potential mechanism of the HOG pathway in controlling virulence factor and sexual reproduction of *C. neoformans*. First, a group of genes involved in iron transport and regulation were found to be highly induced in the ssk1Δ and hog1Δ mutants compared to the wild-type strain. These genes include SIT1 (CNAG_00815 and CNAG_07138) encoding siderophore-transporters, CFO1 (CNAG_06241) and CFO2 (CNAG_02958) encoding ferroxidases, and CFT1 (CNAG_06242) encoding Fe transporter. The *C. neoformans* Sit1 are homologous to the *S. cerevisiae* Arn3/Sit1 having high affinity for the hydroxamate siderophore ferrioxamine and *C. neoformans* Cfo1/Cfo2 and Cft1 are homologous to high-affinity iron permease/multicopper ferroxidase complex (Ftr1-Fet3) in *S. cerevisiae*. Since iron transport regulation and melanin synthesis seem to be closely related in *C. neoformans*, increased melanin synthesis observed in both hog1Δ and ssk1Δ mutants could be correlated with increased expression of a group of genes involved in iron transport.

Second, the GPA2 gene (CNAG_00179), encoding a G-protein α-subunit in the pheromone responsive MAPK pathway, is dramatically upregulated upon ssk1Δ or hog1Δ mutation (12.1- and 13.3-fold increases, respectively). This finding suggests that increased pheromone production and sexual reproduction found in ssk1Δ and hog1Δ mutants may result from enhanced expression of Gpa2 that is induced during mating and promotes the mating process of *C. neoformans*.

Third, several genes involved in oxidative stress defense were differentially regulated by HOG1 and SSK1 mutation. As expected from the previous finding that the hog1Δ and ssk1Δ mutants exhibit hypersensitivity to hydrogen peroxide, two genes (CNAG_04981 and CNAG_00575), which are homologous to the CTA1 gene encoding catalase A that detoxifies H2O2 to H2O, was drastically downregulated in both mutants (Supplementary Table 1). Furthermore, basal expression levels of the SOD2 gene (mitochondrial superoxide dismutase) were decreased in both hog1Δ and ssk1Δ mutants, further corroborating the role of the HOG pathway in oxidative stress response. Interestingly, however, basal expression levels of some genes involved in oxidative stress response [TRR1 (thioredoxin reductase), TSA1 (thioredoxin peroxidase), GRX5 (glutathione-dependent oxidoreductase), CCP1 (mitochondrial cytochrome-c peroxidase)] were more than 2-fold increased (3.8, 3.1, 2.1, and 9.5 fold changes, respectively) in the hog1Δ mutant, but not in the ssk1Δ mutant (Supplementary Table 2). The SRX1 gene (sulfiredoxin) also involved in oxidative stress response was more reduced in the ssk1Δ mutant (4.2-fold reduction) than the hog1Δ mutants (1.3-fold reductions). These results may explain why the hog1Δ mutants are relatively more resistant to H2O2 than the ssk1Δ mutant.

Example 2

Ergosterol Biosynthesis Genes are Transcriptionally Upregulated by Perturbation of the HOG Signaling Pathway Among genes upregulated by mutation of HOG1 and SSK1 genes, a gene homologous to ERG28 (CNAG_07208) was noticeable since it plays a key role in the fungal sterol biosynthesis. Previous microarray analysis performed in *S. cerevisiae* revealed that expression of ERG28 is tightly correlated with other ergosterol biosynthetic genes. Erg28 is an endoplasmic reticulum (ER) transmembrane scaffold protein, which is essential for the yeast sterol biosynthesis by interacting strongly with Erg27, Erg25, Erg11, and Erg6 and weakly with Erg26 and Erg1. This finding led us to monitor expression patterns of other sterol biosynthetic genes in our array data.

Figure 2:
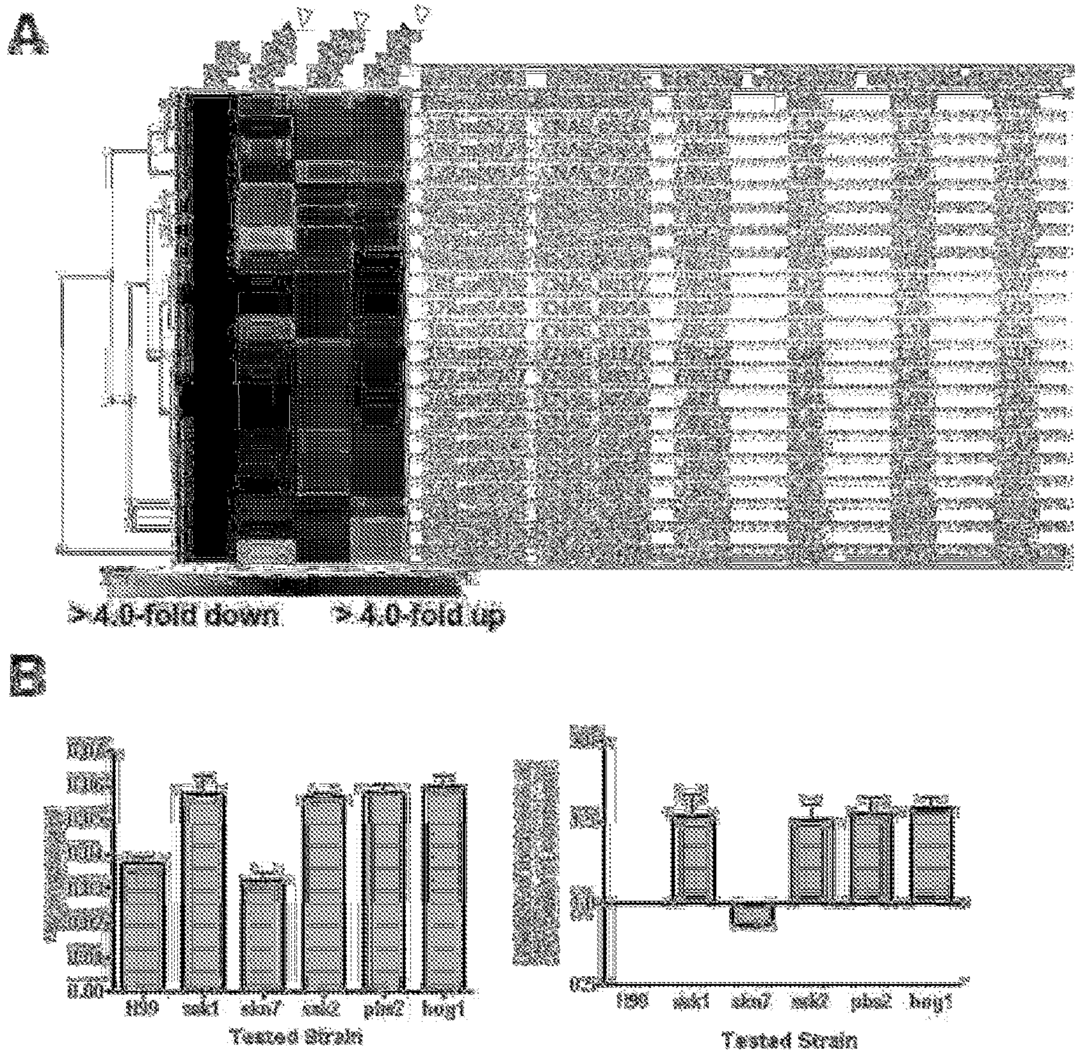
FIG. 2 shows analysis results for induction of ergosterol biosynthesis genes by disturbance of a HOG signal transduction pathway and an ergosterol content in a cell.

FIG. 2A shows the relative expression profiles of ergosterol biosynthesis genes in hog1Δ, ssk1Δ, and skn7Δ mutants compared to WT strain. The fold change is illustrated by a color (see color bar scale) and exact value for each gene was indicated in the table placed right side of the hierarchical clustering diagram. FIG. 2B shows cellular ergosterol contents in WT (H99), skn7Δ (YSB349), ssk1Δ (YSB261), ssk2Δ (YSB264), and hog1Δ (YSB64) mutants. Left and right graphs demonstrate % ergosterol in each strain and relative increase of ergosterol contents compared to WT, respectively. Each bar presents the average from four independent experiments and error bar indicates the standard deviation. Asterisks (*): The ssk1Δ, ssk2Δ, pbs2Δ, and hog1Δ mutants contain significantly higher ergosterol levels compared to the WT (P<0.05, as analyzed by using the Bonferroni multiple comparison test).

Interestingly, a majority of the ergosterol biosynthetic genes were upregulated in hog1Δ and ssk1Δ mutants, but not in the skn7Δ mutant, compared to the wild-type strain (FIG. 2A). Genes, such as ERG11, ERG6, MVD1, ERG5, ERG25, ERG20, and ERG4, were upregulated in both ssk1Δ and hog1Δ mutants while genes, such as ERG27, ERG13, ERG26, ERG10, IDI1, HMG1, and ERG8, were upregulated only in the ssk1Δ mutant (FIG. 2A). In contrast, none of genes were significantly upregulated in the skn7 mutant and indeed some of genes, including ERG13, ERG1, ERG3, ERG7, and ERG2 genes, were downregulated in the skn7Δ mutant (FIG. 2A).

To verify our microarray data, we examined whether increased expression levels of some of the ergosterol biosynthesis genes indeed affect cellular ergosterol contents in the hog1Δ and ssk1Δ mutants (FIG. 2B). In accordance with our microarray data, cellular ergosterol contents were much higher in the hog1Δ and ssk1Δ mutants than WT and skn7Δ mutants (FIG. 2B), suggesting that increased expression of some of ergosterol biosynthetic genes leads to enhanced production of cellular ergosterol. The ssk2Δ (MAPKKK) and pbs2Δ (MAPKK) mutants in the HOG pathway were also found to contain significantly higher levels of cellular ergosterol than WT and skn7Δ mutants (FIG. 2B), further corroborating our array data.

This finding prompted us to investigate the susceptibility of the mutants in the two-component system and the HOG pathway to antifungal drugs that are targeted to the ergosterol biosysnthetic genes or ergosterol itself. First we have examined the susceptibility of the ssk1Δ, skn7Δ, ssk2Δ, pbs2Δ, and hog1Δ mutants made in the serotype A H99 strain background to the polyen antifungal drug, amphotericin B, which binds to ergosterol in the fungal cell membrane and ultimately causes lethality by disrupting the membrane integrity. We hypothesized that increased ergosterol contents observed in ssk1Δ, ssk2Δ, pbs2Δ, and hog1Δ mutants could render them to be hypersensitive to amphotericin B due to the increased number of drug targets.

Figure 3:
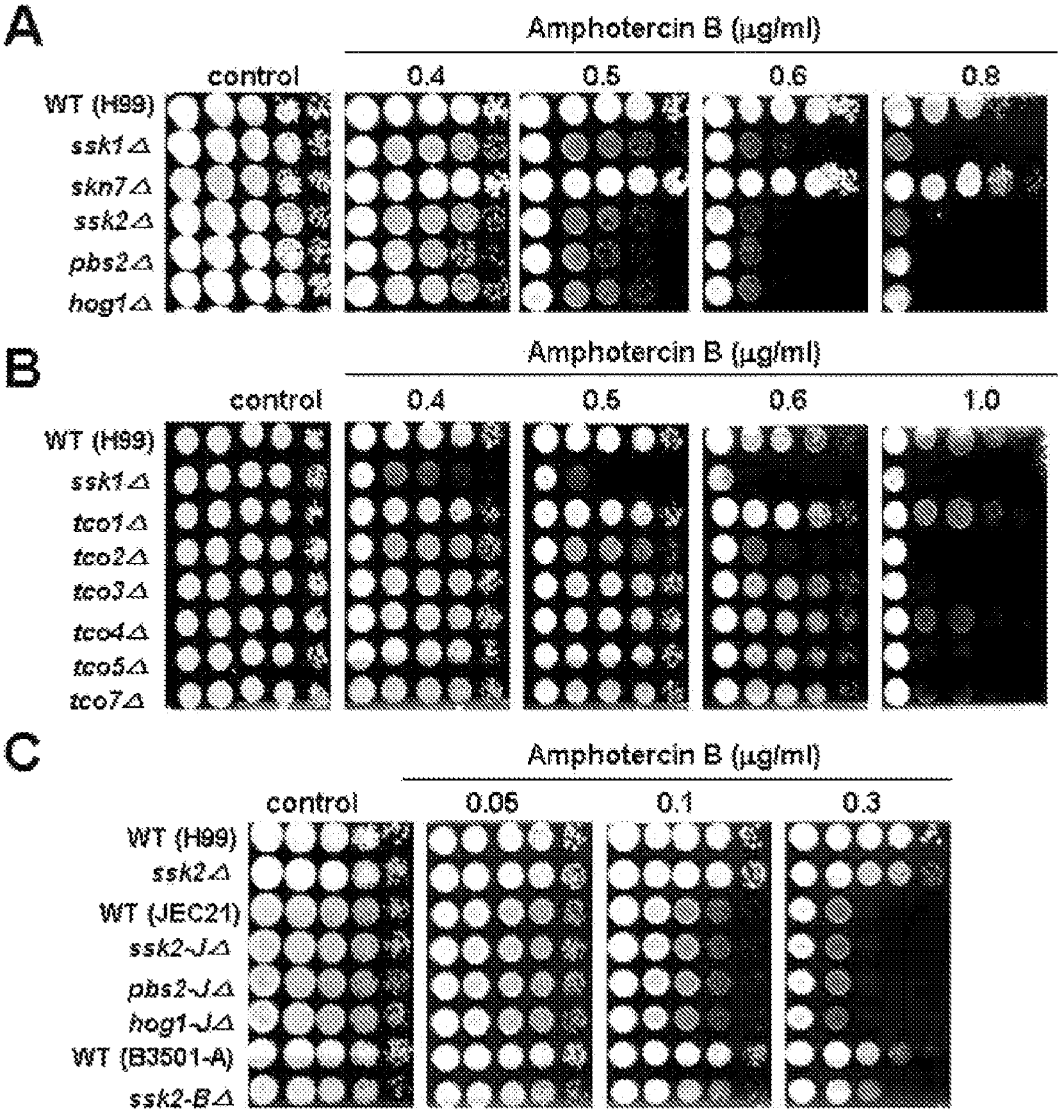
FIG. 3 shows analysis results showing that the inhibition of the HOG pathway gives an elevated antifungal effect with amphotericin B in *C. neoformans;*

FIG. 3 shows analysis results showing that the inhibition of the HOG pathway confers synergistic antifungal effects with amphotericin B in *C. neoformans*. FIG. 3A-3B show pictures photographed after incubation at 30° C. for 72 h of each *C. neoformans* strain spotted on YPD agar containing indicated concentrations of amphotericin B. FIG. 3C shows pictures photographed after incubation at 30° C. for 72 h of *C. neoformans* serotype A strains and serotype D strains spotted on YPD agar containing indicated concentrations of amphotericin B.

Confirming our hypothesis, the ssk1Δ, ssk2Δ, pbs2Δ, and hog1Δ mutants exhibited dramatic hypersensitivity to amphotericin B treatment compared to WT (FIG. 3A), which is in good agreement with the finding that ergosterol contents were significantly higher in the HOG pathway mutants than WT (FIG. 2B). In contrast, the skn7Δ mutant showed WT-levels of resistance to amphotericin B (FIG. 3A), which can be also explained by the previous data showing that cellular ergosterol contents in the skn7Δ mutants are similar to those of WT (FIG. 2B).

We also monitored amphotericin B-susceptibility of *C. neoformans* strains having mutation hybrid sensor kinases (Tco1, Tco2, Tco3, Tco4, Tco5, and Tco7), which act upstream of the Ssk1 response regulator. Previously we have shown that Tco1 and Tco2 play redundant and distinct roles in controlling a subset of Hog1-dependent phenotypes. Here we found that Tco1 and Tco2 play discrete roles in sensing and responding to amphotericin B. Among Tco proteins, only Tco2, which is double hybrid sensor kinases containing two response regulator domains and two histidine kinase domains in a single polypeptide, showed hypersensitivity to amphotericin B (FIG. 3B), indicating that Tco2 is involved in sensing and responding to amphotericin B for conferring the drug-resistance via the HOG pathway. However, the fact that the degree of hypersensitivity observed in the tco2Δ mutant is lesser than the ssk1Δ mutant suggests other possibilities. One possibility is that other unknown receptor/sensors may exist to respond to the amphotericin B. The other possibility is that constitutively phosphorylated Hog1 may repress ergosterol biosynthetic pathway under normal conditions hypersensitivity regardless of the presence of receptors/sensors since Ssk1, Ssk2, and Pbs2, but not Tco2 proteins, are all involved in constitutive phosphorylation levels of Hog1.

To test the hypothesis, we have also examined the amphotericin B sensitivity of other *C. neoformans* strains, such as JEC21 and B3501-A, showing differential Hog1 phosphorylation levels. To support our second hypothesis, the JEC21 strain where Hog1 is not constitutively phosphorylated exhibited hypersensitivity to amphotericin B even more than the ssk2Δ mutant in the H99 strain background (FIG. 3C). In the JEC21 strain background, mutation of SSK2, PBS2, and HOG1 genes did not affect sensitivity to amphotericin B (FIG. 3C). In contrast, the B3501 strain where Hog1 is constitutively phosphorylated, albeit to a lesser extent than in the H99 strain, exhibited higher resistance to amphotericin B than the JEC21 (FIG. 3C). Similar to the H99 strain, mutation of the SSK2 MAPKKK that abolishes the Hog1 phosphorylations increased the amphotericin B sensitivity (FIG. 3C). All these data strongly indicate that constitutively phosphorylated Hog1 represses ergosterol biosynthetic pathway under normal conditions.

To further support this finding, we also examined the susceptibility of the mutants to azole compounds, including triazoles (fluconazole and itraconzaole) and imidazole (ketoconazole), which inhibit the fungal cytochrome P450 enzyme 14α-demethylase and eventually prevent conversion of lanosterol to ergosterol.

Figure 4:
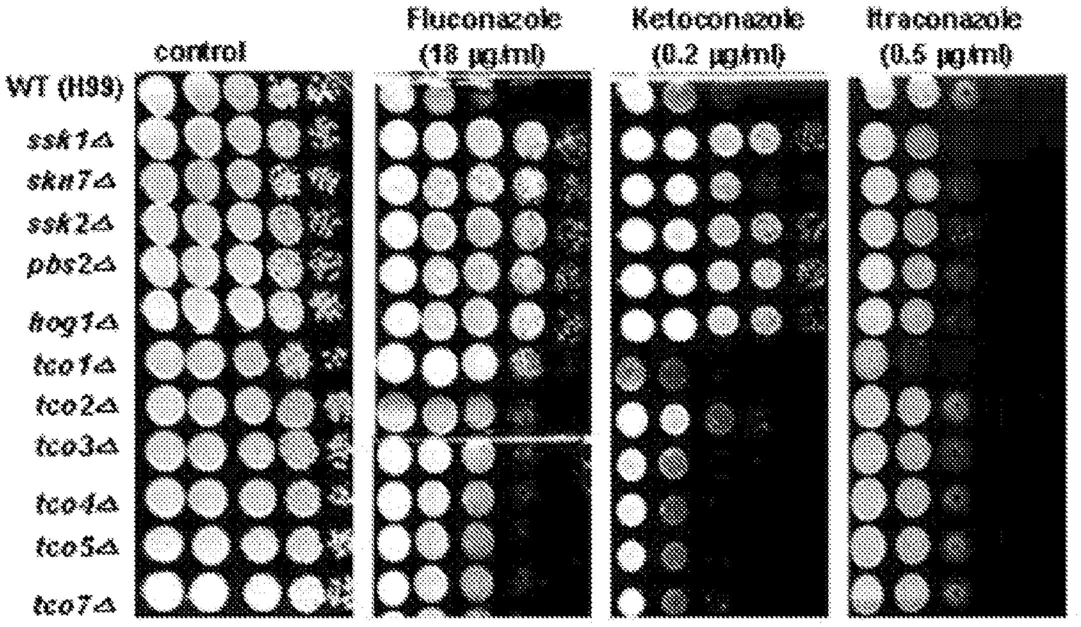
FIG. 4 shows analysis results showing that the inhibition of the HOG pathway gives an antagonistic antifungal effect with respect to some azole drugs in *C. neoformans;*

FIG. 4 shows analysis results showing that the inhibition of the HOG pathway confers antagonistic antifungal effects with some azole drugs in *C. neoformans*. It shows pictures photographed after incubation at 30° C. for 72 h of each *C. neoformans* strain spotted on YPD agar containing indicated concentrations of fluconazole, ketoconazole, and itraconazole.

We had expected that the ssk1Δ and hog1Δ mutants having increased expression of many ergosterol biosynthesis genes, particularly including ERG11, should show higher resistance to azole compounds. The ssk1Δ, ssk2Δ, pbs2Δ, and hog1Δ mutants all exhibited hyper-resistance to fluconazole and ketoconazole, but not to itraconazole (FIG. 4). Interestingly, the skn7Δ mutants also showed higher resistance to fluconazole and ketoconazole than WT (FIG. 4). Among hybrid sensor kinases, only Tco1 and Tco2 display differential sensitivity to azole compounds. Although to a lesser extent than the HOG mutants, the tco2Δ mutant exhibited higher resistance to fluconazole and ketoconazole than WT (FIG. 4). In contrast, the tco1Δ mutant exhibits hypersensitivity to all azole drugs (FIG. 4), indicating that Tco1 may regulate the HOG pathway in *C. neoformans* in an opposite manner to Tco2. In conclusion, inactivation of the HOG pathway increases ergosterol contents by induction of ergosterol biosynthesis genes and therefore confers synergistic effects with amphotericin B treatment, but antagonistic effects with fluconazole and ketoconazole.

Example 3

Finding and Characterizing the Downstream Target Genes Controlled by the HOG Pathway We found ENA1 (serotype A ID: CNAG_00531.2) and NHA1 (serotype A ID: CNAG_01678.2) genes as the downstream target genes controlled by the HOG pathway and performed an additional experiment. Cells excrete H+(proton) out of cell membrane using H+-ATPase pump such as Pma1, thereby playing a role in maintaining membrane potential essential to cell growth in a normal condition. On the contrary, potassium ion (K+), an ion useful to cell growth, flows into cells using K+ influx pump such as Trk1/Trk2. Na+, unlike K+, is classified as a toxic ion. When high concentration of Na+ is present in a cell, it should be excreted via efflux pump. Since K+ also has toxicity when it presents in high concentration, an efflux pump is needed. These are Ena1 and Nha1 which play a role as an efflux pump for Na+ and K+.

Figure 5:
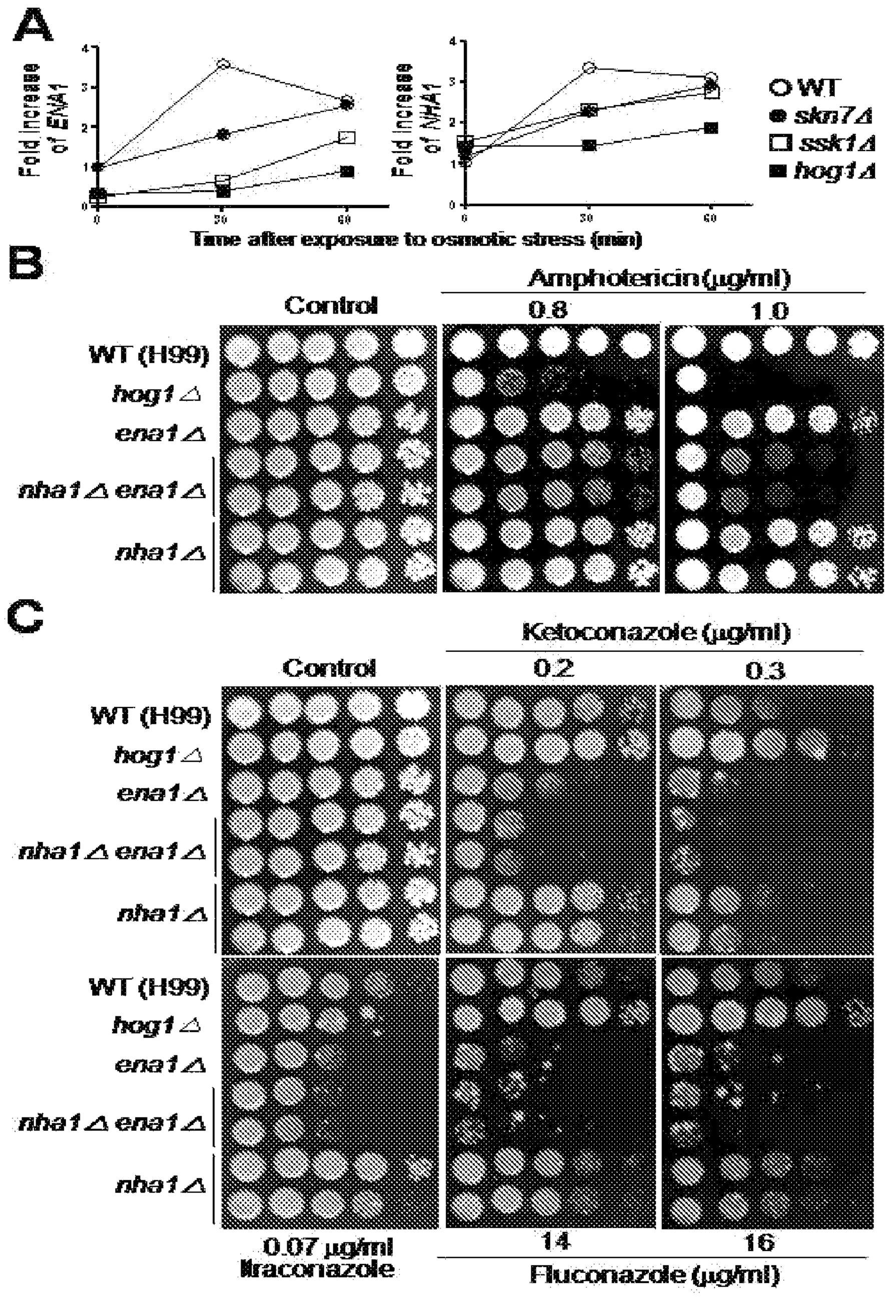
FIG. 5 shows analysis results showing that gene coding for an efflux pump of $Na^+$ and $K^+$, ENA1 and NHA1, are lower-system target genes regulated by the HOG pathway, and the inhibition of these genes gives high sensitivity to polyene-based drugs and azole-based drugs.

The result showed that the two genes coding for the two efflux pumps are controlled by the HOG pathway. As shown in FIG. 5A, when the WT, skn7Δ, ssk1Δ and hog1Δ mutant strains were exposed to osmotic stress, the expression level of ENA1 and NHA1 was dependent on the deletion mutant of the HOG pathway genes.

Thus, in order to identify a characteristic of two genes, we prepared deletion mutant of each gene and double mutant (ena1Δ nha1Δ) eliminating both two genes. And then, we examined sensitivity of the mutants to the polyene-based antifungal agent such as amphotericin B (AmpB), and the azole-based antifungal agent such as fluconazole, ketoconazole and itraconazole. The ena1Δ and nha1Δ mutants did not show high sensitivity to the AmpB. However, surprisingly, the ena1Δ nha1Δ double mutant showed considerably increased sensitivity to AmpB (FIG. 5B). Although lower sensitivity than hog1Δ, high AmpB sensitivity of the ena1Δ nha1Δ suggests that these two efflux pumps play an important role in the polyene-based drug resistance. It is more noteworthy that ena1Δ and ena1Δ nha1Δ mutants also show high sensitivity to the azole-based drugs (FIG. 5C). It is a distinguished from the hog1Δ mutant which has high resistance to the azole-based antifungal agents and verify that the inhibitors simultaneously or independently targeting Ena1 and Nha1 may exhibit very high antifungal activities when used in combination with the polyene- or azole-based antifungal agents.

Example 4

Comparative Transcriptome Analysis of *C. neoformans* ras1Δ, aca1Δ, gpa1Δ, cac1Δ, and pka1Δ pka2Δ Mutants To compare the downstream signaling network of Ras1-, Aca1-, and Gpa1-dependent signaling pathways, we performed comparative transcriptome analysis of the serotype A wild-type (WT, H99) strain, ras1Δ, aca1Δ, gpa1Δ, cac1Δ, and pka1Δ pka2Δ mutants by employing DNA microarray analysis as described in Materials and Methods. For basic validation of our array quality, we checked expression levels of the RAS1, ACA1, GPA1, CAC1, PKA1, and PKA2 genes in our array data. The relative expression levels of RAS1, ACA1, GPA1, CAC1, PKA1, and PKA2 in each corresponding mutant were very low compared to those in the wild type strain (0.08, 0.03, 0.09, 0.06, 0.07, and 0.12, respectively) (FIG. 6A), which supported the quality of our array.

Figure 6:
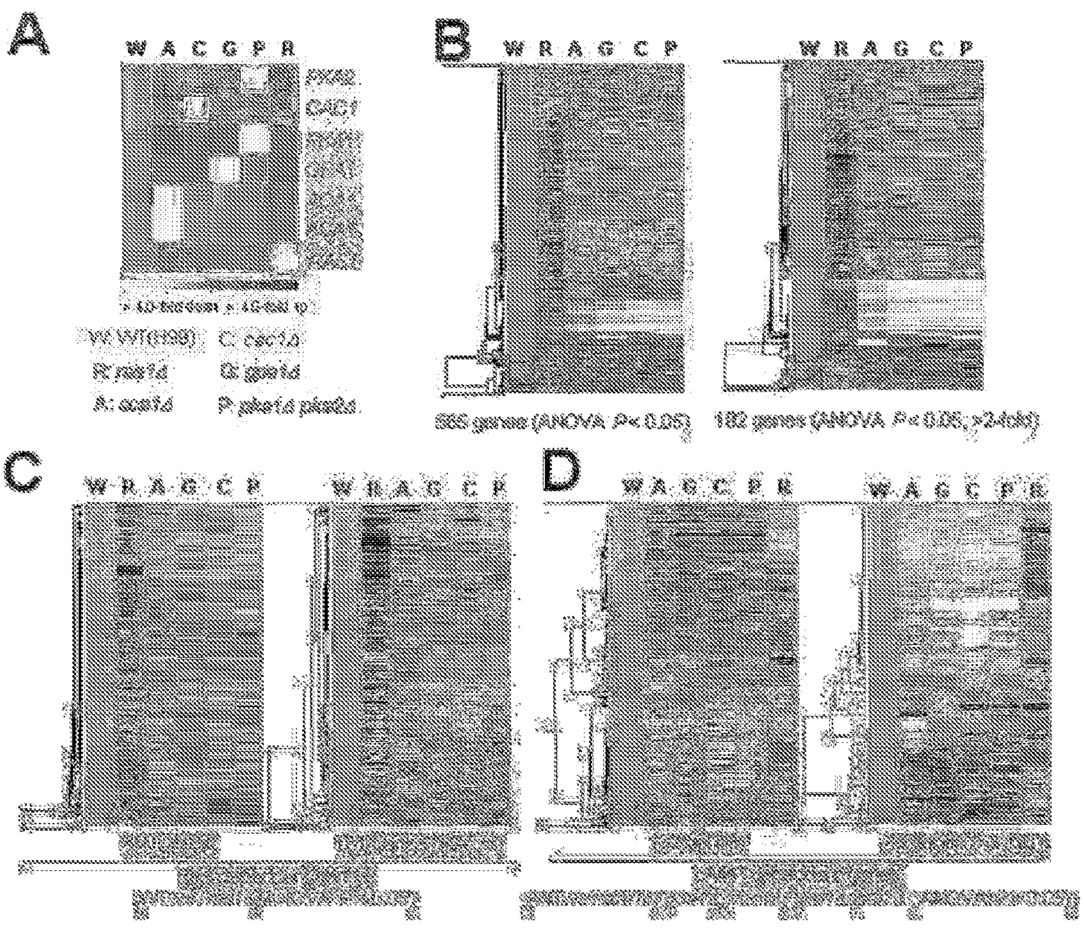
FIG. 6 shows analysis results for transcripts of ras1Δ, aca1Δ, gpa1Δ, cac1Δ, and pka1Δ pka2Δ deletion mutants of *C. neoformans* (fold change is expressed by color)

From total 7,936 genes monitored by this DNA microarray, 565 genes exhibited differential expression patterns in the Ras- and cAMP mutants at statistically significant levels compared to the wild type strain (ANOVA test, $P<0.05$) (FIG. 6B). The hierarchical clustering analysis of the Ras- or cAMP-dependent genes revealed several important facts. First, the transcriptome patterns governed by the Ras1-signaling pathway were distinct from those controlled by the cAMP/PKA-signaling pathway. The statistical analysis indicated that basal expression levels of total 400 genes changed significantly in the ras1Δ mutant compared to the WT, whereas expression levels of 132 genes changed significantly in the aca1Δ, gpa1Δ, cac1Δ, and pka1Δ pka2Δ mutants (FIGS. 6C and 6D). Besides the number of genes regulated, the expression patterns of a majority of the Ras1-dependent genes were also distinguished from those of the cAMP-dependent genes, which supported that the Ras1-signaling pathway is largely independent of the cAMP-signaling pathway in *C. neoformans*. Second, the aca1Δ and gpa1Δ mutants showed transcriptome patterns similar to those of the cac1Δ and pka1Δ pka2Δ mutants, indicating that Aca1 and Gpa1 are the two major signaling modulators of the cAMP-signaling pathway (FIG. 6D). However, there were a small group of genes whose expression is differentially regulated between the aca1Δ and gpa1Δ mutants. This indicates that Aca1 and Gpa1 could have other minor signaling branches (FIG. 6D). As expected, the cac1Δ mutant exhibited transcriptome patterns almost identical to that of the pka1Δ pka2Δ mutant, further suggesting that Pka1 and Pka2 are necessary and sufficient protein kinase downstream of the adenylyl cyclase in *C. neoformans* (FIG. 6D).

Figure 7:
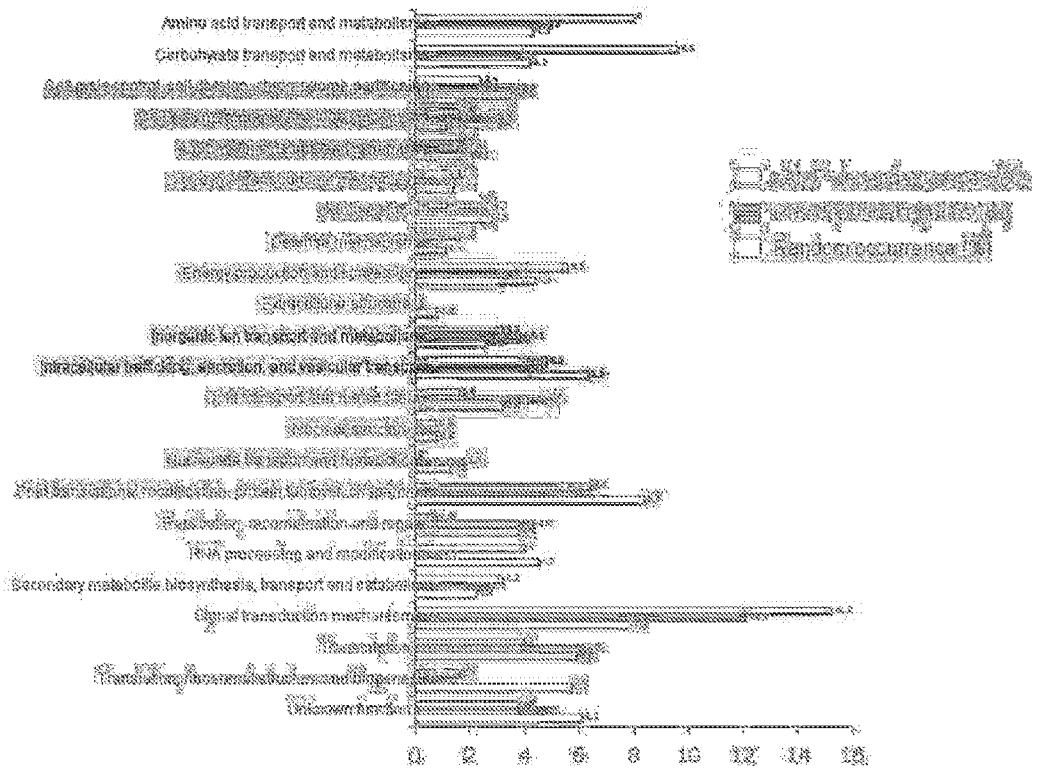
FIG. 7 shows functional categories of genes differently regulated by the ras1Δ, aca1Δ, gpa1Δ, cac1Δ, and pka1Δ pka2Δ deletion mutants of *C. neoformans;*

The genes regulated by the Ras- and cAMP-signaling pathways cover a wide variety of cellular functions (FIG. 7). The cAMP-signaling dependent genes were over-represented for those involved in signal transduction mechanisms (15.2%), carbohydrate transport and metabolism (9.6%), and amino acid transport and metabolism (8.0%). These findings were rather expected results since the cAMP-pathway is one of central signal transduction cascades that regulate growth, differentiation, and virulence of *C. neoformans* and is known to sense glucose and amino acids (Bahn et al., 2004, Xue et al., 2006). Similarly, genes involved in signal transduction mechanisms were most over-represented in the ras1Δ mutant (12.1%) (FIG. 7). In contrast to the cAMP-pathway, however, genes involved in cell wall/membrane/envelope biogenesis were over-represented (2.9%), which implies that Ras1 may be implicated in maintenance of cell wall integrity.

Figure 8:
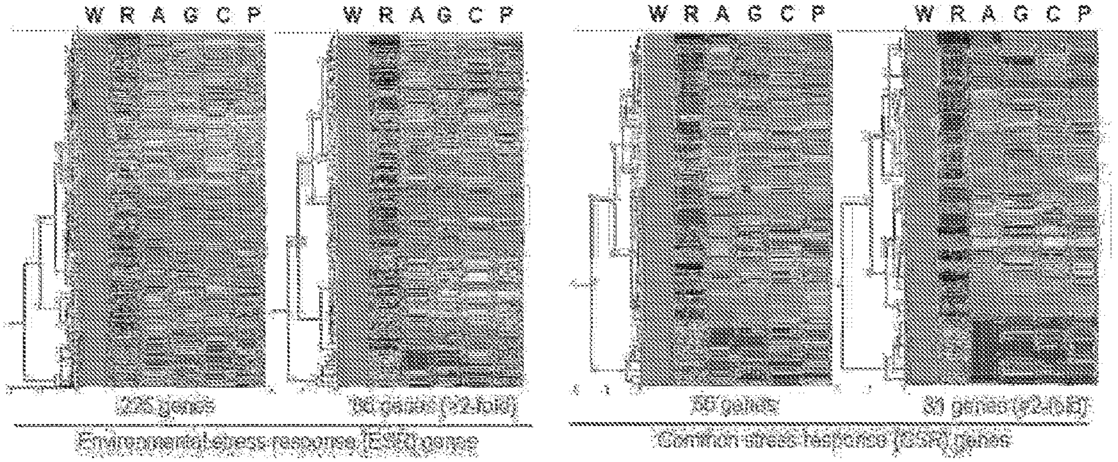
FIG. 8 shows regulation of a significant ratio of Ras- and cAMP-dependent genes by environmental stress.

Among the Ras- and cAMP-dependent genes, a significant proportion of them were found to be environmental stress-regulated (FIG. 8). Our prior transcriptome analysis discovered a number of ESR (Environmental Stress Regulated) genes in *C. neoformans* (Ko et al., 2009). A total of 1,959 genes were found to be more than 2-fold up or downregulated in response to either of osmotic stress, oxidative stress, or antifungal drug (fludioxonil) treatment (Ko et al., 2009). Interestingly, our current array analysis revealed that a subset of the ESR genes (a total of 225 ESR genes) exhibited significant changes in expression levels in either the ras1Δ or cAMP mutants compared to the wild-type strain (ANOVA test, $P<0.05$) (FIG. 8). Among these, eighty-six ESR genes showed more than 2-fold induction or reduction in the mutants (FIG. 8). Furthermore, a total of 55 CSR (Common Stress Response) genes were found to be differentially regulated (ANOVA test, $P<0.05$) and 31 genes of them exhibited more than 2-fold induction or reduction in the mutants (FIG. 2B). The major proportion of the Ras- or cAMP-pathway-dependent ESR and CSR genes did not have any other homologs with significant homology (Table S6). Nevertheless, these results implied that the Ras- and cAMP-signaling pathways be implicated in diverse stress response of *C. neoformans.*

Example 5

Identification of the Ras- or cAMP-Dependent Genes in *C. neoformans*

Next we further investigated individual Ras1- and cAMP-dependent genes identified by our transcriptome analysis.

Among the selected 161 Ras-dependent genes (2-fold cutoff, FIG. 6C), a majority of them (101 genes, 63%) do not have any orthologs in other fungi (Table S4), which indicated that *C. neoformans* contains a unique set of Ras-dependent genes. Among the evolutionary conserved Ras-dependent genes, three genes, PXL1, RDI1, and BEM3, whose orthologs are known to be involved in regulation of Rho-GTPase Cdc42 in *S. cerevisiae*, were notable since the Ras1-Cdc24 signaling pathway has been reported to be controlled by one of three Cdc42 homologues in *C. neoformans* (Nichols et al., 2007). RDI1 and BEM3 encode Rho-GDP dissociation inhibitor and Rho-GTPase activating protein, respectively (Price et al., 2008, Zheng et al., 1994). Notably, in a good agreement with the role of Ras1 in genotoxic stress response of *C. neoformans* (FIG. 4), a number of genes involved in regulation of DNA damage repair were identified as Ras-dependent genes. These include RNR2/RNR3 (Ribonucleotide-diphosphate reductase), RAD3 (DNA helicase, a subunit of nucleotide excision repair factor 3), RAD14 (a subunit of nucleotide excision repair factor 1), MSH6 (a protein required for mismatch repair), MND1 (a protein required for recombination and repair of DNA double strand breaks), and DNA2 (ATP-dependent nuclease). Finally, several genes, CHS1 (Chitin synthase 1), CDA2 (Chitin deacetylase), BGL2 (glucan 1,3-β-glucosidase), and GSC2 (Glucan synthase), involved in governing cell wall integrity were also identified as Ras-dependent genes 6, which further supported the role of Ras1 in maintaining cell wall integrity of *C. neoformans.*

Figure 9:
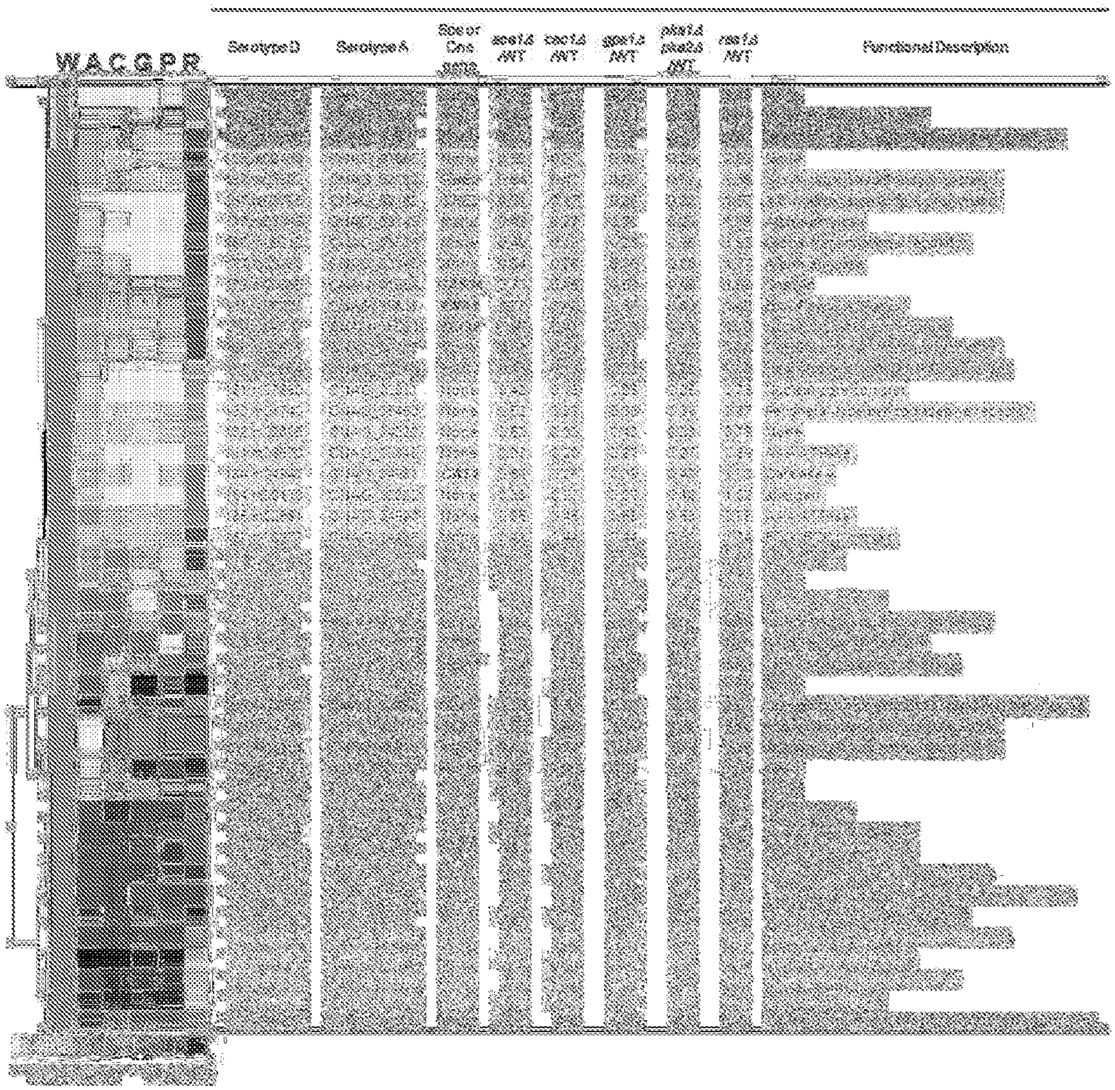
FIG. 9 shows an identification result of a cAMP-signal transduction pathway dependent gene in *C. neoformans;*

The statistical comparison of transcriptome data obtained from the cAMP mutants (aca1Δ, gpa1Δ, cac1Δ, and pka1Δ pka2Δ) with that from the WT strain (ANOVA, $P<0.05$) identified 163 genes (FIG. 6C). Among these, 38 genes exhibited more than 2-fold induction or reduction in the cAMP mutants, except CAC1, ACA1, PKA1, and GPA1 (FIG. 9). A majority of the cAMP-dependent genes (31 genes, 81%) do not have any known function in *C. neoformans* or orthologs in *S. cerevisiae*, which indicated that *C. neoformans* contains a unique set of cAMP-dependent genes similarly to the Ras-dependent genes. This observation further corroborates that *C. neoformans* cAMP mutants have unique phenotypic characteristics that have not been observed in other fungi. Five cAMP-dependent genes (GRE2, ENA1, HSP12, CAT1, and PKP1) in *C. neoformans* appear to be evolutionarily conserved in other fungi. Interestingly, the GRE2, ENA1, and HSP12 genes are known to be transcriptionally regulated by environmental stress in *S. cerevisiae*. In *C. neoformans*, it has been recently reported that Ena1 not only controls osmotic stress under carbon starvation condition (Ko et al., 2009), but also is required for survival in alkaline pH and in vivo virulence (Idnurm et al., 2009). The GRE2 (genes de respuesta a estres, stress-responsive gene), a homolog of mammalian 3-β-hydroxysteroid dehydrogenase, is strongly induced in response to a variety of stresses, including osmotic and oxidative stress, upon binding of HOG-dependent Sko1 transcription factor to CRE (cAMP response element) in the promoter region in *S. cerevisiae* (Garay-Arroyo & Covarrubias, 1999, Rep et al., 2001). The heat shock protein HSP12 (03143) is a small hydrophilic protein whose expression is also induced by diverse stresses and regulated by both HOG and cAMP signaling pathways (Varela et al., 1995). Here we named this gene as HSC1 (HSP12-like *C. neoformans* gene 1, 03143).

Example 6

Inhibition of the Ras and cAMP-Signaling Pathway Increased Polyene Sensitivity

Gre2 is involved in regulation of some of ergosterol biosynthesis genes, including ERG6, ERG10, and ERG19/MVD1 (Warringer & Blomberg, 2006). Furthermore, GRE2 is reported to be one of six genes whose expression increased with resistance to amphotericin B (AmpB) in *S. cerevisiae* (Anderson et al., 2009). Therefore, we examined whether the *C. neoformans* Ras- and cAMP-mutants are more susceptible to AmpB treatment than WT.

Figure 10:
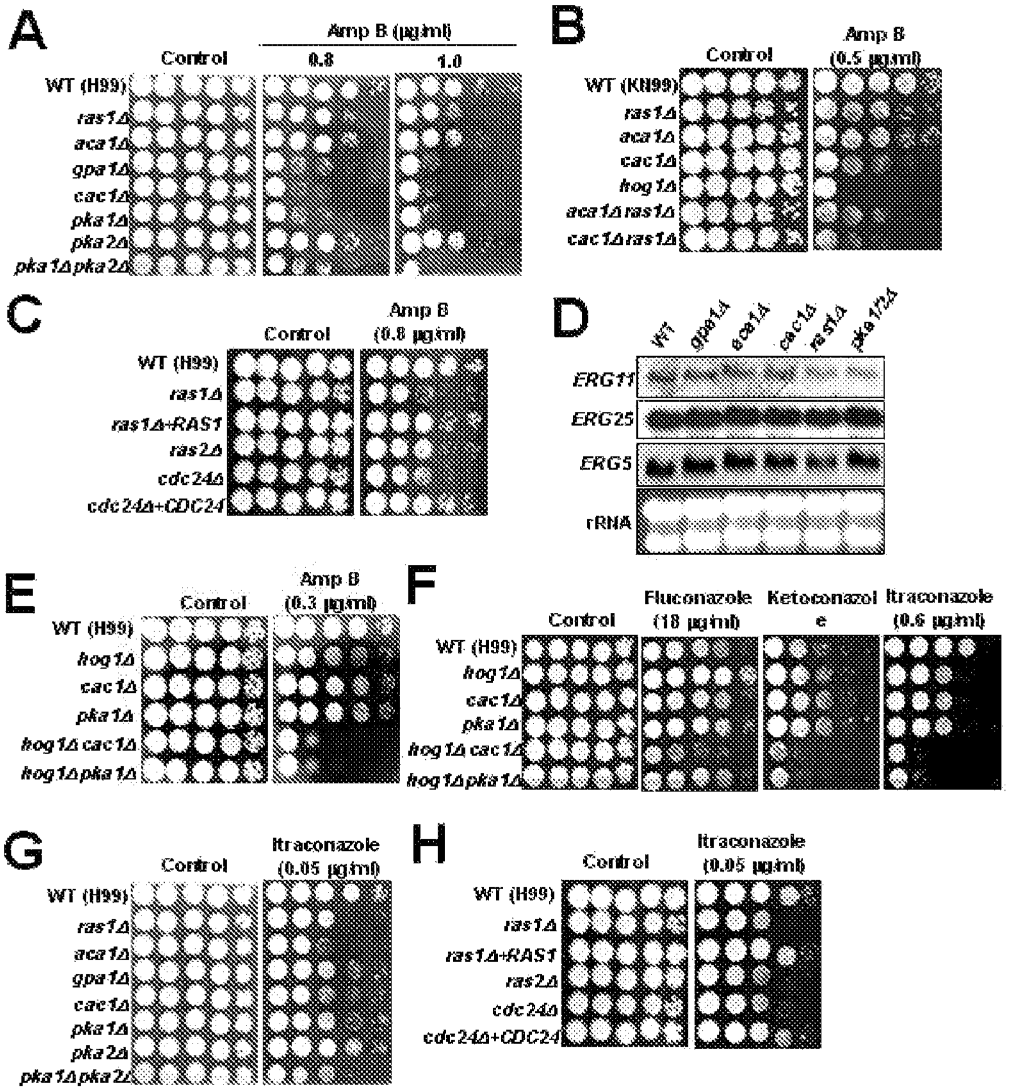
FIG. 10 shows analysis results showing that the inhibition of the Ras- and cAMP-signal transduction pathways increases a sensitivity to polyene-based or azole-based (itraconazole) antifungal agent, independent of ergosterol biosynthesis.

As shown in FIG. 10, the ras1Δ mutant showed higher susceptibility to AmpB than WT whereas the aca1Δ mutant exhibited slightly higher AmpB susceptibility (FIG. 10A). The ras1Δ aca1Δ double mutant exhibited higher AmpB-sensitivity than each single mutant (FIG. 10B), indicating that Ras1 and Aca1 redundantly or independently control AmpB sensitivity. Cdc24 appears to work downstream of Ras1 for regulation of the polyene drug resistance (FIG. 10C). Interestingly, the ras2Δ mutant was also slightly more sensitive to AmpB than WT, indicating that both Ras proteins control resistance to polyene drugs in *C. neoformans.*

Notably, the gpa1Δ and cac1Δ mutants showed much higher AmpB-sensitivity than WT and even than the ras1Δ or aca1Δ mutant (FIG. 10A). Downstream of the Cac1 adenylyl cyclase, the pka1Δ mutant, but not the pka2Δ mutant, showed increased susceptibility to AmpB (FIG. 10A), strongly indicating that the Gpa1-Cac1-Pka1 signaling cascade is one of signaling circuits to control the polyene drug sensitivity. The ras1Δ cac1Δ double mutant exhibited even higher AmpB susceptibility than each single mutant (FIG. 10B), indicating that the Ras- and Gpa1-Cac1-Pka1 pathways are independently involved in AmpB susceptibility. The ras1Δ and ras1Δ cac1Δ mutants generated in MATa background (KN99 strain) exhibited the same phenotypes (data not shown).

To address whether the involvement of the Ras- and cAMP-pathways in the polyene sensitivity is related to the levels of ergosterol biosynthesis, we checked expression levels of ergosterol biosynthesis genes in the mutants from our array data. Interestingly, none of ergosterol biosynthesis genes, except ERG3 and ERG25 (<less than 2-fold), exhibited significant expression changes in the ras1Δ, aca1Δ, gpa1Δ, cac1Δ, or pka1Δ pka2Δ mutants compared to WT (Table S2 and S3). Northern blot analysis showed that expression levels of the ERG3 and ERG25 genes in the mutants were not significantly different from those of WT (FIG. 10D). We also checked cellular ergosterol contents in the Ras- and cAMP-mutants and found that cellular ergosterol contents were not significantly increased in the Ras- and cAMP-mutants compared to WT whereas the hog1Δ mutant has increased ergosterol contents as previously reported (data not shown) (Ko et al., 2009). Furthermore, expression levels of ERG11 in the ras1Δ and cAMP mutants were not significantly different from those of WT (FIG. 10D). Supporting this finding, the gpa1Δ, cac1Δ, pka1Δ, pka2Δ, and pka1Δ pka2Δ mutants were nearly as resistant to fluconazole, which target to the fungal cytochrome P450 enzyme 14α-demethylase and inhibit conversion of lanosterol to ergosterol, as the WT strain (data not shown). All these data strongly implied that the Ras and cAMP-signaling pathway independently influence the polyene sensitivity without affecting ergosterol biosynthesis.

We have found in Examples 1 to 3 that the HOG pathway controls ergosterol biosynthesis of *C. neoformans* under unstressed conditions and the HOG pathways mutants are hyper-sensitive to AmpB, but hyper-resistance to fluconazole because of the increased cellular ergosterol contents in the mutants (Ko et al., 2009). Therefore, it is easily conceivable that the HOG and cAMP pathways influence the polyene sensitivity in different manners. Supporting this, we found that the hog1Δ cac1Δ and hog1Δ pka1Δ double mutants were even more sensitive to AmpB than the hog1Δ, cac1Δ, or pka1Δ single mutant (FIG. 10E). Unexpectedly, the hog1Δ cac1Δ double mutants also exhibited hypersensitivity to various azole drugs, such as fluconazole, ketoconazole, and itraconazole (FIG. 10F). Interestingly, the ras1Δ, aca1Δ, gpa1Δ, cac1Δ, and pka1Δ mutants all showed increased sensitivity to itraconazole (FIG. 10G). Particularly, both Ras1 and Ras2 appear to be involved in itraconazole susceptibility in a manner dependent of Cdc24 (FIG. 10H). Taken together, these date indicate that the HOG pathway and cAMP-signaling pathways independently control polyene and azole drug susceptibility.

One of key findings made by this study was that the Ras- and cAMP-signaling pathways controlled the polyene- and azole-based drug susceptibility in *C. neoformans*. Both Ras1 and Ras2 appeared to be involved in polyene susceptibility by using Cdc24 as a downstream effector. Interestingly, the ras1Δ aca1Δ mutant was also hypersensitive to amphotericin B, indicating that the Ras1 and Aca1 may play a minor role in susceptibility to the polyene drugs. It could be possible that perturbed action cytoskeleton regulation and cell wall integrity by ras1 and aca1 mutation makes cell more susceptible to the polyene drugs.

The cAMP-signaling pathway was even more significantly involved in polyene sensitivity than the Ras-signaling pathway. Mutation of the GPA1, CAC1, and PKA1, rendered *C. neoformans* cells to be hypersensitive to the polyene drugs, such as amphotericin B (AmpB). We recently reported that perturbation of the HOG pathway also renders *C. neoformans* cells to be hypersensitive to AmpB (Ko et al., 2009). However, the cAMP and HOG pathways appear to work differently for modulation of the polyene drug susceptibility. Inhibition of the HOG pathway, but not the cAMP pathway, increases ergosterol biosynthesis, which enhances the polyene drug susceptibility and azole drug resistance (Ko et al., 2009). Furthermore, the hog1Δ mutant exhibited higher sensitivity to AmpB than the cAMP mutants.

Example 7

Characterization of the cAMP-Dependent Genes in *C. neoformans*

We also addressed the role of the cAMP-dependent genes and in diverse stress response and antifungal drug susceptibility of *C. neoformans* due to the involvement of the cAMP-pathway in the process that we discovered in this study.

Figure 11:
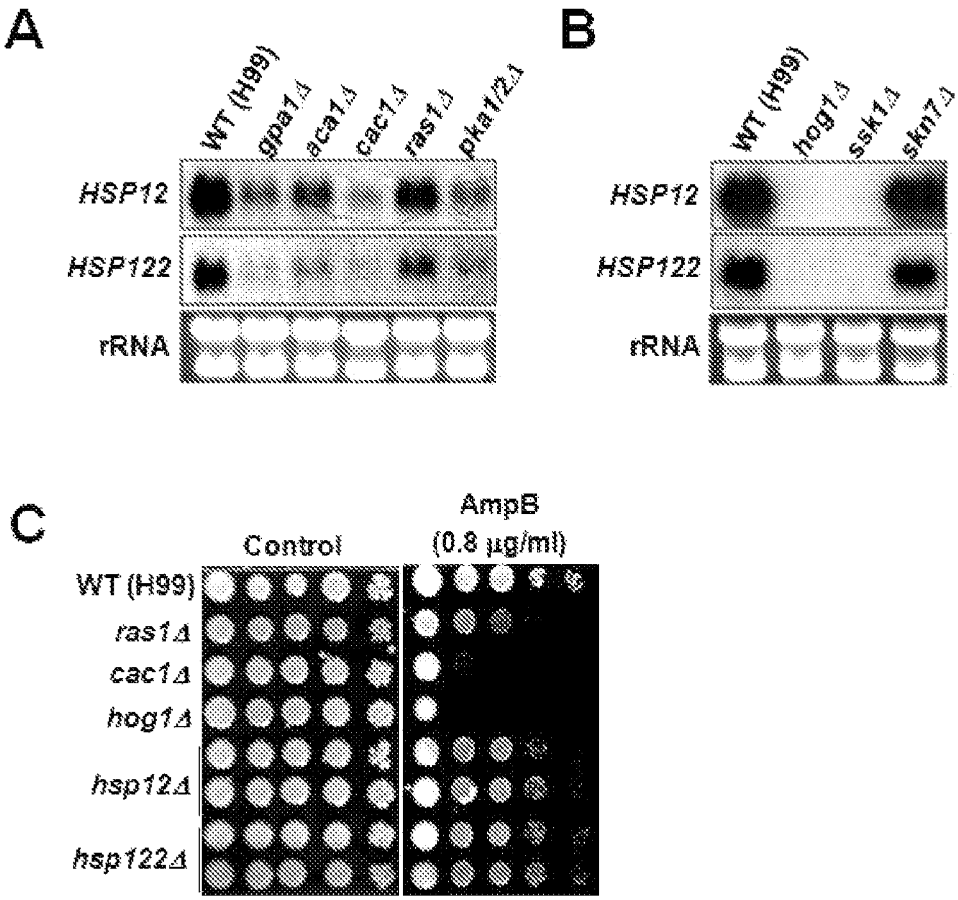
FIG. 11 shows analysis results showing that the expression of HSP12 and HSP122 is up-regulated by the cAMP- and HOG-signal transduction pathways, and increases sensitivity to polyene-based antifungal agents by hsp12Δ and hsp122Δ deletion mutants.

Hypersensitivity of the cAMP mutants to the polyene drug appeared to be partly contributed by decreased expression of the two heat shock proteins Hsp12 (H99 gene ID: CNAG_03143.2), *C. neoformans* homologs of HSP12, and Hsp122 (H99 gene ID: CNAG_01446.2) (FIG. 11).

Interestingly, however, the hsp12Δ or hsp122Δ mutant exhibited slightly higher susceptibility to AmpB than WT, although the cac1Δ mutant was more sensitive to AmpB than the hsp12Δ or hsp122Δ mutant (FIG. 11A). Therefore, it was conceivable that decreased expression of HSP12 or HSP122 contributes to hypersensitivity of the cAMP mutants to AmpB.

To further characterize the regulatory mechanism of HSP12 and HSP122, we performed Northern blot analysis to confirm that the cAMP-signaling pathway modulated expression of the HSP12 and HSP122 genes. In *S. cerevisiae*, HSP12 is not expressed under unstressed, glucose-rich condition, but is induced in response to environmental stresses (Praekelt & Meacock, 1990, Siderius et al., 1997). Unexpectedly, however, the HSP12 and HSP122 genes were found to be highly expressed genes in the WT strain under unstressed, glucose-rich condition (FIG. 11A). In a good agreement with the microarray data, HSP12 and HSP122 expression was significantly downregulated in the cAMP mutants, including gpa1Δ, cac1Δ, and pka1Δ pka2Δ mutants (FIG. 11A). In the aca1Δ and ras1Δ mutants, expression levels of the HSP12 and HSP122 genes were only slightly affected (FIG. 11A). These data not only confirmed our microarray data, but also indicated that HSP12 and HSP122 were positively regulated by the cAMP-signaling pathway.

Interestingly our previous array analysis showed that HSP12 and HSP122 may also be under control of the HOG pathway. HSP12 and HSP122 expression levels were considerably low in the hog1Δ and ssk1Δ, but not in the skn7Δ mutant (FIG. 11B). To confirm this, we performed Northern blot analysis and found that expression levels of HSP12 and HSP122 were very high in the WT and skn7Δ mutants, but was undetectable in the hog1Δ and ssk1Δ (FIG. 11B). All these data strongly indicated that the HSP12 and HSP122 gene was co-regulated by the cAMP and HOG signaling pathways.

As discussed in the above, hypersensitivity of the cAMP mutants to the polyene drug appeared to be partly contributed by decreased expression of the heat shock protein Hsp12 and Hsp122. In *S. cerevisiae*, Hsp12 plays a role in stabilizing the plasma membrane as a cell wall plasticizer and water replacement molecules (Sales et al., 2000, Shamrock & Lindsey, 2008) and therefore is involved in maintaining cell wall integrity under the stressful conditions in *S. cerevisiae* (Shamrock et al., 2009). Therefore, the hsp12Δ mutant is unable to grow in the presence of a cell wall destabilizer, Congo red (Motshwene et al., 2004). Therefore, perturbation of the cAMP-signaling pathway reduces basal expression levels of Hsp12, which subsequently weakened cell wall integrity and membrane plasticity of *C. neoformans*. Similarly, hypersensitivity of the HOG pathway mutants to the polyene drug in part results from decreased expression of HSP12. However, since the cac1Δ mutant is much more sensitive to AmpB than the hsp12Δ mutant, other factors, except ergosterol biosynthesis, may affect resistance to the polyene drug. Supporting this, the hog1Δ cac1Δ or hog1Δ pka1Δ double mutant exhibited even higher polyene drug sensitivity than each single mutant, which indicated that the two pathways play an independent role in the polyene drug susceptibility. Notably, the double mutation of the HOG1 and CAC1 genes renders *C. neofor-*

*mans* cells to be hypersensitive to most of azole drugs, including fluconazole, ketoconazole, and itraconazole, with unknown reasons.

In any case, modulation of each Ras-, cAMP/PKA-, and HOG-signaling pathway (or combination of them) may provide a novel antifungal therapeutic approach in combination with polyene and azole drugs. Simultaneous inhibition of the cAMP and HOG pathways when treated with polyene drugs such as amphotericin B could be one of the most powerful combination therapy for treatment of cryptococcosis.

What is claimed is:

1. A method of screening a candidate agent for improving the fungal killing efficacy of an ergosterol-binding antifungal agent for *Cryptococcus neoformans*, comprising:

contacting Ssk1 protein of *Cryptococcus neoformans* with the candidate agent;

measuring whether the candidate agent inhibits an activity of Ssk1 protein;

selecting a candidate agent which inhibits Ssk1 activity;

determining whether fungal killing efficacy for *Cryptococcus neoformans* is improved for the ergosterol-binding antifungal agent when administered together with the selected candidate agent which inhibits Ssk1 activity, compared with sole treatment with the ergosterol-binding antifungal agent; and further selecting a candidate agent which is capable of improving the fungal killing efficacy of the ergosterol-binding antifungal agent.

2. The method of claim 1, wherein the ergosterol-binding antifungal agent is a polyene-based antifungal agent.

3. The method of claim 2, wherein the polyene-based antifungal agent is at least one selected from the group consisting of amphotericin B, natamycin, rimocidin, filipin, nystatin, and candicin.

4. The method of claim 2, wherein the polyene-based antifungal agent is amphotericin B.

* * * * *

SEQUENCE LISTING

```
<160> NUMBER OF SEQ ID NOS: 30

<210> SEQ ID NO 1
<211> LENGTH: 1309
<212> TYPE: PRT
<213> ORGANISM: Cryptococcus neoformans
<220> FEATURE:
<221> NAME/KEY: PEPTIDE
<222> LOCATION: (1)..(1309)
<223> OTHER INFORMATION: amino acid sequence of SSK1 serotype A H99
      strain

<400> SEQUENCE: 1

Met Trp Gly Ser Asn Ala Ser Ile Ala Ala Ser Glu Ser Thr Asp Ser
1               5                   10                  15

Leu Ser Pro Ala Pro Ser Gln Ser Ala Ala Val Glu Phe Pro Leu Pro
            20                  25                  30

Val Ser Ser Arg Pro Ser Leu Thr Ser Ala Ala His Pro Ser Gln Met
        35                  40                  45

Ser Ala Ser Ser Ser Ser Thr Ser Ser Gln Pro Leu Phe Asp Trp Arg
    50                  55                  60

Ile Pro Lys Pro Thr Ser Pro Arg Thr Arg Met Asp Pro Phe Asp Thr
65                  70                  75                  80

Phe Asp Pro Val Ser Ser Ser Ser Glu Asp Asp Pro Val Pro Gln Glu
                85                  90                  95

Ser Arg Arg Ala Gly His Gln Arg Ser Val Thr Asp Pro Leu Leu Arg
            100                 105                 110

Asp Gly Gln Pro Leu Asp Met Glu Phe Thr Thr Ala Gly Pro Pro Ile
        115                 120                 125

Gln Ser Tyr Asp Phe Glu Gln Pro Pro Thr Phe Ser Arg Thr Leu Ser
    130                 135                 140

Ser Pro Leu Pro Ala Lys Val Gly Ser Leu Arg His Pro Met Pro Phe
145                 150                 155                 160

Thr Ile Asp Asp Leu Ser Ser Arg Asn Val Asn Ser Thr His Arg Pro
                165                 170                 175

Gln Pro Thr Thr Pro Leu His Ser Ile Ser Val Glu Leu Ala Asp Ser
            180                 185                 190

Leu Gln Ser Ala Ile Gln Thr Leu Leu His Leu Ser Pro Pro His Leu
        195                 200                 205

Leu Asp Asn Ala Lys Glu Gln Tyr Ser Gly Cys Thr Val Gln Ile Pro
    210                 215                 220

Ala Thr Ser Leu Ser Ala Leu Leu Thr Ser Met Arg Gly Leu Asn Phe
225                 230                 235                 240

Leu Ser Ala His Ala Glu Glu Leu Val Asp Met Ser Ala Arg Gly Asp
                245                 250                 255

Pro Pro Val Leu His Gln Glu Asp Phe Asp Val Gly Glu Leu Leu Gln
            260                 265                 270

Asn Val Ala Asp Met Leu Ser Gly Glu Ala Ala Glu Lys Arg Ile Asp
        275                 280                 285

Phe Val Leu Phe His Gly Asp Val Ala Met Arg His Val Ser Val Tyr
    290                 295                 300
```

-continued

```
Gly Asp Ser Asp Gly Ile Ser Tyr Thr Leu Ser His Val Ile Arg Gln
305                 310                 315                 320

Ile Leu Ala Val Ala Asn Tyr Asp Asp Thr Ile Glu Leu Gly Leu Gln
                325                 330                 335

Val Ile Pro Gln Ser Pro Ser Leu Ala Ser Ala Val Gly Leu Pro Leu
            340                 345                 350

Thr Ser Ala Asp Val Ser Gly Gly Gly Gly Val Lys Ser Ala Ser Thr
        355                 360                 365

Ser Arg Ser Gly Ser Pro Asn Asn Ser Leu Ser Arg Ser Asn Ser Val
    370                 375                 380

His Asp Gly Pro Leu Leu Cys Val Phe Glu Ile Val His Asn Ile Tyr
385                 390                 395                 400

Gln Pro Pro Pro Ser Ser Ala Ser Ala Thr Pro Lys Ala Glu Leu Asn
                405                 410                 415

Pro Phe Thr His Leu Ala Glu Glu Thr Glu Ala Leu Lys Pro Arg Leu
            420                 425                 430

Asp Thr Ala Phe Cys Lys Asn Leu Leu His Arg Gln Asn Ala Val Leu
        435                 440                 445

Lys Val Asp Val Gln Pro Ser Ser Pro Leu Gly Ser Gly Met Pro Arg
    450                 455                 460

Arg Ala Tyr Ala Leu Ser Val Leu Leu Pro Arg Gly Lys Pro Ile Thr
465                 470                 475                 480

Glu Pro Ala Ile Leu Ser Lys Glu Glu Gln Glu Val Arg Gln Pro Phe
                485                 490                 495

Ser Ser His Val Leu Ala Arg Glu Pro Thr Leu Asn Glu Leu Ser Glu
            500                 505                 510

Phe Ala Glu Ser Leu Arg Gly Arg Lys Val Phe Ile His Ala Asn Leu
        515                 520                 525

Ser Ser Val Phe Ala Arg His Leu Thr Ser Tyr Leu Ala Ala Trp Gly
    530                 535                 540

Met Asp Ile Ser His Leu Pro Thr Asp Gly Asp Glu Ala Asp Lys Leu
545                 550                 555                 560

Lys Asp Val Ala Ala Lys His Asp Ser Ala Tyr Thr Gly Ser Met Gly
                565                 570                 575

Val Ser Gly Gly Thr Thr Ser Ser Ala Glu Thr Pro Tyr Ser Ile Lys
            580                 585                 590

Pro Thr Gly Val Thr Ala Val Gln Pro Gly His Phe Val Ile Ile Asp
        595                 600                 605

Asp Asp Val Ala Val Leu Arg Arg Glu Leu Val Arg Ile Arg Ser Glu
    610                 615                 620

Leu Leu Pro Ile Leu Phe Lys Pro Arg Leu Ser Lys Arg Pro Thr Met
625                 630                 635                 640

Thr Ser Arg Thr Arg Ser Thr Pro Ser Leu Arg Gln Val Pro Pro Arg
                645                 650                 655

Ser Ser Ser Gly Ser Val Leu Ile His Phe Thr Ser Leu Ala Asn Tyr
            660                 665                 670

Asn Arg Val Arg Asp Ala Ile Ala Ser Phe Val Gly Ala Pro Gly Leu
        675                 680                 685

Thr Asn Pro Glu Thr Tyr Val Gln Pro Glu Val Ile Val Ile Pro Lys
    690                 695                 700

Pro Val Gly Pro Arg Arg Phe Leu Thr Ala Leu His Thr Ala Val Lys
705                 710                 715                 720

Gln Pro Met Val Asp Pro Phe Phe Ser Pro Ile Ala Thr Ser Pro Arg
```

```
                725                 730                 735

Ser Pro Gly Gly Gly Tyr Phe Gly Gly Leu Arg Thr Pro Thr Glu Arg
            740                 745                 750

Glu Ser Gly Phe Phe Asp Ser Val Ala Glu Glu Pro His Glu Glu Ala
        755                 760                 765

Asp Ser Arg Pro Asp Tyr Ala Thr Val Gln Lys Ala Arg Ser Pro Leu
    770                 775                 780

Gly Glu Phe Pro Pro Ser Ala Ala Gln Ile Val Arg Thr Asn Gln Gly
785                 790                 795                 800

Leu His Leu Ser Leu Pro Thr Pro Asn Glu Ile Met Thr Thr Pro Ala
                805                 810                 815

Pro Glu Tyr Phe Ser Gly Ser Ser Lys Ser Pro Ser Ser Gly Ala Ser
            820                 825                 830

Gly Val Val Met Gln Ser Pro Asp Gly Arg Pro Phe Gly Met Phe Phe
        835                 840                 845

Glu Pro Pro Ile Lys Asn Glu Arg Arg Gly Ser Thr His Arg Thr Pro
    850                 855                 860

Ser Asp Ser Ile Arg Arg Lys Gln Ala Asn Arg Arg Ala Ser Thr Ser
865                 870                 875                 880

Asp Glu Pro Phe Ser Ser Pro Ser Thr Ala Leu Pro Pro Arg Arg Ser
                885                 890                 895

Ser Thr Ile Ser Thr Thr Gly Asn Glu Glu His Arg Ser Ser Pro Ile
            900                 905                 910

Ala Asn Val Thr Asp Arg Pro Thr His Ser Arg Val Asn Ser Arg Arg
        915                 920                 925

Lys Asn Asn Leu Pro Ala Ala Glu Gln Pro Ile Leu Ala Val Gly Arg
    930                 935                 940

Ala Lys Gly Arg Glu Arg Ser Glu Thr Val Thr Lys Gly Gly Asp Leu
945                 950                 955                 960

Gly Ser Arg Lys Gly Thr Pro Ala Ala Ser Pro Arg Ile Glu Glu Lys
                965                 970                 975

Lys Glu Leu Glu Arg Gly Glu Lys Thr Lys Ser Leu Ala Pro Ser Thr
            980                 985                 990

Ala Pro Thr Lys Lys Asn Ala Lys  Val Asp Val Val Val  Pro Pro Ile
        995                 1000                1005

Asn Val  Leu Ile Val Glu Asp  Asn Pro Ile Asn Gln  Asn Ile Leu
    1010                1015                1020

Ser Met  Phe Leu Arg Lys Lys  Lys Ile Lys Asn Ser  Ser Ala Lys
    1025                1030                1035

Asp Gly  Ala Glu Ala Val Glu  Lys Trp Arg Thr Gly  Gly Phe His
    1040                1045                1050

Leu Ile  Leu Met Asp Ile Gln  Leu Pro Val Met Asp  Gly Ile Ala
    1055                1060                1065

Ala Thr  Lys Glu Ile Arg Arg  Leu Glu Arg His Asn  Asn Ile Gly
    1070                1075                1080

Val Phe  Pro Ser Thr Pro Ala  Ala Glu Leu Pro Arg  Gly Gln Asn
    1085                1090                1095

Val Ala  Asp Ser Pro Pro Pro  Ser Ser Pro Phe Arg  Ser Ser Val
    1100                1105                1110

Ile Ile  Val Ala Leu Thr Ala  Ser Ser Leu Gln Ser  Asp Arg Val
    1115                1120                1125

Ala Ala  Leu Ala Ala Gly Cys  Asn Asp Phe Leu Thr  Lys Pro Val
    1130                1135                1140
```

-continued

```
Ser Leu  Lys Trp Leu Asp Lys  Lys Ile Val Glu Trp  Gly Cys Met
    1145                 1150                 1155

Gln Ala  Leu Ile Asp Phe Asp  Gly Trp Arg Arg Trp  Lys Ser Ser
    1160                 1165                 1170

Asp Thr  Lys Asn Pro Ser Glu  Thr Lys Gln Gly Phe  Ser Val Gly
    1175                 1180                 1185

Pro Gln  Gln Ala Ala Arg Ser  Leu Ala Ser Arg Leu  Arg Ile Glu
    1190                 1195                 1200

Arg Lys  Gly Ser Arg Ser Pro  Ala Ala Pro Val Ser  Thr Pro Arg
    1205                 1210                 1215

Leu Asn  Leu Gln Ser Ala Thr  Pro Asp Arg Pro Glu  Thr Pro Pro
    1220                 1225                 1230

Asp Ser  Thr Ser Gln Met Pro  Lys Ala Pro Pro Val  Ala Ala Ser
    1235                 1240                 1245

Asp Pro  Pro Leu Ser Pro Lys  Ser Leu Asn Lys Thr  Val Asn Asp
    1250                 1255                 1260

Val Phe  Glu Gln Ala Asp Ala  Arg Leu Glu Asn Ala  Arg Glu Glu
    1265                 1270                 1275

Gln Gly  Val Ser Ser Gln Lys  Glu Asn Thr Ser Leu  Thr Asp Ser
    1280                 1285                 1290

Thr Asn  Thr Thr Ile Thr Pro  Ser Lys Thr Tyr Pro  Ala Pro Pro
    1295                 1300                 1305

Pro


<210> SEQ ID NO 2
<211> LENGTH: 1691
<212> TYPE: PRT
<213> ORGANISM: Cryptococcus neoformans
<220> FEATURE:
<221> NAME/KEY: PEPTIDE
<222> LOCATION: (1)..(1691)
<223> OTHER INFORMATION: amino acid sequence of TCO2 serotype A H99
      strain

<400> SEQUENCE: 2

Met Ile Leu Gly Thr Asp Ile Asp Leu Ser Ser Ile Pro Thr Ala Phe
1               5                   10                  15

Leu Glu Ala Tyr Pro Phe Pro Ala Val Val Phe Val Ile Asp Ser Pro
            20                  25                  30

Pro Ser Pro Arg Pro Arg Leu His Ser Arg Asn Thr Asp Thr Thr Ile
        35                  40                  45

Arg Arg Thr Asp Gly Gln Ile Ser Pro Leu Thr Gly Pro Pro Val Gln
    50                  55                  60

Gln Phe Ala Ser Ala Pro Val Val Trp Gly Asn Gln Arg Trp His Glu
65                  70                  75                  80

Leu Ala Gln Gly Lys Thr Ile Ala Glu Cys Val Asp Val Ala Ser Gln
                85                  90                  95

Asn Lys Leu Gln Thr Trp Val Glu Asn Asp Thr Gly Asp Lys Ser Glu
            100                 105                 110

Ser Leu Ala Leu Asp Leu Lys Val Pro Gln Gly Val Thr Leu His Leu
        115                 120                 125

Ala Lys Thr Ile Leu Pro Leu Ser Pro Pro Ser Ser Ser Gln Ser Leu
    130                 135                 140

Cys Ile Leu Ile Ser Gln Tyr Ile Asp Lys Pro Glu Ser Phe Ala Pro
145                 150                 155                 160
```

-continued

```
Pro Ile Ser Ser Gly Asp Ile Leu Phe Ser Ser Leu Ser Arg Leu Ser
                165                 170                 175

Gln Thr Phe Ser Arg Ser Ser Ser Phe Ser Ser Asn Pro Arg Lys Ser
            180                 185                 190

Ile Asp Val Pro Ala Ser Leu Ser Glu His Arg Gly Ser Ala Thr Ser
        195                 200                 205

Thr Ser Ser Asn Leu Arg Ser Ser Ile Asp Leu Thr Ser Pro Asn Ser
    210                 215                 220

Gln Pro Ser Pro Leu Asn Arg Glu Gln Ser Thr Tyr Phe Thr His Gly
225                 230                 235                 240

Ser Ala Thr Arg Glu Glu Arg Pro Ser Val Arg Arg Arg Arg Ser Pro
                245                 250                 255

Pro Ile Ser Met Thr Arg Pro Lys Pro Leu Glu Ser His Ala Gln Glu
            260                 265                 270

Cys Trp Asp Leu Val Glu Asn Phe Asp Trp Ser Lys Thr Ala Leu Gly
        275                 280                 285

Pro Arg Glu Gln Trp Met Asp Ala Leu Asp Pro Val Leu Ala Ile Thr
    290                 295                 300

Phe Glu Ser Arg Thr Ala Asp Cys Ala Trp Leu Gly Pro Asp Leu Glu
305                 310                 315                 320

Leu Val Tyr Asn Lys Ala Tyr Gln Glu Leu Val Asp His Pro Asn Ala
                325                 330                 335

Phe Gly Lys Pro Ala Arg Gln Val Trp Ala Thr Asn Trp Asp Tyr Leu
            340                 345                 350

Glu Pro Leu Val Lys Arg Cys Leu Ser Gly Thr Pro Val Tyr Lys Asp
        355                 360                 365

Asn Asp Pro Leu Phe Trp Arg Arg Tyr Gly Asn Gly Arg Leu Leu Glu
    370                 375                 380

His Tyr His Thr Trp Arg Tyr Val Pro Ile Thr Gly Lys Asp Gly Ser
385                 390                 395                 400

Val Leu Gly Ile Phe Asn Gln Ser Ile Glu Val Thr Asp Ser Val Leu
                405                 410                 415

Leu Glu Arg Arg Met Gly Thr Thr Arg Glu Leu Ser Glu His Met Ser
            420                 425                 430

Phe Ile Arg Thr Thr Glu Asp Phe Phe Ser Ser Val Ala Asp Val Phe
        435                 440                 445

Ser Gln Asn Pro Thr Asp Ile Pro Phe Ala Leu Cys Tyr Arg Val Arg
    450                 455                 460

Gln Val Asp Thr Asp Gly Thr Phe Val His Leu Asp Val Ser Leu Gln
465                 470                 475                 480

Ser Ser Val Gly Val Pro Glu Gly His Pro Ser Ala Pro Asp Gln Ile
                485                 490                 495

Pro Val Ser Phe Leu Asn Gly Asn Pro Tyr Pro Ser Asn Val Glu Arg
            500                 505                 510

Ser Phe Ser Pro Ala Phe Ser Ile Val Ser Ile His Ser Ser Ser Ser
        515                 520                 525

His Arg Val Cys His Val Ser Glu Asp Thr Thr Gln Trp Pro Ile Ala
    530                 535                 540

Lys Ala Leu Gln Arg Arg Gln Cys Val Ile Ile Glu Glu Cys Ser Gln
545                 550                 555                 560

Leu Ile Glu Gly Tyr Pro Ile Arg Arg Trp Asp Gly Leu Pro Phe Ser
                565                 570                 575

Ala Ile Val Val Pro Ile Cys Ser Glu Gly Ser Pro Glu Ile Pro Asp
```

-continued

```
            580                 585                 590

Ala Val Val Ile Leu Gly Leu Asn Val Arg Arg Cys Phe Asp His Glu
        595                 600                 605

Tyr Asp Ser Trp Ile His Ser Ile Arg Ser Gln Leu Ser Ser Ala Leu
    610                 615                 620

Val Met Val Lys Ala Arg Glu Ala Glu Gln Lys Met Val Glu Glu Ser
625                 630                 635                 640

Ala Arg Met Glu Lys Ala Lys Val Ala Trp Phe Arg Gly Ala Ala His
                645                 650                 655

Asp Leu Arg Ser Pro Leu Thr Leu Val Ala Gly Pro Leu Ala Asp Val
            660                 665                 670

Leu Asp Ser Asp Leu Asn Ser Ser Gln Arg Thr Ala Leu Thr Val Ala
        675                 680                 685

Gln Arg Asn Leu Asp Arg Leu Val Arg Leu Val Asn Ala Leu Met Asp
    690                 695                 700

Phe Ser Arg Val Glu Ala Gly Arg Met Glu Gly Arg Phe Val Pro Thr
705                 710                 715                 720

Asn Leu Ser Gln Phe Val Thr Gln Leu Ala Ala Leu Phe Lys Pro Ala
                725                 730                 735

Ile Glu Arg Leu Gly Leu Glu Tyr Val Leu Asp Val Gln Pro Ser Glu
            740                 745                 750

Glu Leu Val Phe Ile Asp Pro Val Leu Phe Glu Thr Val Val Ser Asn
        755                 760                 765

Leu Ile Gly Asn Ala Leu Lys Tyr Thr Glu Thr Gly Ser Ile Thr Val
    770                 775                 780

Arg Val Gln Tyr Thr Asp Tyr Ala Glu Val Ser Val Ile Asp Thr Gly
785                 790                 795                 800

Val Gly Ile Pro Lys Asn Glu Leu Ala Leu Val Thr Glu Trp Phe His
                805                 810                 815

Arg Ala Ser Thr Ala Ile His Ser Gly Thr Gln Gly Thr Gly Leu Gly
            820                 825                 830

Leu Ala Leu Ala Lys Glu Leu Leu Lys Leu His Lys Gly Glu Leu Leu
        835                 840                 845

Val Glu Ser Gln Thr Ala Asn Glu Ser Gly Gly Pro His Gly Ser Ile
    850                 855                 860

Phe Thr Ala Lys Ile Pro Leu Asp Phe Lys Pro Ser Pro Ser Ala His
865                 870                 875                 880

Ile Ile Pro Ser Val Glu Ser His Lys Thr Phe Gly Lys Tyr Ser Lys
                885                 890                 895

Ala Val Ala Asp Glu Ala Met Arg Trp Val Gly Asp Ser Asp Ala Ala
            900                 905                 910

Ser Glu Ala Tyr Asp Met Ser Ser Gly Thr Gly Val Ser Ser Ala Gly
        915                 920                 925

Ser Gly Ser Gly Asn Thr Thr Thr Phe Gly Pro Lys Phe Ala Asp Ala
    930                 935                 940

Phe Leu Phe Asp Lys Asn Asp Ile Val Leu Ile Val Glu Asp Asn Val
945                 950                 955                 960

Asp Met Arg Glu Tyr Ile Arg Gln Leu Phe Ala Pro Tyr Cys Thr Val
                965                 970                 975

Leu Glu Ala Ser Asn Gly Glu Gln Ala Tyr Asn Met Ala Thr Gln Asn
            980                 985                 990

Pro Pro Asn Leu Ile Leu Ser Asp  Val Leu Met Pro Lys  Leu Ser Gly
        995                 1000                1005
```

Met Glu Leu Leu Gln Arg Ile Arg Ser His Pro Asp Thr Arg Ile
1010 1015 1020

Val Pro Met Val Leu Ile Ser Ala Ile Ala Gly Asp Glu Ser Arg
1025 1030 1035

Val Glu Ala Leu Leu Asn Gly Ala Asp Asp Tyr Leu Ala Lys Pro
1040 1045 1050

Phe Lys Pro Lys Glu Leu Ile Ala Arg Val His Leu His Met Gln
1055 1060 1065

Val Gly Lys Lys Arg Ala Lys Leu Glu Ala Leu Tyr Ala Gln Arg
1070 1075 1080

Glu Thr Glu Leu Thr Ala Leu Ser Asp Tyr Cys Pro Ile Gly Ile
1085 1090 1095

Phe Arg Gly Asp Lys Tyr Gly His Ile Val Tyr Ala Asn Ala Ala
1100 1105 1110

Trp Arg Ala Gln Ser Gly Leu Leu Val Gly Asp Pro Asn Asp Trp
1115 1120 1125

Ala Ser Tyr Val His Pro Asp Ser Lys Ala Gln Leu Leu Glu Gln
1130 1135 1140

Trp Asn Gln Trp Leu Arg Gly Asp Leu Lys Glu Phe Arg Ala Ala
1145 1150 1155

Trp Arg Trp Ser Asn Gly Ile Pro Val Arg Ser Ile Leu Val Arg
1160 1165 1170

Leu Asp Asp Val Lys Glu Gly Phe Ser Gly Leu Ile Gly Cys Val
1175 1180 1185

Val Asp Val Ser His Glu Glu Arg Arg Leu Ile Glu Ala Glu Glu
1190 1195 1200

Arg Arg Lys Glu Ala Glu Glu Ser Lys His Gln Gln Glu Leu Leu
1205 1210 1215

Ile Asp Leu Thr Ser His Glu Ile Arg Thr Pro Val Ser Ala Ile
1220 1225 1230

Leu Gln Cys Ser Asp Leu Val Lys Glu Asn Leu Val Ala Leu Lys
1235 1240 1245

Asp Gln Leu Arg Gly Ala Gly Pro Lys Gly Phe Val Pro Ser Gln
1250 1255 1260

Glu Leu Leu Ala Asp Leu Glu Gln Asp Val Glu Ala Leu Glu Ser
1265 1270 1275

Ile Tyr Gln Cys Gly Leu Val Gln Glu Arg Ile Ala Gly Asp Val
1280 1285 1290

Leu Ser Leu Ala Arg Ile Gln Leu Asp Met Leu Ser Leu His Asp
1295 1300 1305

Ile Asp Val Asn Leu Arg Arg Glu Gly Arg Lys Val Ser Ser Ile
1310 1315 1320

Phe Ala Ser Glu Ala Lys Met Lys Asp Ile Asp Leu Gln Leu Glu
1325 1330 1335

Phe Gly Pro Thr Ile Glu Gln Ser Lys Val Leu Ala Ile Lys Thr
1340 1345 1350

Asp Pro Val Arg Leu Gly Gln Val Val Thr Asn Leu Ile Ser Asn
1355 1360 1365

Ala Ile Arg Phe Thr Ser Ser Ser Asp Val Arg Lys Ile Thr Ile
1370 1375 1380

Gln Tyr Asp Val Ser Phe Val Pro Pro Ala Asp Asp Ser Cys Ala
1385 1390 1395

```
Leu Pro  Ser Ser Val Gly Leu  Pro Asp Ile Leu Pro  Val Lys Glu
    1400                 1405                 1410

Asn Thr  Pro Leu Trp Leu Phe  Val Ser Val Thr Asp  Ser Gly Pro
    1415                 1420                 1425

Gly Met  Thr Glu Gln Glu Leu  Ser Val Leu Phe Gln  Arg Phe Ala
    1430                 1435                 1440

Gln Gly  Asn Lys Met Ile His  Thr Lys Tyr Gly Gly  Ser Gly Leu
    1445                 1450                 1455

Gly Leu  Phe Ile Cys Arg Lys  Ile Thr Glu Leu Leu  Gly Gly Arg
    1460                 1465                 1470

Ile Glu  Val Leu Ser Gln Val  Gly His Gly Ser Val  Phe Arg Phe
    1475                 1480                 1485

Phe Ile  Lys Thr Arg Ala Val  Ala Pro Pro Ser Ala  Ile Ala Ala
    1490                 1495                 1500

Leu Val  Glu Ser Ser Pro Leu  Lys Pro Val Ser Ala  Thr Ser Pro
    1505                 1510                 1515

Ser Ser  Ser Leu Ala Met Ser  Arg Ser Ser Ser Arg  Ser Thr Asn
    1520                 1525                 1530

Val Thr  Thr Pro Ile Glu Gly  Gly Gly Thr Glu His  Val Leu Ile
    1535                 1540                 1545

Val Glu  Asp Asn Leu Ile Asn  Gln Thr Val Leu Lys  Arg Gln Leu
    1550                 1555                 1560

Val Lys  Ala Gly Leu Ser Cys  Asn Val Ala Ser Asn  Gly Leu Glu
    1565                 1570                 1575

Ala Leu  Asn Val Ile Arg Glu  Val His Arg Gln His  Arg Arg Gly
    1580                 1585                 1590

Gly Pro  Asn Arg Lys Arg Leu  Phe Asp Val Val Leu  Met Asp Leu
    1595                 1600                 1605

Glu Met  Pro Val Met Asp Gly  Ile Thr Ala Val Arg  Glu Ile Arg
    1610                 1615                 1620

Gln Ser  Glu Ala Ala Gly Thr  Leu Gly Arg Asn Met  Val Ile Ala
    1625                 1630                 1635

Leu Thr  Gly Asn Ala Arg Gln  Gly Gln Ile Asp His  Ala Leu Ala
    1640                 1645                 1650

Ser Gly  Phe Asp Asp Val Val  Ile Lys Pro Tyr Ile  Leu Val Asp
    1655                 1660                 1665

Leu Leu  Asn Lys Ile Lys Ser  Met Lys Val Arg Lys  Leu Glu Leu
    1670                 1675                 1680

Glu Thr  Ala Lys Ala Gln Glu  Glu
    1685                 1690


<210> SEQ ID NO 3
<211> LENGTH: 1417
<212> TYPE: PRT
<213> ORGANISM: Cryptococcus neoformans
<220> FEATURE:
<221> NAME/KEY: PEPTIDE
<222> LOCATION: (1)..(1417)
<223> OTHER INFORMATION: amino acid sequence of SSK2 serotype A H99
      strain

<400> SEQUENCE: 3

Met Ser Asn Pro Thr Ser Pro Ser Asn Pro Ser Asp Thr Gly Pro Ser
1               5                   10                  15

Ser Ala Ser Asn Val Thr Ser Ser Ser Ser Lys Thr Gly Arg Arg Ser
            20                  25                  30
```

-continued

```
Val Arg Leu Phe Ala Pro Asp Glu Glu Asp Ser Ser Asp Glu Asp Gly
        35                  40                  45

Gly Leu Ile Gly Val Pro Ala Glu Thr Thr Phe Lys Asp Asp Glu Ile
    50                  55                  60

Pro Pro Ser Asn Pro Arg Ser Ala Ser Tyr Pro Gly Pro Pro Ala His
65                  70                  75                  80

Thr Ser Pro Thr Ser Lys Ile Ser Thr Ile Val Ser Ser Ala Ser Ala
                85                  90                  95

Ala Gln Pro Lys Leu Ala Arg Ser Ile Thr Tyr Val Ala Pro Asn Ala
            100                 105                 110

Val Ser Ser Arg Pro Ala Tyr Pro Leu Asn Pro Ala Gly Ser Glu Thr
        115                 120                 125

Leu His Ala Ser Gly Arg Ser Tyr Thr Asp Pro Asp Ile Gly Tyr Phe
    130                 135                 140

Ser His Asp Ala Gly Asp Asp Gly Trp Gly Ser Asp Asp Asp Asp Glu
145                 150                 155                 160

Leu Arg Ser Pro Gly Trp Gly Ile Ser His His Asn Met Asp Ser Gly
                165                 170                 175

Gly Lys Thr Asn Gly Ser Pro Gln Leu Pro Ile Lys Pro Ala Asp Val
            180                 185                 190

Thr Glu Asp Glu Gly Gln Glu Arg Leu Asp Trp Gln Gly Met Leu Glu
        195                 200                 205

Ser Val Leu Asn Ser Asp Val Leu Lys Val Glu Glu Gln Arg Ile Tyr
    210                 215                 220

Asn Ser Met Pro Thr Asp Ser Phe Arg Glu Glu Ile Gly Lys Thr Leu
225                 230                 235                 240

Trp Trp Gln Ile Arg Ala Lys Leu Arg Gly Arg Thr Glu Ala Glu Glu
                245                 250                 255

Lys Lys Arg Val Gln Glu Arg Arg Ala Arg Val Val Asp Pro Val Leu
            260                 265                 270

Glu Glu Ile Asn Glu Phe Lys Tyr Asp Pro Lys Asn Asn Pro Glu Gly
        275                 280                 285

Glu Glu Asp Ser Asp Gly Asp Pro Gln Asp Ala Thr Ser Thr Ala Ala
    290                 295                 300

Pro Gln Ser Lys Ala Leu Asn Gln Val Asn Thr Val Leu Ala Lys Leu
305                 310                 315                 320

His Ala Ile Lys Gly Leu Tyr Pro Asn Leu Ala Ala Met Arg Ala Asp
                325                 330                 335

Lys Val Leu Tyr Thr Asp Glu Asn Phe Arg Lys Arg Ala Asp Ala Leu
            340                 345                 350

Thr Ser Trp Ser Ile Ile Val Ser Ser Leu Gln Thr Gln Leu Lys Leu
        355                 360                 365

Leu Gln Lys Trp Thr Gly Ser Asp Glu Leu Asp Ile Thr Lys Pro Asn
    370                 375                 380

Thr Thr His Glu Lys Ala Leu Val Gly Lys Tyr Lys Tyr His Ser Ile
385                 390                 395                 400

Asp Ser Lys Gly Thr Pro Gly Arg Asp Ala Ala Asp Asp Ser Ser Phe
                405                 410                 415

Leu Asp Arg Val Ile Lys Glu Asp Asn Leu Gln Arg Thr Phe Glu Arg
            420                 425                 430

Arg Ala Phe Val Asp Met Ile Asn Leu Val Arg Asn Ala Lys Glu Thr
        435                 440                 445

Val Ile Ser Tyr Leu Pro Gln Phe Gln Glu Gln Asn Leu Pro Asp Phe
```

-continued

```
    450                 455                 460

Gln Tyr Glu Ile Val Arg Leu Ile Gly Phe Pro Gly Arg Leu Ile Ile
465                 470                 475                 480

Glu Ala Val Lys Val Arg Leu Asp Ala Ala Ser Arg Leu Leu Asp Pro
                485                 490                 495

Asn Pro Met Val Val Glu Asp Phe Ile Glu Asn Leu Arg Leu Ser Ile
            500                 505                 510

Ser Leu Ala Val Leu Ile Arg Lys Gln Tyr Asp Glu Ile Met Ala Pro
        515                 520                 525

Asp Ala Glu Gly Arg Trp Lys Ile Pro His Cys Leu Pro Thr Glu Tyr
    530                 535                 540

Asn Asp Val Leu Leu Asp Ala Leu Arg Thr Phe Phe Lys Leu Leu His
545                 550                 555                 560

Trp Arg Leu Arg Gly Val Gly Lys Ala Ser Tyr Tyr Lys Glu Thr Glu
                565                 570                 575

Val Leu Glu Glu Glu Ala Pro Phe Leu Tyr Glu Ala Ala Glu Ala Ile
            580                 585                 590

Val Gly Gly Asp Met Val Val Ala Glu Gln Tyr Cys Ala Leu Ser Asn
        595                 600                 605

Lys Leu Leu Ile Arg Ser Ala Asn Tyr Leu Asp Gln Gln Leu Arg Val
    610                 615                 620

Pro Ile His Ser Pro Ser Arg Asp Lys Glu Arg Gly Asp Lys Glu Arg
625                 630                 635                 640

Asp Gly Ser Ser Ser Ser Gln Arg Asn Arg Asp Gly Arg Asp Ser Ser
                645                 650                 655

Leu Pro Gly Pro Pro Lys His Met Lys Val Glu Glu Leu Phe Ser Trp
            660                 665                 670

Tyr Ser Lys Leu Leu Asp Ser Ala Arg Met Arg His Arg Lys Thr Gln
        675                 680                 685

Arg Phe Cys Arg Lys Leu Thr Gln Arg Phe Asp Asn Ser Ala Glu Tyr
    690                 695                 700

Ser Ile Glu Glu Thr Glu Met Asp Met Leu Val Glu Thr Leu Gln Asp
705                 710                 715                 720

Thr Gly His Phe Leu Val Tyr Thr Gly Lys Phe Glu Ala Asn Gly Thr
                725                 730                 735

Tyr Ile Val Ala Asp Gly Ser Leu Trp Gly Gln Pro Asp Asp Val Arg
            740                 745                 750

His Leu Leu Lys Arg Val Phe Ser Val Thr Ile Pro Gly Ser Arg Val
        755                 760                 765

Arg Pro Arg Gln Thr Thr Ser Gln Val Ser Val Gly Gly Ala Ser Pro
    770                 775                 780

Ser Asn Gly Gln Val Ala Ala Gln His Asp Pro Ala Asp Pro Tyr Pro
785                 790                 795                 800

Glu Ala Asp Asp Phe Asp Asp Glu Ala Leu Ala Ala Tyr Ile Leu Leu
                805                 810                 815

Ile Ser Pro Arg Gln Ser Phe Val Trp Ser Gly Ala Val Met Thr Leu
            820                 825                 830

Asp Val Asp Tyr Ile Asp Tyr Glu Leu Pro Asp Asn Arg Val Arg Leu
        835                 840                 845

Ile Ala Asp Gly Pro Thr Lys Arg Leu Ala Leu Cys Lys Leu Tyr Phe
    850                 855                 860

Lys Gln Ala Leu Ile His Pro Asp Thr Gly Glu Thr Ile Asp Leu Pro
865                 870                 875                 880
```

-continued

```
Cys Val Val Glu Ala Gln Ala His Leu Pro Thr Ile Gln Lys Gln Leu
                885                 890                 895

Val Lys Ile Ala Lys Ser Ser Tyr Arg Leu Ser Glu Cys Ile Val Gln
            900                 905                 910

Ser Ala Pro Leu Val Arg Asn Ala Phe Arg Gly Lys Pro Gly Ser Gln
        915                 920                 925

Glu Leu Val Glu Asn Trp Tyr Ser Phe Ala Thr Glu His Gly Thr Arg
    930                 935                 940

Val Leu Ile His Ile Glu Pro Ser Val Trp Glu Arg Phe Asn Arg Leu
945                 950                 955                 960

Leu Met Arg Leu Ala Ile Ser Trp Ile Ser Phe Ile Ser Gln Glu Cys
                965                 970                 975

Asn Pro Thr Asp Arg Lys Thr Phe Arg Trp Thr Val Ala Ala Leu Thr
            980                 985                 990

Tyr Ala Phe Asn Met Thr Arg Gly  Ser Asn Ile Leu Ala  Leu Asp Arg
        995                 1000                1005

Ser Glu  Phe Ser Leu Leu Arg  Arg Ser Ser Met Glu  Ala Lys Lys
    1010                 1015                 1020

Glu Ala  Asp Arg Ile Glu Ala  Met Arg Arg Leu Gln  Arg Leu Gln
    1025                 1030                 1035

Glu Asn  Leu Asp Asp Glu Phe  Leu Pro Arg Thr Pro  Thr Glu Ser
    1040                 1045                 1050

Gly Asp  Gln Pro Arg Ile Asp  Arg Ser Ile Arg Leu  Thr Val Glu
    1055                 1060                 1065

Glu Arg  Leu Arg Leu Ile Ala  Glu Leu Glu Ala Arg  Arg Asp Glu
    1070                 1075                 1080

Leu Ala  Pro Ala Pro Val Gly  Gln Val Leu Asp Glu  Glu Val Ser
    1085                 1090                 1095

Glu Asp  Arg Ala Leu Val Phe  Leu Ala Ala Ser Lys  Ser Asn Ile
    1100                 1105                 1110

Ser Met  Arg Trp Gln Gln Gly  Ala Tyr Ile Gly Gly  Gly Ala Ser
    1115                 1120                 1125

Gly Ser  Val Tyr Leu Gly Tyr  Ser Leu Gln Asp Asn  Thr Val Phe
    1130                 1135                 1140

Ala Val  Lys Ile Leu Pro Thr  Val Asp Leu Gln Ser  Ser Pro Ala
    1145                 1150                 1155

Leu Tyr  Glu Ser Ile Lys Arg  Glu Ser Asp Val Met  Ser Leu Leu
    1160                 1165                 1170

Ser His  Pro Asn Ile Val Gly  Phe Leu Gly Leu Glu  Val His Arg
    1175                 1180                 1185

Asn Arg  Val Cys Leu Phe Gln  Glu Tyr Cys Glu Gly  Gly Ser Leu
    1190                 1195                 1200

Ala Gly  Met Leu Glu Tyr Gly  Lys Ile Asp Asp Glu  Glu Val Val
    1205                 1210                 1215

Gly Ala  Phe Thr Ile Gln Leu  Leu Arg Gly Leu Glu  Tyr Leu His
    1220                 1225                 1230

Thr Asn  Arg Ile Glu His Arg  Asp Leu Lys Pro Glu  Asn Ile Leu
    1235                 1240                 1245

Ile Gly  Ala Asn Ser Val Leu  Lys Leu Ala Asp Phe  Gly Thr Ala
    1250                 1255                 1260

Lys Ile  Ile Lys Ser Asn Lys  Thr Leu Ala Arg Thr  Arg Gly Gly
    1265                 1270                 1275
```

```
Ala His  Ala Lys Met Glu Gly  Leu Glu Gly Thr Pro  Met Tyr Met
    1280                 1285                 1290

Ala Pro  Glu Met Ile Lys Asn  Gln Arg Thr Gly Lys  Leu Gly Ala
    1295                 1300                 1305

Cys Asp  Ile Trp Gly Leu Gly  Cys Ile Val Leu Gln  Met Ile Thr
    1310                 1315                 1320

Gly Arg  Lys Pro Trp Ser Phe  Leu Asp Phe Asp Asn  Glu Trp Ala
    1325                 1330                 1335

Ile Met  Phe His Leu Gly Ala  Thr Lys Glu Pro Pro  Pro Leu Pro
    1340                 1345                 1350

Asp Pro  Asn Glu Met Ser Asp  Gln Gly Ile Glu Phe  Ile Asp Gln
    1355                 1360                 1365

Cys Leu  Ser Leu Asp Pro Glu  Ala Arg Pro Val Ala  Ser Glu Leu
    1370                 1375                 1380

Leu Gln  Asp Glu Trp Leu Val  Pro Met Leu Glu Gln  Met Val Ser
    1385                 1390                 1395

Cys Leu  Ser Cys Arg Ala Gly  Ala Arg Ile Pro Arg  Tyr Ile Gly
    1400                 1405                 1410

Asp Gly  Pro Lys
    1415


<210> SEQ ID NO 4
<211> LENGTH: 609
<212> TYPE: PRT
<213> ORGANISM: Cryptococcus neoformans
<220> FEATURE:
<221> NAME/KEY: PEPTIDE
<222> LOCATION: (1)..(609)
<223> OTHER INFORMATION: amino acid sequence of PBS2 serotype A H99
      strain

<400> SEQUENCE: 4

Met Thr Asp Pro Thr Pro Pro Ala Leu Asp Ser Leu Ser Leu Ala Asp
1               5                   10                  15

Lys Ala Pro Thr Pro Glu Glu Ser Pro Glu Asp Ala Ala Glu Gln Pro
            20                  25                  30

Lys Pro Ala Ala Ser Pro Ser Ala Gly Thr Pro Gly His Asp Ala Gln
        35                  40                  45

Ser Ser Ser Thr Ser Pro Pro Gln Arg Pro Gln Ser Met Gln Thr Asn
    50                  55                  60

Asp Lys Ala Pro Asp Thr Ser Ala Pro Ala Ser Arg Pro Gln Pro Gln
65                  70                  75                  80

His Val Pro Ala Ser Ala Pro Ala Leu Pro Ser Thr Asn Pro Val Arg
                85                  90                  95

Pro Gln Pro Gly Ala Arg Pro Gly Ala Ala Arg Gly Met Pro Ala Pro
            100                 105                 110

Met Gly Met Arg Ala Gln Ala Gly Arg Gly Ala Gly Gly Pro Gln Met
        115                 120                 125

Gln Thr Lys Met Leu Pro Ser Leu Gln Ala Lys Met Asp Lys Ile Ala
    130                 135                 140

Ala Ser Arg Gln Gly Pro Pro Pro Ser Ser Gly Met His Asp Pro Asn
145                 150                 155                 160

Ala Thr Ser Met Gly Ala Leu Leu Arg Ser Gln Ala Leu Arg Ala Pro
                165                 170                 175

Gly Ala Ser Gln Ala Pro Pro Gly Pro Gly Pro Ala Ser Gly Pro Phe
            180                 185                 190
```

-continued

```
Gly Leu Ala Ala Arg Arg Ala Ala Ala Gly Gly Pro Pro Arg Pro Asn
        195                 200                 205

Leu Gly Met Met Gly Met Gly Ala Ser Ala Pro Gly Ala Val Gly Arg
    210                 215                 220

Gly Ser Gly Leu Ala Gly Arg Arg Gly Pro Pro Gly Gly Leu Thr Leu
225                 230                 235                 240

Ser Gly Met Lys Gly Ala Ile Lys Asp Glu Gly Asn Lys Phe Ser Asp
                245                 250                 255

Phe Gln Gly Val Met Asp Pro Ser Gly Ser Leu Arg Phe Ser Lys Lys
            260                 265                 270

Ala Val Leu His Ala Lys Gly Val Asp Phe Glu Asp Gly Gln Ser Phe
        275                 280                 285

Lys Ile Asn Met Asp Glu Ile Glu Val Leu Gly Glu Leu Gly Lys Gly
    290                 295                 300

Asn Tyr Gly Ser Val His Lys Val Phe His Arg Pro Thr Gly Val Thr
305                 310                 315                 320

Met Ala Met Lys Glu Ile Arg Leu Glu Leu Asp Asp Ser Lys Leu Asn
                325                 330                 335

Gly Ile Ile Met Glu Leu Asp Ile Leu His Arg Ala Val Ala Pro Glu
            340                 345                 350

Ile Val Glu Phe Tyr Gly Ala Phe Thr Ile Glu Ser Cys Val Tyr Tyr
        355                 360                 365

Cys Met Glu Tyr Met Asp Ala Gly Ser Leu Asp Ser Leu Thr Gly Gly
    370                 375                 380

Gly Val Ala Ala Lys Asp Gln Thr Lys Asp Glu Glu Asn Asp Ala Thr
385                 390                 395                 400

Lys Arg Val Pro Glu Asp Val Leu Arg Arg Ile Thr Ala Arg Ile Val
                405                 410                 415

Lys Gly Leu Arg Phe Leu Lys Asp Glu Leu Gln Ile Ile His Arg Asp
            420                 425                 430

Val Lys Pro Thr Asn Val Leu Ile Asn Gly Lys Gly Glu Val Lys Met
        435                 440                 445

Cys Asp Phe Gly Val Ser Gly Gln Leu Glu Lys Ser Leu Ala Lys Thr
    450                 455                 460

Asn Ile Gly Cys Gln Ser Tyr Met Ala Pro Glu Arg Ile Lys Ser Glu
465                 470                 475                 480

Thr Ala Asn Gln Asn Pro Thr Tyr Thr Val Ser Ser Asp Val Trp Ser
                485                 490                 495

Val Gly Leu Ser Ile Val Glu Leu Ala Lys Gly Cys Tyr Pro Tyr Pro
            500                 505                 510

Pro Glu Thr Tyr Ala Asn Val Phe Ala Gln Leu Gln Ala Ile Val His
        515                 520                 525

Gly Thr Pro Pro Thr Leu Pro Pro Gly Tyr Ser Asp Asn Ala Asn Asp
    530                 535                 540

Phe Val Ala Lys Cys Leu Glu Lys Asp Pro Asn Arg Arg Pro Thr Tyr
545                 550                 555                 560

Ala Gln Leu Leu Glu His Pro Phe Leu Val Ala Asp Lys Gly Ala Glu
                565                 570                 575

Val Asp Met Val Gly Trp Val Glu Gly Ala Leu Lys Arg Lys Ala Glu
            580                 585                 590

Arg Gly Ile Ala Ser Leu Asn Pro Ile Gln Pro Pro Val Pro Leu Glu
        595                 600                 605

Pro
```

<210> SEQ ID NO 5
<211> LENGTH: 365
<212> TYPE: PRT
<213> ORGANISM: Cryptococcus neoformans
<220> FEATURE:
<221> NAME/KEY: PEPTIDE
<222> LOCATION: (1)..(365)
<223> OTHER INFORMATION: amino acid sequence of HOG1serotype A H99 strain

<400> SEQUENCE: 5

```
Met Ala Asp Phe Val Lys Leu Ser Ile Phe Gly Thr Val Phe Glu Val
1               5                   10                  15

Thr Thr Arg Tyr Val Asp Leu Gln Pro Val Gly Met Gly Ala Phe Gly
            20                  25                  30

Leu Val Cys Ser Ala Lys Asp Gln Leu Ser Gly Thr Ser Val Ala Ile
        35                  40                  45

Lys Lys Ile Met Lys Pro Phe Ser Thr Pro Val Leu Ser Lys Arg Thr
    50                  55                  60

Tyr Arg Glu Leu Lys Leu Leu Lys His Leu Arg His Glu Asn Ile Ile
65                  70                  75                  80

Ser Leu Ser Asp Ile Phe Ile Ser Pro Leu Glu Asp Ile Tyr Phe Val
                85                  90                  95

Thr Glu Leu Leu Gly Thr Asp Leu His Arg Leu Leu Thr Ser Arg Pro
            100                 105                 110

Leu Glu Lys Gln Phe Ile Gln Tyr Phe Leu Tyr Gln Ile Leu Arg Gly
        115                 120                 125

Leu Lys Tyr Val His Ser Ala Gly Val Val His Arg Asp Leu Lys Pro
    130                 135                 140

Ser Asn Ile Leu Val Asn Glu Asn Cys Asp Leu Lys Ile Cys Asp Phe
145                 150                 155                 160

Gly Leu Ala Arg Ile Gln Asp Pro Gln Met Thr Gly Tyr Val Ser Thr
                165                 170                 175

Arg Tyr Tyr Arg Ala Pro Glu Ile Met Leu Thr Trp Gln Lys Tyr Asp
            180                 185                 190

Val Ala Val Asp Ile Trp Ser Thr Gly Cys Ile Phe Ala Glu Met Leu
        195                 200                 205

Glu Gly Lys Pro Leu Phe Pro Gly Lys Asp His Val Asn Gln Phe Ser
    210                 215                 220

Ile Ile Thr Glu Leu Leu Gly Thr Pro Pro Asp Asp Val Ile Gln Thr
225                 230                 235                 240

Ile Ala Ser Glu Asn Thr Leu Arg Phe Val Gln Ser Leu Pro Lys Arg
                245                 250                 255

Glu Lys Val Pro Phe Ser Thr Lys Phe Pro Asn Ala Asp Pro Val Ser
            260                 265                 270

Leu Asp Leu Leu Glu Lys Met Leu Val Phe Asp Pro Arg Thr Arg Ile
        275                 280                 285

Ser Ala Ala Glu Gly Leu Ala His Glu Tyr Leu Ala Pro Tyr His Asp
    290                 295                 300

Pro Thr Asp Glu Pro Val Ala Ala Glu Val Phe Asp Trp Ser Phe Asn
305                 310                 315                 320

Asp Ala Asp Leu Pro Val Asp Thr Trp Lys Val Met Met Tyr Ser Glu
                325                 330                 335

Ile Leu Asp Phe His Asn Leu Gly Asp Ile Ser Gln Asn Glu Ala Glu
            340                 345                 350
```

```
Gly Pro Val Thr Gly Glu Val Pro Ala Ala Pro Ala Ser
        355                 360                 365


<210> SEQ ID NO 6
<211> LENGTH: 1090
<212> TYPE: PRT
<213> ORGANISM: Cryptococcus neoformans
<220> FEATURE:
<221> NAME/KEY: PEPTIDE
<222> LOCATION: (1)..(1090)
<223> OTHER INFORMATION: Amino acid sequence of ENA1(CNAG_00531.2)
      serotype A H99 strain

<400> SEQUENCE: 6

Met Ser Ser Glu Lys Gly Gln Ser Asn Thr Asn Glu Lys Gln Leu Ile
1               5                   10                  15

Asn Arg Ala Asp Thr Gly Lys Thr Ala Val Ser Asp Ser Pro Leu Pro
            20                  25                  30

Phe Lys Pro His Thr Ala Leu Ser Gly Lys Ile Leu Glu Ala Leu Gly
        35                  40                  45

Ser Asn Val Thr Ser Gly Leu Ser Asp Asp Glu Ala Ser Arg Arg Leu
    50                  55                  60

Gln Gln Tyr Gly Pro Asn Arg Leu Lys Pro Pro Glu Arg Pro Ser Ile
65                  70                  75                  80

Leu Lys Ile Ile Ala Arg Gln Val Gly Asn Ala Met Thr Leu Val Leu
                85                  90                  95

Ile Ala Ala Met Ala Thr Ser Leu Gly Thr Met Asp Trp Ile Ser Gly
            100                 105                 110

Gly Val Ile Ala Ala Leu Val Ile Leu Asn Val Ser Val Gly Ala Tyr
        115                 120                 125

Thr Glu Trp Gln Ala Glu Lys Thr Val Ala Ser Leu Glu Ser Val Gly
    130                 135                 140

Ala Pro Gln Ala Thr Val Val Arg Thr Arg Asn Gly Ser Arg Glu Ala
145                 150                 155                 160

Thr Val Lys Ile Ile Pro Val Glu Glu Val Val Pro Gly Asp Ile Ile
                165                 170                 175

Gln Leu Lys Asn Gly Asp Ile Val Pro Ala Asp Gly Arg Ile Leu Asp
            180                 185                 190

Gly His Leu Ser Asn Leu Glu Ala Asp Glu Ala Phe Leu Thr Gly Glu
        195                 200                 205

Ser Leu Pro Val Ala Lys Gln Thr Glu Pro Ile Asp Glu Glu Asp Cys
    210                 215                 220

Pro Val Gly Asp Arg Val Cys Met Val Phe Ser Gly Ser Gln Ile Thr
225                 230                 235                 240

Lys Gly Arg Ala Arg Ala Val Ile Thr Ser Thr Gly Met Gly Thr Glu
                245                 250                 255

Ile Gly Lys Ile Ala Gln Ala Leu Glu Ser Lys Ala Lys Asn Lys Asn
            260                 265                 270

Arg Gly Phe Ala Ala Phe Trp Trp Lys Val Lys Val Ile Leu Gly Val
        275                 280                 285

Glu Glu Thr Thr Pro Leu Gln Ile Lys Leu Asn Lys Leu Ala Tyr Phe
    290                 295                 300

Leu Leu Ala Cys Ala Leu Val Ile Ala Val Ile Val Val Ala Ser Thr
305                 310                 315                 320

Gly Phe Asn Asp Val Pro Leu Ser Ile Ala Thr Tyr Ala Val Ala Ala
                325                 330                 335
```

```
Ala Val Ser Ile Leu Pro Ala Ser Leu Ile Ala Val Val Ser Leu Thr
            340                 345                 350

Leu Ala Arg Ala Ser Thr Asp Leu Ala Ser Arg His Ala Leu Val Arg
        355                 360                 365

Arg Met Asp Ala Ile Glu Ala Leu Ala Gly Val Glu Asn Val Cys Ser
    370                 375                 380

Asp Lys Thr Gly Thr Leu Thr Val Gly Arg Met Val Val Arg Lys Val
385                 390                 395                 400

Trp Val Pro Ala Leu Asp Trp Arg Pro Asn Glu Phe Ala Pro Leu Asp
                405                 410                 415

Thr Ser Gly Gly Gln Ala Tyr Ser Phe Glu Thr Gly Ser Asp Pro Phe
            420                 425                 430

Tyr Pro Arg Gly Glu Val Leu Ala Asp Ser Gln Lys Ile Thr Gly Thr
        435                 440                 445

Ala Glu Thr Leu Asp Leu Lys Gln Pro Arg Asp Gln Ser Asp Ser Ser
    450                 455                 460

Ser Ser Asp Ser Asp Pro Asp Glu Arg Asp Val Glu Glu Gln Glu Arg
465                 470                 475                 480

Val Ile His Val Glu Asp Met Glu Asn Asn Leu Arg Asp Leu Ala Leu
                485                 490                 495

Cys Ile Ser Leu Cys Asn Gln Ala Thr Leu Thr Arg Pro Val Asn Gln
            500                 505                 510

Asp Gly Gln Trp Glu Ala Asn Gly Asp Pro Thr Glu Thr Ala Leu Gln
        515                 520                 525

Val Ala Ala His Lys Leu Gly His Gly Lys Pro Phe Leu Thr His Ala
    530                 535                 540

Ala Lys Pro Ser His Arg Ala Asp Ser Ile Arg Ser Gly His Ser Ser
545                 550                 555                 560

Arg Pro Leu Val Ala Gly Ile Arg Gly His Phe Val Pro Ile Ile Glu
                565                 570                 575

His Pro Phe Asp Ser Thr Val Lys Arg Met Ser Ile Ala Tyr Lys Phe
            580                 585                 590

Val Ser Glu Asp Pro Gln Asp Ser His Ile Leu Cys Leu Leu Lys Gly
        595                 600                 605

Ala Ile Glu Arg Val Phe Glu Arg Cys Thr Lys Ile Gln Gly Gln Pro
    610                 615                 620

Ile Thr Glu Glu His Lys Lys Asn Ile Met Val Lys Val Asp Ala Leu
625                 630                 635                 640

Ala Ala Gln Gly Leu Arg Val Leu Ala Leu Cys Gly Lys Arg Leu Pro
                645                 650                 655

Val Ser Met Val Asp Glu Val Lys Ser Thr Pro Arg Asp Ala Phe Glu
            660                 665                 670

Ala Asp Phe His Phe Leu Gly Leu Ala Gly Ile Phe Asp Pro Pro Arg
        675                 680                 685

Lys Glu Ser Ala Gly Ala Val Ala Asp Cys Phe Arg Ala Gly Ile Thr
    690                 695                 700

Pro Arg Met Leu Thr Gly Asp His Pro Ala Thr Ala Thr Ala Ile Ala
705                 710                 715                 720

Leu Asn Ile Gly Ile Leu Asp Lys Thr Tyr Ser Lys Asp Ser Val Met
                725                 730                 735

Thr Gly Gln Gln Phe Asp Ser Leu Ser Glu Asp Glu Ile Asp Gln Leu
            740                 745                 750
```

-continued

```
Pro Glu Leu Pro Leu Val Val Ala Arg Cys Ala Pro Glu Thr Lys Val
        755                 760                 765

Arg Met Val Asp Ala Ile His Arg Arg Gly Gln Ser Thr Val Met Thr
    770                 775                 780

Gly Asp Gly Val Asn Asp Ser Pro Ala Leu Lys Arg Ala Asp Val Gly
785                 790                 795                 800

Val Gly Met Gly Thr Gly Ser Asp Val Ala Lys Gln Ser Ala Arg Ile
                805                 810                 815

Val Leu Ser Asp Asp Asn Phe Ser Thr Ile Ile Arg Ala Ile Arg Lys
            820                 825                 830

Gly Arg Ser Val Phe Lys Asn Leu Ser Lys Phe Leu Leu Tyr Leu Leu
        835                 840                 845

Ser Gly Asn Leu Ala Glu Ile Ile Val Leu Met Ile Gly Leu Ala Phe
    850                 855                 860

Lys Asp Asp Asn Gly Gln Ala Val Phe Pro Leu Ser Pro Val Ala Ala
865                 870                 875                 880

Leu Trp Ile Asn Thr Leu Ala Ala Gly Pro Pro Ala Leu Ala Leu Gly
                885                 890                 895

Leu Glu Pro Thr Ala Ile Asp Ala Met Glu Gln Gly Pro Glu Val Tyr
            900                 905                 910

His Arg Ile Phe Thr Leu Glu Phe Tyr Val Asp Leu Ile Phe Tyr Gly
        915                 920                 925

Phe Leu Met Gly Ser Ile Ser Leu Val Asn Phe Val Ile Val Leu Trp
    930                 935                 940

Gly Tyr Tyr Pro Gly Asp Leu Gly Arg Leu Cys Asn Glu Asp Asp Pro
945                 950                 955                 960

Ser Ile Cys Asp Pro Val Tyr Gln Ala Arg Ala Ala Cys Phe Ala Thr
                965                 970                 975

Leu Val Ile Val Leu Met Ile His Ala Leu Glu Cys Lys His Leu Ser
            980                 985                 990

Lys Gly Leu Ala Gln Ile Asn Leu  Arg Asp Asn Lys Val  Leu Leu Trp
        995                 1000                1005

Cys Val  Val Ala Leu Ser Leu  Ser Thr Phe Pro Val  Val Tyr Ile
    1010                1015                1020

Pro Val  Ile Asn Asn Lys Val  Phe Leu Leu Asn Gly  Pro Arg Trp
    1025                1030                1035

Glu Trp  Gly Ile Ile Phe Gly  Met Ile Leu Val Tyr  Leu Ser Ala
    1040                1045                1050

Thr Glu  Leu Tyr Lys Trp Ile  Lys Arg Ile Trp Ile  Arg Arg His
    1055                1060                1065

Ala Pro  Pro Ser Lys Gly Pro  Ser Asp Lys Thr Leu  Arg Met Glu
    1070                1075                1080

Ser Thr  Ile Ala Pro Pro Val
    1085                1090
```

```
<210> SEQ ID NO 7
<211> LENGTH: 916
<212> TYPE: PRT
<213> ORGANISM: Cryptococcus neoformans
<220> FEATURE:
<221> NAME/KEY: PEPTIDE
<222> LOCATION: (1)..(916)
<223> OTHER INFORMATION: Amino acid sequence of NHA1 (CNAG_01678.2)
      serotype A H99 strain

<400> SEQUENCE: 7
```

-continued

```
Met Thr Ala Phe His Pro Phe Glu Val Asn Ala Pro His Leu Ala Tyr
1               5                   10                  15

Thr Phe Leu Gly Gly Phe Val Val Ile Phe Gly Met Ile Ser Leu Phe
            20                  25                  30

Ile Lys Glu Lys Leu Tyr Val Gly Glu Ala Pro Ile Ala Thr Val Val
        35                  40                  45

Gly Ile Ile Ile Gly Pro His Cys Leu Asn Phe Phe Asn Pro Ala Gly
    50                  55                  60

Trp Gly Gly Gly Glu Glu Glu Val Ala Ser Asp Val Thr Leu Glu Phe
65                  70                  75                  80

Thr Arg Val Val Ile Ala Ile Ser Val Phe Ala Val Gly Val Glu Leu
                85                  90                  95

Pro Lys Ala Tyr Met Lys Arg His Trp Arg Ser Leu Phe Phe Leu Leu
            100                 105                 110

Gly Pro Cys Met Val Trp Gly Trp Met Ile Ser Ala Leu Leu Ile Trp
        115                 120                 125

Gly Leu Ile Pro Asp Leu Thr Phe Leu Ala Ser Leu Val Val Ala Ala
    130                 135                 140

Gly Val Thr Pro Thr Asp Pro Ile Leu Ala Gln Ala Val Ile Gly Gly
145                 150                 155                 160

Lys Phe Ala Asp Lys His Val Pro Ala His Ile Arg His Leu Leu Ser
                165                 170                 175

Ala Glu Ser Gly Ser Asn Asp Gly Ala Ala Phe Pro Phe Leu Tyr Ile
            180                 185                 190

Ala Leu Tyr Leu Leu Leu Asp Ala Ser Pro Gly His Ala Val Gly Glu
        195                 200                 205

Trp Phe Tyr Met Thr Trp Val Tyr Glu Ile Ile Leu Gly Val Ile Ile
    210                 215                 220

Gly Ala Ile Leu Gly Phe Cys Ala Arg Lys Leu Met Lys Leu Ala Glu
225                 230                 235                 240

Arg Lys Arg Leu Ile Asp Arg Gln Ser Tyr Val Ala Gln Tyr Val Ser
                245                 250                 255

Leu Ala Val Leu Ser Ile Gly Val Thr Ser Leu Leu Gly Ser Asp Asp
            260                 265                 270

Leu Leu Ser Ala Phe Ala Cys Gly Cys Ala Phe Ala Trp Asp Gly Phe
        275                 280                 285

Phe Asn Lys Ala Thr Glu Asp Ala Val Phe Ser Asn Val Ile Asp Leu
    290                 295                 300

Leu Phe Asn Cys Ala Ala Phe Ile Tyr Ile Gly Ala Ile Ile Pro Phe
305                 310                 315                 320

Asn His Phe Asn Asp Leu Pro Asp Leu Arg Val Trp Arg Leu Val Val
                325                 330                 335

Leu Ala Ile Leu Ile Leu Leu Val Arg Arg Leu Pro Ser Ile Ile Ala
            340                 345                 350

Cys Tyr Lys Phe Val Pro Asp Ile Lys Thr Phe Arg Glu Ala Leu Phe
        355                 360                 365

Thr Gly Trp Phe Gly Pro Met Gly Val Gly Ala Val Phe Ile Ser Thr
    370                 375                 380

Leu Ala Arg Ser Ser Leu Pro Glu Gly Glu Pro Glu Gln Asn Thr Glu
385                 390                 395                 400

Ala Val Asp Arg Leu Lys Asp Val Ile Met Pro Val Thr Leu Phe Leu
                405                 410                 415

Val Leu Ser Ser Ile Val Thr His Gly Met Ser Ile Pro Phe Phe Ser
```

-continued

```
            420                 425                 430

Leu Gly Arg Arg Val His Ser Ile Thr Tyr Thr Arg Ser Arg Asn Leu
        435                 440                 445

Ser Met Asp Thr Arg Gly Asp Glu Pro Ala Trp Thr Thr His Ala Arg
    450                 455                 460

Arg Ile Ile Pro Gly Gln Glu Ile Ile Val Asn Arg Asp Asp Asp Asp
465                 470                 475                 480

Glu Glu Gly Asp Leu Gly Val Arg Arg Met Asp Thr Leu Thr Ser Asp
                485                 490                 495

Ser Asn Gly Arg Ile Arg Glu Lys Ile Glu Glu Glu Asp Ser Gly Glu
            500                 505                 510

Ser Ser Ser Ser Arg Thr Arg Gln Gly Glu Met Ile Glu Met Thr Glu
        515                 520                 525

Lys Arg Gly Pro Ala Arg His Gly Ser Gln Ala Ser Gln Gly Glu Ala
    530                 535                 540

Ala Glu Glu Gly Glu Arg Trp Arg Ser Ser Gly Glu Glu Ser Ser Asp
545                 550                 555                 560

Leu Ala Asn Asp Pro Glu Thr Gln Arg Glu Val Glu Glu Gly Met Glu
                565                 570                 575

Glu Val Glu Asp Lys Glu Gly Gly Gly Arg Arg Thr Pro Pro Leu Ala
            580                 585                 590

Lys Tyr Arg Glu Gly Asn His Leu Ile Val Glu Arg Lys Val Lys Asp
        595                 600                 605

Ser Asp Glu Val Glu Val Glu Val Ile Arg Asn His Phe Ser Asp Asn
    610                 615                 620

Lys Lys Thr Glu Ser Asp Arg Phe Thr His Pro His Arg Leu Lys Ser
625                 630                 635                 640

Arg Glu Leu Asp Asp Leu Leu His His Leu Pro Lys Ser Leu Glu His
                645                 650                 655

Ala Thr Ser Arg Val Gln Asn Gly Gly Lys Asp Ala Val Asp Arg Leu
            660                 665                 670

Gly Leu Gly Leu Met Ala Ile Asn Thr Pro Glu Pro Ser Pro Ser Ile
        675                 680                 685

Glu Ser His Gly Gly Pro Arg His Asp Tyr Val Asp Gly Leu Glu Arg
    690                 695                 700

Thr Gln Ser Pro Glu Gly Leu Ala Asp Glu Asp Arg Asp Ser Glu Gly
705                 710                 715                 720

Arg Gly Asp Val Ser His Gly Gly Asp Tyr Glu Glu Asn Glu Ala Asp
                725                 730                 735

Tyr Glu Asp Val Pro Asn Glu Thr Arg Arg Gln Arg Arg Lys Lys Met
            740                 745                 750

Lys Pro Pro Ala Ile Val Val Ser Arg Gln Asn Ser Ala Gly Leu Pro
        755                 760                 765

Arg Arg Ser Ile Arg Ser Arg Leu Phe Gly Arg Arg Gln His Ser Ser
    770                 775                 780

Asn Ser Pro Ser Arg Ala Glu Glu Gly Leu Ala Pro Pro Asn Pro Ser
785                 790                 795                 800

Leu Leu Val Pro Ser Ser Ser Pro Ser Arg Pro Gln Asn Ile Ala Ala
                805                 810                 815

Glu Pro Glu Ser Ile Leu Ala Glu Asp Ser Arg Gly Ser Ser Ser Pro
            820                 825                 830

Ser Gln Ser Gln Asn Leu Ala Ile Pro Leu Thr Arg Thr Leu Ser Ala
        835                 840                 845
```

```
Ser Arg Ser Ser Pro Ala Val Arg Phe Ala Asp Asp Ala Ser Pro Ser
    850                 855                 860

Ser Asp Thr Ala Pro Gly Gln Ser Asn Tyr Gly Thr Asn Ala Pro Gly
865                 870                 875                 880

Phe Lys Lys Asn Pro Ala Leu Ala Met Tyr Arg Ser Ala Ser Val Gln
                885                 890                 895

Ser Thr Gly Ser Asn Lys Asp Gly Pro Ser Val Ser Phe Lys Glu Pro
            900                 905                 910

Glu Ile Lys Arg
        915


<210> SEQ ID NO 8
<211> LENGTH: 4121
<212> TYPE: DNA
<213> ORGANISM: Cryptococcus neoformans
<220> FEATURE:
<221> NAME/KEY: gene
<222> LOCATION: (1)..(4121)
<223> OTHER INFORMATION: genomic DNA sequence of SSK1 serotype A H99
      strain

<400> SEQUENCE: 8

atgtggggct caaatgcttc catcgccgcc tcggagtcga ccgactccct ttcccccgcc     60

ccctcccagt ctgccgccgt agagttcccc ctgcccgtaa gctcccgccc gtctctcact    120

tccgccgctc accccctccca gatgtccgct tcctcctcct ccacctcctc ccagcctctc    180

tttgattggc gcattcccaa gcccacctca ccccgcacac gcatggaccc attcgacact    240

tttgatcctg tatcctcaag ctcagaggat gatccggtcc ctcaagagag ccgccgtgct    300

ggtcatcagc gctccgtaac agatcctctt ttacgagatg gccaacccct cgatatggag    360

ttcactactg ccgggccgcc tatacagagc tacgactttg aacaaccgcc cacgtttagc    420

agaacgttat cttcccctct tccagctaaa gtcggctcgc ttagacaccc tatgccattc    480

accattgacg atttaagctc tcgcaatgtg aattcaaccc atcgtccgca gccgactaca    540

cctctgcatt ccatatccgt tgagttagcc gattccttgc aatcggccat tcaaacatta    600

ctgcatctgt ccccacctca cctactcgat aacgcaaaag aacagtactc tggatgcacg    660

gtacagatac ctgctacctc gctttcggcc cttttgacct ctatgagagg cctcaacttc    720

ttgtcggcgc atgctgaaga actggtcgac atgagtgcac gtggagatcc acctgtactc    780

catcaagaag acttcgatgt aggagaactt ttgcaaaacg ttgcggatat gttgagtgga    840

gaagcagcag aaaaacggat tgatttcgtt ttgttccatg gcgacgtagc gatgaggcat    900

gtcagtgtgt atggagattc tgatggaatt agctatacct tgagtcatgt aagtcctaca    960

tgcacctgct gcatactgac aaacaggtta ttcgacaaat actggcagta gccaattacg   1020

atgataccat agaactcggc cttcaagtca ttcctcaaag tccatcttta gcttccgccg   1080

tcggacttcc tctaacctct gccgatgtta gtggaggagg tggtgtcaag tcagcgtcca   1140

catctcggtc aggctccccc aataacagtc tctctcgatc taattctgtc catgacgggc   1200

cccttctctg tgtgttcgaa atagtacata acatctatca gccaccacca agctcggcat   1260

ccgccactcc taaagccgag ctgaaccctt tcactcatct tgctgaagaa accgaagcct   1320

tgaaaccaag attggataca gcattttgca aaaacctgct tcatcggcaa aatgctgtcc   1380

tcaaagttga tgtgcagcct tcatctcctt taggatccgg gatgccccgt agagcttacg   1440

cgttatcagt gctcctacca agaggtaaac ccatcactga gcctgcaata ctttctaaag   1500
```

-continued

```
aggaacaaga agttcgtcaa ccattttcat cccacgtact tgcacgagaa cccaccctca   1560
atgagctctc ggaatttgct gaatcattac gaggaagaaa ggtgtttatc catgccaatt   1620
tgagtagtgt tttcgcgaga cacctcacga gctacctagc tgcatgggga atggatatat   1680
cgcatctacc gacagatggc gatgaggctg ataaattgaa ggatgtcgcg gccaaacatg   1740
actcggctta tactggatct atgggtgtgt caggcggcac tacttccagc gcagaaacgc   1800
cctattcaat taaaccgacc ggcgtgactg ctgttcaacc tggacacttt gtcattatcg   1860
acgatgatgt tgcggtcttg cgccgtgaac tcgtgcgcat ccgttcagaa ttacttccca   1920
ttctctttaa acctagactg tcaaagcgtc ccactatgac ttctcgaacc cgttccaccc   1980
cttcattgcg acaggtcccc ccaaggtcat catcgggttc tgtacttata cactttacct   2040
ctcttgccaa ttataaccga gttcgagacg cgattgcgag ctttgtgggg gcgccagggt   2100
taaccaatcc ggaaacttat gttcagccgg aggtgatagt gatacccaag cctgttggac   2160
cacgaagatt tttgactgct ctgcataccg ctgtgaaaca gcctatggtt gacccatttt   2220
tctcccctat cgccacatct cctagatcac caggcggagg ttactttggt ggtttgcgga   2280
ctccgacgga gagagaatca ggattctttg attctgttgc agaagaacca catgaagagg   2340
cggattcgcg accagattat gccacggtgc agaaagccag atctccttta ggagaatttc   2400
cgccttctgc ggcacagatc gttcgtacca accaaggctt gcatctttcg cttcccactc   2460
caaatgaaat tatgacaacg cctgctccag aatatttttc tgggtcttcc aagtctccta   2520
gctctggtgc gtccggagtc gtgatgcaga gccctgatgg tcgtcctttc ggaatgtttt   2580
tcgaaccgcc cataaaaaat gagcgccgcg gatctactca caggacgcct tccgattcca   2640
tcaggaggaa acaagcgaac cgccgtgcgt ctacaagtga tgaacccttt tcttcacctt   2700
ctaccgccct acctccccgt cgctcgtcca caatttctac gactggcaat gaggaacacc   2760
gcagttcacc tatcgctaac gtcacagacc gtcctaccca ttcaagggta aattcaagaa   2820
ggaagaacaa tcttccggcg gcggagcaac ctattttggc tgtgggcagg gcaaaaggca   2880
gggaaagatc ggagactgtc acgaagggag gggacctcgg gtcgagaaaa ggtacaccag   2940
cggcaagccc acgtatagag gagaagaagg aattggaaag aggcgagaag actaaaagcc   3000
tggctccttc aactgctcct acgaagaaga atgctaaagt cgatgttgtg gtgccgccca   3060
tcaacgtgct gattgttgaa ggtaaatctt ccattcaaat gatttgttca aacaccgact   3120
gacagataac tagacaaccc catcaatcaa aacattttga gtatgttcct gagaaaaaag   3180
aagataaaga attcctcggc caaggatggc gcagaagctg ttgaaaagtg gaggactgga   3240
ggcttccatc tgattctggt aggctatgat ctctttcttt gattcgtgca gtacttattg   3300
gacccttcgc agatggatat ccaattgccc gtcatggatg gcatagctgc taccaaagag   3360
attcgtcgac ttgaacgtca caataacatt ggcgtttttc catcgactcc agcggccgaa   3420
cttcctcggg gtcaaaatgt tgcggattct ccaccaccat cttctccatt tcgctcgtca   3480
gttatcattg ttgccctgac agcctcgtcc ttgcaaagcg acagagtagc tgctttggct   3540
gctggctgta atgacttctt gaccaagcct gtgtctttga aatggttgga caaaaagatt   3600
gtggaatggg gttgtatgca ggttagtgat ctcttctttt tttttgatta tagctgatct   3660
aaatataggc attgattgat tttgacggct ggcgacgatg gaagagctcc gataccaaga   3720
atcctagcga aactaagcag ggcttctcag tgggccctca acaggctgct aggtcgcttg   3780
ctagcagact acgtattgaa cgcaaaggat ctcgatctcc ggcagctcca gtatcaaccc   3840
cgcgactcaa tttgcagtcg gcaaccccag ataggccaga aaccccccca gattccacgt   3900
```

cacaaatgcc aaaggccccg cccgttgcag cctctgaccc cccgttatct cccaagtcgc 3960
tgaacaagac agttaatgat gtcttcgagc aagcagacgc tagactcgaa aatgcgcggg 4020
aggaacaagg agtatcaagt caaaaggaaa acacaagctt aacagattca acaaacacca 4080
ccattacgcc ctcaaagacc tatccggctc ctcccccatg a 4121

<210> SEQ ID NO 9
<211> LENGTH: 5666
<212> TYPE: DNA
<213> ORGANISM: Cryptococcus neoformans
<220> FEATURE:
<221> NAME/KEY: gene
<222> LOCATION: (1)..(5666)
<223> OTHER INFORMATION: genomic DNA sequence of TCO2 serotype A H99 strain

<400> SEQUENCE: 9
atgatcttag gaaccgacat cgacctgtcg tctataccaa cggcgtttct cgaggtgtgt 60
atcgctgtcc ctttcgagtt gcaccatgaa gctgaccatg agaacgcatt cgccgccaac 120
ttccaaatct gttctgggct tgtcttttgg acaaccatct aggcttatcc cttcccagcg 180
gttgtgttcg tgatcgattc tccccctagc ccaagaccgc ggctccattc cagaaataca 240
gacacgacca ttcggcgaac ggatggccaa atatcgcctc ttacaggtcc tccagtgcaa 300
cagttcgcgt cagcgcccgt ggtatggggc aatcaacgat ggcacgagct ggctcagggg 360
aaaacaattg cagagtgcgt ggatgtggcg tcacagaaca agctgcaaac ttgggtggaa 420
aatgacaccg gtgacaagtc ggagagtttg gccctggacc tgaaggtgcc gcaaggcgtg 480
actcttcatc tggcaaagac catattgcca ttaagtccac cgtcctcctc tcagtcactt 540
tgcatcctta tatcgcaata tatcgataag ccggaaagtt tcgcgccacc aatctcatct 600
ggagatattc ttttctcttc tctatcgcga ctctcccaga ctttttctcg gtcatcctct 660
ttttcatcca accctagaaa atcgattgat gtccctgcgt cactatccga acaccggggt 720
tctgctacat cgacaagtag caatctgcgc tcttcgatcg atttgacttc ccctaattct 780
caaccctctc cactaaaccg tgaacaaagc acgtacttca cccatggctc cgcgaccaga 840
gaagagcgac cctcagtaag gcgtagacgg tcaccgccaa tctcaatgac gaggcccaag 900
cctcttgaga gccatgctca agaatgctgg gacttggtag agaatttcga ctggtcaaaa 960
acagcattag ggccgagaga acagtggatg gatgcgttag atcctgttct ggcaatcaca 1020
tttgaatcca gaacggcaga ttgtgcctgg ttagggcctg atctagagct agtttagtga 1080
gatactatcc gtcttgcaaa aataatggcg actaactttt atgatcagca ataaggcgta 1140
tcaagagctg gttgaccatc ccaatgcttt tggaaaacct gcaagacaag tttgggctac 1200
caattgggac tacttggaac ccctggtcaa gcgatgtctc agtgggaccc cggtctacaa 1260
ggacaacgac ccgcttttct ggcgtcgata cggcaatggt cgacttctgg aacattacca 1320
cacttggcga tatgtcccga taacgggcaa agatggctca gtgcttggca tcttcaacca 1380
gtcaattgag gtcaccgact cagtactgct agagaggcga atgggcacga ccagggaact 1440
ttcggaacac atgtcgttta ttcgtacaac tgaggacttt tttagctcgg ttgccgacgt 1500
ctttagtcag aaccctactg acataccgtt cgcactttgt taccgggtcc gacaagttga 1560
caccgatggg acatttgtcc atttggacgt ctcgcttcag tcgtccgtcg gtgtacccga 1620
aggccatccg tctgctccag atcaaattcc cgtcagcttc ttaaatggta acccttaccc 1680
tagcaatgtc gagcgatcat tttctcctgc tttctcaatc gtttcaatcc actcttcgag 1740

```
cagtcatcga gtctgtcacg tctctgaaga cactacacaa tggcccatcg ccaaagccct   1800
acaaaggcgg caatgtgtca tcatcgaaga atgttcgcaa ttaatagaag gatatcctat   1860
ccgtcgctgg gatgggcttc cattctcagc cattgtcgtg cccatatgct ctgaagggtc   1920
tcccgaaatc cctgacgccg ttgttattct tggtctcaat gtgcgacgtt gttttgacca   1980
tgaatacgat tcctggattc actctattcg gtcacaacta tcttcggccc tcgtgatggt   2040
caaggcgcgt gaagctgaac aaaagatggt tgaggaaagc gcacgtatgg agaaagcaaa   2100
agtcgcttgg ttcagaggag ccgcgcacga ccttcgtagt ccattaaccc tcgtcgctgg   2160
accgcttgcc gatgtgcttg attcggattt gaactcgagt cagcgcacgg ctttgaccgt   2220
tgcgcaacgc aatcttgatc gtttagtgcg cttggtcaac gccctcatgg atttctcgag   2280
ggtggaagct ggacgaatgg aaggacgatt tgttccgacg aacttgagtc aattcgtgac   2340
acagttggca gctcttttca agcctgcaat agaaagattg gggttagaat acgtactaga   2400
tgtccagcca agcgaggagc ttgttttcat cgatcctgtt ctgtttgaga ccgtggtatc   2460
aaaccttatt ggcaatgcgc tcaaatacac tgaaacgggt tctatcactg ttcgggtgca   2520
atacacggat tacgcagagg tctcggtcat cgataccggt gtgggtatac cgaaaaatga   2580
gctggcactg gtgaccgaat ggttccacag ggcaagtact gccattcact cgggaaccca   2640
gggaacagga ttgggactgg ctttggccaa ggaattgctc aagttgcata aaggagaatt   2700
gcttgtcgag tctcaaaccg ccaatgagtc aggaggtcct catgggtcca tttttacagc   2760
gaaaattcct cttgatttca agccctctcc atcggctcat atcattccgt ccgtcgaatc   2820
tcacaagacg tttggcaaat acagtaaagc cgtcgcagac gaagccatgc gctgggttgg   2880
ggactcagat gccgctagtg aggcgtacga catgtcgagc ggtaccggag tctcaagcgc   2940
tggtagtggc tctggaaaca cgaccacctt cggacccaag tttgcagatg cctttttgtt   3000
tgataagaac gacattgtgc ttattgtgga agacaatgtc gacatgcgtg aatacatacg   3060
acagcttttc gccccttatt gtaccgtact cgaagcttcc aatggtgaac aggcttacaa   3120
tatggctacc caaaaccctc ccaacctcat tttgtcggac gtgctcatgc ccaaattatc   3180
tggtatggag ctactacaaa ggatcagatc ccatcctgac actcgcattg tgcctatggt   3240
ccttatttcg gctattgctg gtgatgagtc tagggttgag gctctgctaa acggcgctga   3300
tgactatctt gccaagcctt tcaaacccaa ggaactcatc gcgcgtgttc acctgcacat   3360
gcaagttggc aagaaacgtg ccaagctcga agcgctatac gcccaacgcg aaacagaatt   3420
gacagctcta tctgactatt gtccgatcgg tatcttccga ggagacaaat atggccatat   3480
tgtttatgcg aacgcagctt ggcgtgcgca gagcggcctt ttggtgggtg accctaacga   3540
ttgggcatct tatgtgcacc cggattcgaa agcgcagctc ttggaacaat ggaatcagtg   3600
gttgaggggg gatttgaagg agttccgagc ggcttggaga tggtctaatg gcatccctgt   3660
caggagcatc ttggtccggt tagatgacgt caaggaaggg ttttctgggt taattgggtg   3720
cgtagtggat gtgtctcatg aagagagacg attaatcgaa gctgaggaaa gaagaaaaga   3780
ggcggaagag agtaaacatc agcaagaact ccttattgac ttgacaagtc atgaaattag   3840
gaccccggtg tcagcaatcc tgcagtgctc agatcttgtt aaagagaatc ttgtagctct   3900
gaaggaccag ttgagaggag cggggccaaa gggctttgtg ccgagtcaag aattactggc   3960
tgatcttgag caggatgtgg aagctttgga aagtaattca ccatcccctt tcatgctaat   4020
ttcgaaacta acagtgattt tgtaaggtat ttatcagtgc ggtcttgtgc aggaacgcat   4080
```

-continued

```
tgccggagat gttctttcgc tggctcgtat ccaactcgat atgctgagtt tgcacgacat   4140
tgacgtcaac ttgcgccgag aaggcaggaa agtttcgtcc atctttgcat cggaagccaa   4200
gatgaaggat atcgacctcc aattggaatt tggacctact atcgaacagt ccaaagtgct   4260
ggccatcaag acagatcccg tgagattagg ccaggtggta acaaatctca tttccaacgc   4320
cattcggttt acatcttcga gtggtgagtt tcatccaacc cataatgtgc tatagtgata   4380
ctgaattgta attcatttag atgtccgaaa gattactatc caatacgacg tatcgtttgt   4440
ccctcctgcc gatgactctt gcgccctccc ttcatctgtt ggcttgcccg acatacttcc   4500
tgtgaaagag aatactccac tatggctgtt tgtcagtgtt accgattctg gacctggtat   4560
gacagagcaa gagttatctg ttttgttcca aaggtttgcc cgtaagtcct aagcccattc   4620
tctttgtcga ggttacgttg acgaatcttg atatctagag ggcaataaga tgattcatac   4680
taagtatggc ggaagcggtt tgggactgtt catctgtcga agtgagtgat tggaggaggt   4740
tttttttttt ttttggtggg gggatacatg atgctgaaac catctacaga gattacagag   4800
cttcttggcg gtcgtatcga agtgctcagc caagtcgggc acggtagtgg tgagtgcccg   4860
tgtgctctgt tatccattgc atgctgctga atcgagtgcc tttcccaagt tttccgattc   4920
ttcattaaaa cgcgcgctgt cgctcctccg tccgccatcg ctgctctcgt agaatcctct   4980
cctctcaaac cggtatccgc cacttcacct tcttcctcgt tagccatgag ccgatcgtct   5040
tctcggagca caaacgtcac tacacctata gagggtggtg ggaccgagca cgtgttgatc   5100
gtggaagata acctaatcaa tcagactgtc ctgaagcgac agctcgtcaa ggcgggttta   5160
tcgtgcaacg gtgagttctc catcccatcc tctgtgattc ccacatttat cttgattgct   5220
gttgtatagt cgcgagtaat ggccttgaag ctcttaatgt catccgtgaa gtccatcggc   5280
aacaccgacg cggtgggccg aaccgtaaaa ggctatttga cgtggtattg atggatctcg   5340
agatgccagt gatggatggt atcaccgccg tacgagagat acgacagtcc gaggccgcgg   5400
ggacattggg caggaatatg gtgattgccc tgacggggaa cgcgagacaa ggacagattg   5460
atcatgcctt ggcttctgga tttgacgatg gtgagttggg aagacccttt tttgggggct   5520
cagaggacga tgtggattat gaacttttct gacacttgat tgtagtcgtc atcaaaccgt   5580
atatcctggt agatttgctg aacaagatca aatctatgaa agttagaaaa ttggagttgg   5640
aaactgcgaa agctcaagaa gagtga                                        5666
```

<210> SEQ ID NO 10
<211> LENGTH: 4744
<212> TYPE: DNA
<213> ORGANISM: Cryptococcus neoformans
<220> FEATURE:
<221> NAME/KEY: gene
<222> LOCATION: (1)..(4744)
<223> OTHER INFORMATION: genomic DNA sequence of SSK2 serotype A H99 strain

<400> SEQUENCE: 10

```
atgtccaacc caacctcccc ctcaaacccc tcagacaccg gcccgtcctc ggcgtccaac     60
gtcacatcct cgtcctcaaa gaccggacgc agatcagtgc gcctctttgc cccagacgag    120
gaggacagct cagacgagga cggcggcctc atcggcgtgc ccgcagagac cacattcaag    180
gacgacgaga gtgagtagat acgcaggaac caaatgcagc gcatactcac actccacagt    240
ccctccttcc aacccacgtt ccgcctccta ccccgggcca ccggcacaca cctccccccac    300
ctctaaaatc tcaaccatcg tttcgtccgc ttctgcagcc cagccaaaac ttgcacgttc    360
```

-continued

```
aataacatac gtcgcaccca atgccgtctc ctcccggccg gcatatcccc tcaatcccgc    420
agggtcagaa accttacacg cctcgtacga gacatggcga aaaacgcgat ataccctcga    480
gtcattcggc agaggatcca aaccagacgg gaagaatacg gcacaaagag gaaggtcgta    540
tactgacccc gatataggat actttagcca cgatgcagga gatgatggtt ggggctcaga    600
tgatgacgac gaattgagat cccctggctg gggcatatcc catcataaca tggactctgg    660
aggcaagacg aacgggtcac cacagttgcc tataaagccc gccgatgtca ccgaggatga    720
aggacaggaa cgtttagatt ggcaaggcat gctggaaagt gtcctcaact cggatgttct    780
caaggtggag gaacaacgta tctacaattc catgccgaca gattcattca gagaagagat    840
tggaaagacc ctttggtggc aaatccgtgc caaactgcgt gggaggacag aggcggagga    900
gaagaaacgg gtgcaagagc gacgagcgag agtggtggac ccggtgctgg aagagataaa    960
cgagttcaag tacgacccaa aaaataaccc agaaggcgaa gaagacagtg atggcgatcc   1020
gcaagacgcg acttcgactg ctgcacccca atccaaagct ctcaatcaag tcaacaccgt   1080
tctcgccaaa cttcatgcaa tcaaaggtct ttatcccaac ctcgcagcca tgcgagccga   1140
caaggttctc tataccgatg aaaatttccg caaacgcgcc gacgcattga cctcttggtc   1200
catcatcgtt tcatccctcc aaacccagct caaactcttg caaaaatgga caggttccga   1260
tgagcttgac atcaccaagc ccaacacgac ccacgagaaa gcattggtcg gcaagtacaa   1320
gtatcactct atcgacagca agggtacgcc cggcagggat gcagccgatg actcgagttt   1380
cctcgatcgt gtgataaaag aagataacct tcaacggaca ttcgagcgtc gagcgtttgt   1440
agacatgatc aacctcgtgc gcaacgccaa ggagacggtc atcagctatc tcccccagtt   1500
ccaagaacaa aatcttcccg atttccagta cgaaatcgtt cgtcttattg gtttccccgg   1560
tcgacttatc attgaagctg tcaaggttcg tttggatgct gcatcccgac tacttgaccc   1620
gaaccctatg gtcgtcgaag actttatcga aaaccttcgt ctatccattt cgctcgccgt   1680
gctaatccgg aaacaatacg acgaaatcat ggcacccgat gccgagggga gatggaaaat   1740
cccgcattgc ttgccgacag agtacaatga tgttctgctc gatgcgctga ggacattttt   1800
caaattgttg cattggagat tacgaggagt ggggaaagcg agttattaca aggaaacaga   1860
agtgttggaa gaagaggcgc cgttcttgta tgaagcggcg gaggctattg taggcggtga   1920
tatggttgtt gcagagcagt attggtgagt ttgaaatcgt atcatcctgg caaggagctt   1980
agtgctaagt atcgatgtaa atagcgcgtt atccaacaag ctccttatac gttcagcaaa   2040
ttatcttgac cagcaacttc gggtaccaat acattccccg tctcgcgaca aggaacgtgg   2100
tgacaaggag cgcgatggct cttcgtcttc tcaacgtaac cgtgacggcc gtgatagctc   2160
gctgcccggc ccaccgaaac acatgaaagt cgaagaactc ttctcatggt actccaaact   2220
ccttgattcc gctcgtatgc gacaccgtaa aacccaacgt ttctgtcgta aactcaccca   2280
acgattcgat aattccgccg aatattcaat cgaggagacg gagatggaca tgctggtgga   2340
gacattgcaa gatactggtc atttcttggt atataccggg aaatttgagg cgaatgggac   2400
gtatatcgtt gcggatggga gtctctgggg tcagccggac gatgtgagac atctgttgaa   2460
gagggtgttt tcagtgacga ttcctggatc tcgagtccgt ccaaggcaga caacctcgca   2520
agtatctgtc ggaggtgcga gcccgtccaa tggtcaagtc gcggcgcaac atgatcctgc   2580
agatccgtac cccgaggcag acgattttga cgacgaagcg ctcgcggctt acatcctcct   2640
catctcccca cgccaaagtt ttgtatggtc cggagcggtc atgacgctgg atgtggatta   2700
catcgactat gaactacctg ataaccgagt cagattgatc gctgacggtc ccaccaagcg   2760
```

gttagcgctg tgcaaacttt atttcaagca agcgctcatt caccctgata cgggcgaaac 2820
aatcgacttg ccatgtgtgg ttgaggctca agcgcattta ccgaccattc agaaacaact 2880
tgtcaagatt gctaaatcga gttatcgtct ttcagagtgc attgtccagt ctgcaccact 2940
cgtccgcaat gcgttcaggg gcaaaccggg atcacaagag ttggtggaga attggtacag 3000
ttttgcgaca gagcatggga cgagagtgtt gatccatatt gagcctagtg tatgggagcg 3060
attcaatcgg ttgttgatgc gtctggcgat cagttggatt agctttatca gtcaagagtg 3120
taaccccaca gaccgcaaga cgttccgatg gactgtggca gctttgacct atgcgttcaa 3180
catgacgaga gggagtaaca ttctcgcgct tgatcgatca gaattttcgc ttttgaggag 3240
gtatgttggt gtttgtgtgt cactgttggt tagccacttt gatatcctcg gcgcaaggtc 3300
gagtatggag gccaaaaagg aggcagacag gattgaggcg atgaggaggt tacaacggct 3360
tcaagaaaac ctggacgacg aattcctgcc ccggactccg acagagtctg gcgatcaacc 3420
acgtatcgac cgctctataa ggctcacagt cgaagaacgt ctccgtctca ttgccgagct 3480
cgaagctcgt cgtgacgagt tggcacccgc acccgtcggt caagtccttg atgaagaagt 3540
ctctgaagac cgtgcgttgg tgttccttgc agcttccaaa tccaacattt ctatgcgatg 3600
gcagcaaggc gcgtacatcg gtggaggtgc atcgggaagc gtgtacttgg gatactcgtt 3660
gcaggataac actgtgtttg ctgtcaagat cttgccaacg gtggatctgc agagtagtcc 3720
ggcgttgtac gaaagtatca agcgagaatc ggatgtgatg agcttgttga gtcatccgaa 3780
tatcgttggt ttccttgggt tggaagtgca taggaacaga gtttgtcttt tccaagaggt 3840
aagtgcttgt tgttgtttcc atttgtgttg ggagggtgtg gtgccaaagc tgatgttcgt 3900
gattttagta ctgtgaagga gggtcgctgg caggtatgct cgaatatggc aaaattgacg 3960
atgaggaagt cgttggagcg tttacgatcc agctgttacg cggccttgag tatctgcaca 4020
ccaaccgcat cgaacaccga gatctcaaac cagaaagtaa gctgacaccc atcttttgat 4080
cctttccaac acacacacac taactcgtgt tctccacaga tattctcatc ggcgccaatt 4140
ctgtcctcaa gctggccgac tttggtaccg ccaaaatcat caaatccaac aagacgctcg 4200
cccgtacacg tggtggcgcg cacgccaaga tggagggtct tgagggtaca ccgatgtaca 4260
tggcgccaga gatgatcaag aaccagagga ctggcaagct gggtgcttgt gatatctggg 4320
gtttaggatg tatcgttttg cagatgatca ctggtaggaa gccatggagc ttcttggact 4380
ttgataatga atggtacgtc ttttcttgca atgatgtttt ccgcgtaggg agttatgagc 4440
tgataatatg attagggcaa tcatgttcca tcttggtgcg acaaaggagc cacctcctct 4500
acccgatccc aacgagatgt ccgaccaagg tatcgaattc attgatcaat gtctttcttt 4560
ggatccggaa gcgaggccgg tggccagcga gttattgcaa gatgaatggc tggttccaat 4620
gttggagcag atggtgagtt gtctttcatg tatgtgtaaa aaatggtcag aagcttatct 4680
gctttgcaaa acaggccgag ctggagcaag aataccccga tatattggcg atgggccaaa 4740
gtga 4744

<210> SEQ ID NO 11
<211> LENGTH: 2202
<212> TYPE: DNA
<213> ORGANISM: Cryptococcus neoformans
<220> FEATURE:
<221> NAME/KEY: gene
<222> LOCATION: (1)..(2202)
<223> OTHER INFORMATION: genomic DNA of PBS2 serotype A H99 strain -continued

<400> SEQUENCE: 11

```
atgacagacc ctacgccccc cgccctggac agtctctccc tggcagacaa ggcgcctact      60
cccgaagaaa gtcccgaaga cgccgctgaa cagcccaagc ccgcggcctc accgtccgca     120
ggcacacccg gccatgacgc ccaaagctca tccacctcgc ccccgcaacg ccctcagtcc     180
atgcagacaa atgacaaggc gccagataca tctgctccgg cttccaggcc ccaaccgcaa     240
catgtccctg catcggcacc tgcgcttccc tctaccaacc ccgtccgtcc acagccgggc     300
gcccgtcctg gagcggcgag gggtatgccc gcgcccatgg gtatgcgggc gcaagcaggc     360
cgaggcgctg gcggccccca gatgcagacc aagatgctgc ccagtttgca ggctaaaatg     420
gacaaggtgt gtatcgctcc atcatttatc ccgctgcata ctcatccaga ggctgtgctg     480
acaaaccaca ctatgctatc attagatcgc ggcgtctcgg caagggccac ctccctcctc     540
tggcatgcat gatccgaatg ccacatccat gggcgccctc ttacgctccc aagccctccg     600
cgcccccggc gcatcgcaag ctcctcccgg ccccggaccg gcttcaggcc ctttcggtct     660
cgccgctcgg cgcgcagctg ctgggggccc tccgagaccg aatttgggta tgatgggtat     720
gggtgcaagt gcgccgggtg cggttggacg gggatcaggt ctggcgggta gacgggggcc     780
ccctggagga ctgacactga gtgggatgaa gggtgcgatc aaggatgagg gaaacaagtt     840
ttcagacttt cagggtgtca tgtgggttca gcagactcct tttccatgac tgtgggctga     900
tctcaagtac agggacccgt ctggatcgct gagattctca aagaaggctg tcctgcatgc     960
aaagggcgtg gactttgagg atgggcaaag tttcaagatc aatatggatg agatcgaggt    1020
gcttggagaa ttaggaaagg gcaattacgg ttctgtgcac aaagtcttcc accgtccgac    1080
aggcgtcacc atggccatga aggtgatctt attctttctt gcgtcgcttc tggtccagta    1140
actaacaaac acgacaggaa atccggttag aacttgacga ttccaagctc aacggcatca    1200
ttatggaact cgacatccta caccgggccg ttgctcccga aatagtcgaa ttctacggtg    1260
cattcaccat tgaatcatgc gtctactact gtatggagta catggatgcc ggttcactcg    1320
actctctcac cggtggcggt gtggcggcca aagatcaaac aaaggatgaa gaaaacgatg    1380
cgacaaaacg agtgccggag gatgtattga ggaggattac agcgagaatc gtgaaagggt    1440
tgaggttctt gaaggatgaa ttgcagatca tccatcgagg tgagttttcc atgtgcaatg    1500
aaaacgggag gaaatgtgct gatatgatgt agacgtcaaa cccacaaatg tgttaatcaa    1560
tggcaaggga gaggtcaaga tgtgtgactt tggcgtttca ggtcagctcg aaaagagttt    1620
ggccaagacc aatatcggtt gtcaatccta catggctgta cgtctttccc tctcctccat    1680
ctcaaagagc ctcccagcta acccgattcc ctctctttct ttagcccgaa cgtatcaagt    1740
ctgaaactgc caaccagaat cctacatata ctgtctcttc agacgtctgg tctgtcggtc    1800
tgtccattgt cgagcttgcc aaggggtgtt accoctaccc accggagacg tatgcgaatg    1860
tgtttgcgca gttgcaggcg attgtgcatg gcactccgcc aacgttgcca cctgggtaca    1920
gcgataatgc gaatgatttc gttgccaagt ggtacgtctc tcacccottt ctcttcgtgt    1980
ttgaatttga caatgctgat aatgagcgca atctttagtc ttgagaaaga tcccaaccga    2040
cgaccgactt atgctcagct cttagaacat cctttcttgg tagcggacaa gggcgcagaa    2100
gttgacatgg ttggatgggt ggaaggggcg ttgaagcgca aggcagagag ggggattgcg    2160
agcctgaatc ctatccaacc acctgtccct ttggaaccat aa                       2202
```

<210> SEQ ID NO 12
<211> LENGTH: 1620

<212> TYPE: DNA
<213> ORGANISM: Cryptococcus neoformans
<220> FEATURE:
<221> NAME/KEY: gene
<222> LOCATION: (1)..(1620)
<223> OTHER INFORMATION: genomic DNA sequence of HOG1 serotype A H99 strain

<400> SEQUENCE: 12
atggccgatt ttgtcaagct ctccatcttt ggaaccgtat gtttctttta ttgctctttc 60
tcttttccca ccaccgtcat gatctgctct tccaaccaac caacctacga acacgcggcg 120
tttgtttttt ccgttggcca ctggatcata tcgtgttgat tctgtccata cgccggatgg 180
aggagatctg taaaggcaag gccgcggacg ctgatggatg ggctttctcc atggataggt 240
ttttgaggtt accacgcgtt atgtcgacct ccaacctgtc ggtatgggcg ctttcggtct 300
cgtctggtga gtcttgtttt tctcaagcaa ctatcctttc atctggtttt tcaacccagc 360
gtcgaaacag gtcgtccgac ctttgcatgt cgatgtagag atgtgaactg acaaaaccat 420
cttgtttgat gcagttccgc caaggatcag ctgtctggaa cttctgtggc tatcaagaag 480
attatgaagc ccttttcaac ccctgttctt tccaagagga cttaccgaga gctcaagctt 540
cttaagcact tgagacatga gaacattatc tctcttagtg acattttcat ctctcctctc 600
gaagatatgt gagttttgct caatagttgc atatcaaaga aggggggagg gggcctgctg 660
acatttatcc aatagctact ttgtcaccga gctgctcggt actgaccttc atcgactcct 720
tacctctcgc cctcttgaga agcaattcat ccaatacttc ctttatcaaa tcctccgtgg 780
tctcaagtat gtccactctg ccggtgtagt ccatcgagac ttgaagcctt caaacattct 840
cgtcaacgag aactgtgact tgaagatttg cgatttcggc cttgcgagga tccaagaccc 900
tcagatgact ggttatgttt ctacgaggta ctaccgagca cccgagatca tgttgacatg 960
gcaaaagtat gatgtcgcgg gtgagtttca agttttacgt ttgggggtgg tcttttaatt 1020
ggcgatccat gctgaccacg caaaaaatca gttgacattt ggagtaccgg ctgtatcttt 1080
gcggagatgc tggagggcaa gccattattc cccggaaagg accacgtgaa ccaattctca 1140
atcatcaccg aattgctcgg tactccgccg gacgatgtca ttcaaactat cgcctctgaa 1200
aacactctcc gtttcgtcca gagtctgccc aagcgcgaaa aggtcccatt ctccaccaag 1260
ttccccaacg ccgaccctgt gtctcttgat ttgttagaga agatgctcgt gtttgaccct 1320
cgtacccgta tatccgccgc tgaaggtctc gcgcacgagt atcttgcgcc ttaccatgat 1380
cctaccgatg agcctgttgc cgccgaggtg tttgattgga gttttaacga tgcggatttg 1440
ccggtggata cttggaaggt gatgatgtat agtgaaattc ttggtaagtc tctgtgcctt 1500 gcctttttttt gggtattata ctaacgtcgg actttagact tccacaacct cggagatatt 1560
tcacagaacg aagcagaggg acccgttact ggcgaagtcc ccgctgctcc tgccagctaa 1620

<210> SEQ ID NO 13
<211> LENGTH: 3792
<212> TYPE: DNA
<213> ORGANISM: Cryptococcus neoformans
<220> FEATURE:
<221> NAME/KEY: gene
<222> LOCATION: (1)..(3792)
<223> OTHER INFORMATION: Genomic DNA sequence of ENA1(CNAG_00531.2) serotype A H99 strain

<400> SEQUENCE: 13
atgtcttctg agaaaggaca atcaaataca aacgagaaac aacttattaa ccgcgccgac 60
actggcaaga ctgcagtgtc agactctcct ctccctttca aacctcatac cgctctctct 120
ggcaagatcc tcgaggcttt agggagtaat gttacttctg gtctatcaga tgacgaagca 180
tcaaggagac tccaacaata tggtcccaat aggctgaagc cccctgagag acctagtatt 240
ctcaagatca tcgctaggca agtgggcaat gctatgactc ttgtcctcag taggtgttct 300
ctccctttaa cgtttcttaa gctgatcaat ttcgtagtcg ctgccatggc aacttcattg 360
ggtaccatgg actggatcag cggtggcgtt attgcggctc tggttatcct caatgtatca 420
gtgggagcct acacagaatg gcaagccgaa aaggtacgtg ttttaagatc tgcggagatc 480
ccataaaccc cgaggaattc tgacgtcata aatagaccgt ggccagtctc gagtctgttg 540
gagctccgca agctactgta gtccgaactc gcaatggctc tcgcgaggct accgtcaaaa 600
ttatccccgt agaggaagtc gtacccggtg acattattca actcaaaaat ggtgatattg 660
ttcctgcgga cggaagaatc cttgacgggc acctgagtaa cttggaagct gacgaggctt 720
tcctgactgg cgaaagtctg ccggttgcaa aacagactga gcctatcgat gaagaggact 780
gtcctgttgg gtaagtagaa aagatttccg cacattcagc cacagcctaa ttatgaggac 840
agcgaccgtg tttgtatggt cttttctggt tcccagatca ccaaaggtcg agctcgtgcc 900
gtcattacca gcactggtat ggggacagag attggaaaaa ttgctcaagc tcttgaatct 960
aaagctaaaa ataagaaccg tggatttgct gctttctggt ggaaagtcaa agttattttg 1020
ggtgtcgagg agactactcc tttgcaaatc aagtatgtta tcttgctata gtagtgtaat 1080
ggttggatgg tactgacgcc gatgctagac ttaataagct cgcatacttc cttttggcgt 1140
gtgccctcgt catagccgtc attgttgtcg cctccaccgg ttttaatgat gtccccctct 1200
ctattgccac ctacgctgtc gctgccgccg tctccattct ccccgcctct ttgattgcag 1260
ttgttagttt gactttggcg cgtgcgtcaa ctgatttagc atctcgacat gctttggtcc 1320
gacgaatgga tgctattgag gctttagctg gtgttgagaa tgtgtgctcg gacaaggtaa 1380
gttaccattc aatttggctc gaaacctgtt gatacagttt tagccggtac ccttactgtt 1440
ggccgcatgg tagttcgcaa agtctgggtt cctgctcttg actggcgccc caatgaattt 1500
gctcccctcg acactagtgg tggtcaagca tatagttttg agaccggatc tgatcctttc 1560
tatcctcgtg gtgaagtcct ggccgattcc cagaagatca ctgggactgc ggagaccctc 1620
gatctcaagc aacctcgtga ccaatctgac tcttcctctt ccgactctga ccccgatgaa 1680
cgagacgtag aggaacaaga acgggtcatc cacgttgaag acatggaaaa caaccttcga 1740
gaccttgctc tctgtatttc gctttgtaat caagcgactc tcactcgtcc tgtcaaccaa 1800
gacggccaat gggaagcaaa cggtgatcct accgaaacgg cccttcaagt tgctgcacac 1860
aaacttggtc atggcaagcc ctttcttact catgctgcca agccaagcca ccgtgcggat 1920
tctatccgat ctggtcacag ttctcgtccc cttgttgctg gtattcgtgg gcactttgtt 1980
ccgataattg agcatccttt cgattccacc gtcaagcgaa tgtcaatcgc ttataaattt 2040
gtgagcgagg atcctcagga ttctcacatc ctctgtctcc ttaagggtgc catcgagcgt 2100
gtctttgaac gatgcaccaa gatccaagga cagcccatca ccgaagagca taagaagaat 2160
atcatggtca aagttgatgc tctcgccgct caaggtcttc gggtcctcgc tctttgtgga 2220
aagcgacttc ctgtcagcat ggtagacgaa gtcaaatcca cccctcgaga cgcattcgaa 2280
gccgatttcc atttcctcgg tcttgctggt atcttcgatc cgcccagaaa ggaatctgca 2340
ggcgccgttg ctgattgttt cagggctggt atcacccctc gaatgttgac aggcgatcat 2400
cctgctaccg ctacagctat cgccctcaac attggtattc tcgataagac gtactcaaag 2460

```
gattcagtca tgacgggtca gcagtttgac tctttgagcg aagacgaaat tgatcaactg   2520

cccgagttgc ctcttgtcgt tgctcgctgc gcccccgaaa ccaaagtgag ctgttttaac   2580

atatctaatg atgtacttgt gcctgacggt tcccagttcg aatggtcgat gccattcatc   2640

gacgaggaca aagcactgta atgactggtg atggtgtcaa cgactctccc gccctcaagc   2700

gtgctgatgt gggcgttggc atgggtactg gttccgatgt tgccaagcag tcagcgcgta   2760

tcgtcctcag tgatgacaac ttcagcacca tcattcgggc tattaggaaa ggtcgttctg   2820

tcttcaagaa cttgtctaaa ttcttgctcg tgagtaattc aatgcatgtg atggaaacga   2880

agctgatctg gcttccttag tacttgcttt ccggtaactt ggctgaaatc atcgtcctca   2940

tgattggtct cgctttcaag gatgacaatg gtcaggctgt tttccccctg tcacctgttg   3000

ccgctctttg gatgtacgtg taactacctg attctttgca aggactttga ctgactccca   3060

tttagcaaca ctctcgctgc cggacctcct gcccttgccc taggtcttga acctacagct   3120

atcgacgcca tggagcaggg acccgaggta taccatcgaa tcttcactct tgaattttac   3180

gtcgatctga tcttctacgg tttcctgatg ggctccatca gtttggtcaa cttcgtcatt   3240

gtactatggg gatactatcc tgtaagttca gtttgcatcc ccaagaagca tccctaattt   3300

atgaataggg agacttaggt cgtctttgta acgaagatga tcccagcatc tgtgatcccg   3360

tctatcaggc tcgagctgcc tgttttgcca ccctcgttat tgtcctcatg attcatgctt   3420

tggagtgtaa gcacttgagc aaagggttgg cccaaatcaa tttgcgtgac aacaaggtgt   3480

tgctgtggtg tgtcgttgcc ctcagtcttt ccactgtaag ccctttacac catctatctg   3540

gcctacgata tcagctaatg atgaacatag ttccctgtcg tgtacattcc tgtgatcaat   3600

aacaaggtgt ttttgctcaa cggtcccagg tgggaatggg gtatcatctt cggcatgatc   3660

ttggtgtatc tcagtgctac tgagctctac aagtggatca aaagaatttg gatccgacga   3720

catgcccccc cttccaaagg accttccgac aagaccctta ggatggagag taccattgct   3780

cctcctgttt ga                                                       3792
```

<210> SEQ ID NO 14
<211> LENGTH: 3173
<212> TYPE: DNA
<213> ORGANISM: Cryptococcus neoformans
<220> FEATURE:
<221> NAME/KEY: gene
<222> LOCATION: (1)..(3173)
<223> OTHER INFORMATION: Genomic DNA sequence of NHA1 (CNAG_01678.2) serotype A H99 strain

<400> SEQUENCE: 14

```
atgactgctt tccacccctt tgaagtcaat gcccctcatc tcgcatacac gttcctcggc     60

ggctttgtgg tcatctttgg catgatcagt ttgtttatca aagagaagct ctatgtcggc    120

gaagcaccta tagcaactgt agtcggcatc atcattggtc cccattgcct caattttttc    180

aatcctgcag gatggggtgg cggggaggaa gaggtcgcga gtgacgttac attggaattc    240

actcgcgttg tcattgctat atccgtattc gccgtcggcg ttgaattgcc caaggtaggt    300

ggtaacttgt gattcattgg agtagagaaa gcgctgatct tggtgcttgg gaaaggcata    360

catgaagcgg cactggcgat cgctcttctt ccttcttggc ccgtgcatgg tgtggggatg    420

gatgatctcc gccctgctga tctggggcct gatacctgac ctaacatttc tcgcctcgct    480

cgtagttgcg gcgggcgtca cccccacaga tcctatcttg gcccaggcag ttatcggagg    540

caagttcgcc gataaacatg ttcccgccca catccgccac ctcctctccg cagaaagtgg    600
```

```
aagtaacgat ggggccgcct ttcccttcct ctacatcgcc ctctacctcc tactcgatgc    660
gagcccaggc catgccgtcg gagaatggtt ctacatgact tggtgcgtag gcaaacctag    720
agcatcctca gttacctttg ttcttgtcgc tcacatgtct ttttagggtc tacgaaatta    780
ttcttggtgt tatcatcggg gccatcctgg gattctgcgc acgcaagttg atgaagttag    840
cggagcgcaa acgtctcatt gataggcagt cttacgtcgc ccagtatgtc agtctggcag    900
tgctgtcgat tggtaagcgt gttgaccggc cttgcgatta ttcaatgagc tgaccacgat    960
gtaggcgtta caagtttgct cggcagtgac gatttgcttt ctgctttcgc ttgcggttgt   1020
gcttttgcat gggagtacgt agtgcttgtg atttatctct tgactgcgct gacgacatta   1080
cagcggtttc ttcaacaaag ctacggagga tgcggtgttc tcgaacgtta ttgatctact   1140
tttcaattgc gccgccttca tctatatcgg cgctatcatt cctttcaatc attttaacga   1200
tttgcccgat gtacgttcgc atgggctacc acatacacga actaactgga tctcagctcc   1260
gagtatggcg attggttgtg ttggctatcc tcattcttct agttcgtcgt ctgccttcta   1320
taatagcgtg ttacaaattc gttcccgata tcaagacgtt cagagaagct ctttttacgg   1380
gatggttcgg tgagttcctt attgtgagta tcggttgggt catgtctgat gagaggttag   1440
ggcctatggg cgtcggtgct gtattcatct ccactcttgc tcggtcgtct ttgccagaag   1500
gggagcctga acagaataca gaagcggtgg accgcctaaa agacgtcatc atgcctgtca   1560
ccttatttct tgtattgtct tcaatcgtaa ctcgtaagtc tatcccgtcg cactcactac   1620
tgactcagtg tagacggcat gtcaattcca tttttctctc ttggtcgccg ggtccattcc   1680
attacttata ctcgatcacg aaatctttcc atggacacgc gaggcgatga gcctgcctgg   1740
acaactcatg ctcggcgtat tattccaggc caggagatca ttgtcaaccg tgatgacgac   1800
gacgaagaag gcgacttggg tgttagacgg atggacacac tcacgagcga ttcaaatggt   1860
cgtatcaggg aaaagattga ggaagaagat agcggagaaa gtagctcatc ccgaacaagg   1920
cagggagaaa tgattgaaat gacagaaaaa cgtggcccgg ctcgccatgg tagccaggcc   1980
agccagggcg aagcggcgga ggaaggagag aggtggagaa gttcgggaga agaaagctct   2040
gatcttgcga atgaccctga gacacagaga gaggtggaag agggaatgga agaggtcgaa   2100
gataaggaag gaggtggtag aagaacgccc cccctggcca agtacagaga aggaaaccac   2160
ctcattgtgg agagaaaagt caaggacagt gacgaggtat gctatgcgga tgtcccaatt   2220
gcttatcacg acttgctcat gcgtatggct tttaggttga agtcgaggtc atccgaaacc   2280
atttttccga caacaagaaa acggaaagtg accgcttcac tcatccccat cgcctcaagt   2340
cacgagagct tgacgatttg cttcatcacc ttcccaaaag cctcgagcat gctacttcac   2400
gggttcaaaa tggcggcaaa gatgcagttg atcgtctcgg tcttgggctg atggctatta   2460
acactccgga accgtcacca tcgatcgaat cgcacggcgg tccaaggcat gattatgtcg   2520
atggcttgga gagaacgcag agcccagagg gtcttgcaga cgaggatagg gatagcgagg   2580
gccggggcga tgtgtcccat gggggtgatt atgaagaaaa cgaggccgac tatgaggatg   2640
ttccgaacga gactcgtcgg caaaggagga agaaaatgaa accaccagca attgtcgtct   2700
ctcggcagaa cagcgccggg ctcccgagac gatccatccg ctccaggctg ttcggccgac   2760
gacaacattc ttccaactct ccctcccgtg ccgaagaagg cttagcccct cccaatccat   2820
ctcttcttgt tccatcctca tccccttcgc gtcctcaaaa cattgctgca gaacccgagt   2880
ccatactggc agaagattcg cgcggatcat cctcaccttc ccaatctcaa aatcttgcga   2940
```

tccctctcac aagaaccctt tcagctagcc gatcgtcgcc tgcggtgcgc ttcgccgacg 3000
atgctagtcc ttcatcggac acagcgcctg ggcagtcaaa ttatggtact aacgctccag 3060
gtttcaagaa gaatccggct ttagcaatgt atcgatcggc cagtgtacaa agtacagggt 3120
ccaacaagga tgggcctagc gtatctttca aagaacctga aatcaagcgt tga 3173

<210> SEQ ID NO 15
<211> LENGTH: 3930
<212> TYPE: DNA
<213> ORGANISM: Cryptococcus neoformans
<220> FEATURE:
<221> NAME/KEY: C_region
<222> LOCATION: (1)..(3930)
<223> OTHER INFORMATION: coding region sequence of SSK1 serotype A H99
strain

<400> SEQUENCE: 15
atgtggggct caaatgcttc catcgccgcc tcggagtcga ccgactccct ttcccccgcc 60
ccctcccagt ctgccgccgt agagttcccc ctgcccgtaa gctcccgccc gtctctcact 120
tccgccgctc acccctccca gatgtccgct tcctcctcct ccacctcctc ccagcctctc 180
tttgattggc gcattcccaa gcccacctca ccccgcacac gcatggaccc attcgacact 240
tttgatcctg tatcctcaag ctcagaggat gatccggtcc ctcaagagag ccgccgtgct 300
ggtcatcagc gctccgtaac agatcctctt ttacgagatg gccaacccct cgatatggag 360
ttcactactg ccgggccgcc tatacagagc tacgactttg aacaaccgcc cacgtttagc 420
agaacgttat cttcccctct tccagctaaa gtcggctcgc ttagacaccc tatgccattc 480
accattgacg atttaagctc tcgcaatgtg aattcaaccc atcgtccgca gccgactaca 540
cctctgcatt ccatatccgt tgagttagcc gattccttgc aatcggccat tcaaacatta 600
ctgcatctgt ccccacctca cctactcgat aacgcaaaag aacagtactc tggatgcacg 660
gtacagatac ctgctacctc gctttcggcc cttttgacct ctatgagagg cctcaacttc 720
ttgtcggcgc atgctgaaga actggtcgac atgagtgcac gtggagatcc acctgtactc 780
catcaagaag acttcgatgt aggagaactt ttgcaaaacg ttgcggatat gttgagtgga 840
gaagcagcag aaaaacggat tgatttcgtt ttgttccatg gcgacgtagc gatgaggcat 900
gtcagtgtgt atggagattc tgatggaatt agctatacct tgagtcatgt tattcgacaa 960
atactggcag tagccaatta cgatgatacc atagaactcg gccttcaagt cattcctcaa 1020
agtccatctt tagcttccgc cgtcggactt cctctaacct ctgccgatgt tagtggagga 1080
ggtggtgtca agtcagcgtc cacatctcgg tcaggctccc ccaataacag tctctctcga 1140
tctaattctg tccatgacgg gccccttctc tgtgtgttcg aaatagtaca taacatctat 1200
cagccaccac caagctcggc atccgccact cctaaagccg agctgaaccc tttcactcat 1260
cttgctgaag aaaccgaagc cttgaaacca agattggata cagcattttg caaaaaacctg 1320 cttcatcggc aaaatgctgt cctcaaagtt gatgtgcagc cttcatctcc tttaggatcc 1380
gggatgcccc gtagagctta cgcgttatca gtgctcctac caagaggtaa acccatcact 1440
gagcctgcaa tactttctaa agaggaacaa gaagttcgtc aaccattttc atcccacgta 1500
cttgcacgag aacccaccct caatgagctc tcggaatttg ctgaatcatt acgaggaaga 1560
aaggtgttta tccatgccaa tttgagtagt gttttcgcga gacacctcac gagctaccta 1620
gctgcatggg gaatggatat atcgcatcta ccgacagatg gcgatgaggc tgataaattg 1680
aaggatgtcg cggccaaaca tgactcggct tatactggat ctatgggtgt gtcaggcggc 1740

-continued

```
actacttcca gcgcagaaac gccctattca attaaaccga ccggcgtgac tgctgttcaa   1800
cctggacact ttgtcattat cgacgatgat gttgcggtct tgcgccgtga actcgtgcgc   1860
atccgttcag aattacttcc cattctcttt aaacctagac tgtcaaagcg tcccactatg   1920
acttctcgaa cccgttccac cccttcattg cgacaggtcc ccccaaggtc atcatcgggt   1980
tctgtactta tacactttac ctctcttgcc aattataacc gagttcgaga cgcgattgcg   2040
agctttgtgg gggcgccagg gttaaccaat ccggaaactt atgttcagcc ggaggtgata   2100
gtgataccca agcctgttgg accacgaaga tttttgactg ctctgcatac cgctgtgaaa   2160
cagcctatgg ttgacccatt tttctcccct atcgccacat ctcctagatc accaggcgga   2220
ggttactttg gtggtttgcg gactccgacg gagagagaat caggattctt tgattctgtt   2280
gcagaagaac cacatgaaga ggcggattcg cgaccagatt atgccacggt gcagaaagcc   2340
agatctcctt taggagaatt tccgccttct gcggcacaga tcgttcgtac caaccaaggc   2400
ttgcatcttt cgcttcccac tccaaatgaa attatgacaa cgcctgctcc agaatatttt   2460
tctgggtctt ccaagtctcc tagctctggt gcgtccggag tcgtgatgca gagccctgat   2520
ggtcgtcctt tcggaatgtt tttcgaaccg cccataaaaa atgagcgccg cggatctact   2580
cacaggacgc cttccgattc catcaggagg aaacaagcga accgccgtgc gtctacaagt   2640
gatgaaccct tttcttcacc ttctaccgcc ctacctcccc gtcgctcgtc cacaatttct   2700
acgactggca atgaggaaca ccgcagttca cctatcgcta acgtcacaga ccgtcctacc   2760
cattcaaggg taaattcaag aaggaagaac aatcttccgg cggcggagca acctattttg   2820
gctgtgggca gggcaaaagg cagggaaaga tcggagactg tcacgaaggg aggggacctc   2880
gggtcgagaa aaggtacacc agcggcaagc ccacgtatag aggagaagaa ggaattggaa   2940
agaggcgaga agactaaaag cctggctcct tcaactgctc ctacgaagaa gaatgctaaa   3000
gtcgatgttg tggtgccgcc catcaacgtg ctgattgttg aagacaaccc catcaatcaa   3060
aacattttga gtatgttcct gagaaaaaag aagataaaga attcctcggc caaggatggc   3120
gcagaagctg ttgaaaagtg gaggactgga ggcttccatc tgattctgat ggatatccaa   3180
ttgcccgtca tggatggcat agctgctacc aaagagattc gtcgacttga acgtcacaat   3240
aacattggcg tttttccatc gactccagcg gccgaacttc ctcggggtca aaatgttgcg   3300
gattctccac caccatcttc tccatttcgc tcgtcagtta tcattgttgc cctgacagcc   3360
tcgtccttgc aaagcgacag agtagctgct ttggctgctg gctgtaatga cttcttgacc   3420
aagcctgtgt ctttgaaatg gttggacaaa aagattgtgg aatggggttg tatgcaggca   3480
ttgattgatt ttgacggctg gcgacgatgg aagagctccg ataccaagaa tcctagcgaa   3540
actaagcagg gcttctcagt gggccctcaa caggctgcta ggtcgcttgc tagcagacta   3600
cgtattgaac gcaaaggatc tcgatctccg gcagctccag tatcaacccc gcgactcaat   3660
ttgcagtcgg caaccccaga taggccagaa accccccag attccacgtc acaaatgcca    3720
aaggccccgc ccgttgcagc ctctgacccc ccgttatctc ccaagtcgct gaacaagaca   3780
gttaatgatg tcttcgagca agcagacgct agactcgaaa atgcgcggga ggaacaagga   3840
gtatcaagtc aaaaggaaaa cacaagctta acagattcaa caaacaccac cattacgccc   3900
tcaaagacct atccggctcc tcccccatga                                    3930
```

<210> SEQ ID NO 16
<211> LENGTH: 5076
<212> TYPE: DNA
<213> ORGANISM: Cryptococcus neoformans
<220> FEATURE:
<221> NAME/KEY: C_region
<222> LOCATION: (1)..(5076)
<223> OTHER INFORMATION: coding region sequence of TCO2 serotype A H99
strain

<400> SEQUENCE: 16

```
atgatcttag gaaccgacat cgacctgtcg tctataccaa cggcgtttct cgaggcttat     60

cccttcccag cggttgtgtt cgtgatcgat tctcccccta gcccaagacc gcggctccat    120

tccagaaata cagacacgac cattcggcga acggatggcc aaatatcgcc tcttacaggt    180

cctccagtgc aacagttcgc gtcagcgccc gtggtatggg gcaatcaacg atggcacgag    240

ctggctcagg ggaaaacaat tgcagagtgc gtggatgtgg cgtcacagaa caagctgcaa    300

acttgggtgg aaaatgacac cggtgacaag tcggagagtt tggccctgga cctgaaggtg    360

ccgcaaggcg tgactcttca tctggcaaag accatattgc cattaagtcc accgtcctcc    420

tctcagtcac tttgcatcct tatatcgcaa tatatcgata agccggaaag tttcgcgcca    480

ccaatctcat ctggagatat tcttttctct tctctatcgc gactctccca gactttttct    540

cggtcatcct ctttttcatc caaccctaga aaatcgattg atgtccctgc gtcactatcc    600

gaacaccggg gttctgctac atcgacaagt agcaatctgc gctcttcgat cgatttgact    660

tcccctaatt ctcaaccctc tccactaaac cgtgaacaaa gcacgtactt cacccatggc    720

tccgcgacca gagaagagcg accctcagta aggcgtagac ggtcaccgcc aatctcaatg    780

acgaggccca agcctcttga gagccatgct caagaatgct gggacttggt agagaatttc    840

gactggtcaa aaacagcatt agggccgaga gaacagtgga tggatgcgtt agatcctgtt    900

ctggcaatca catttgaatc cagaacggca gattgtgcct ggttagggcc tgatctagag    960

ctagtttaca ataaggcgta tcaagagctg gttgaccatc ccaatgcttt tggaaaacct   1020

gcaagacaag tttgggctac caattgggac tacttggaac ccctggtcaa gcgatgtctc   1080

agtgggaccc cggtctacaa ggacaacgac ccgcttttct ggcgtcgata cggcaatggt   1140

cgacttctgg aacattacca cacttggcga tatgtcccga taacgggcaa agatggctca   1200

gtgcttggca tcttcaacca gtcaattgag gtcaccgact cagtactgct agagaggcga   1260

atgggcacga ccagggaact ttcggaacac atgtcgttta ttcgtacaac tgaggacttt   1320

tttagctcgg ttgccgacgt ctttagtcag aaccctactg acataccgtt cgcactttgt   1380

taccgggtcc gacaagttga caccgatggg acatttgtcc atttggacgt ctcgcttcag   1440

tcgtccgtcg gtgtacccga aggccatccg tctgctccag atcaaattcc cgtcagcttc   1500

ttaaatggta acccttaccc tagcaatgtc gagcgatcat ttctcctgc tttctcaatc   1560

gtttcaatcc actcttcgag cagtcatcga gtctgtcacg tctctgaaga cactacacaa   1620

tggcccatcg ccaaagccct acaaaggcgg caatgtgtca tcatcgaaga atgttcgcaa   1680

ttaatagaag gatatcctat ccgtcgctgg gatgggcttc cattctcagc cattgtcgtg   1740

cccatatgct ctgaagggtc tcccgaaatc cctgacgccg ttgttattct tggtctcaat   1800

gtgcgacgtt gttttgacca tgaatacgat tcctggattc actctattcg gtcacaacta   1860

tcttcggccc tcgtgatggt caaggcgcgt gaagctgaac aaaagatggt tgaggaaagc   1920

gcacgtatgg agaaagcaaa agtcgcttgg ttcagaggag ccgcgcacga ccttcgtagt   1980

ccattaaccc tcgtcgctgg accgcttgcc gatgtgcttg attcggattt gaactcgagt   2040

cagcgcacgg ctttgaccgt tgcgcaacgc aatcttgatc gtttagtgcg cttggtcaac   2100

gccctcatgg atttctcgag ggtggaagct ggacgaatgg aaggacgatt tgttccgacg   2160
```

```
aacttgagtc aattcgtgac acagttggca gctcttttca agcctgcaat agaaagattg   2220
gggttagaat acgtactaga tgtccagcca agcgaggagc ttgttttcat cgatcctgtt   2280
ctgtttgaga ccgtggtatc aaaccttatt ggcaatgcgc tcaaatacac tgaaacgggt   2340
tctatcactg ttcgggtgca atacacggat tacgcagagg tctcggtcat cgataccggt   2400
gtgggtatac cgaaaaatga gctggcactg gtgaccgaat ggttccacag ggcaagtact   2460
gccattcact cgggaaccca gggaacagga ttgggactgg ctttggccaa ggaattgctc   2520
aagttgcata aaggagaatt gcttgtcgag tctcaaaccg ccaatgagtc aggaggtcct   2580
catgggtcca tttttacagc gaaaattcct cttgatttca agccctctcc atcggctcat   2640
atcattccgt ccgtcgaatc tcacaagacg tttggcaaat acagtaaagc cgtcgcagac   2700
gaagccatgc gctgggttgg ggactcagat gccgctagtg aggcgtacga catgtcgagc   2760
ggtaccggag tctcaagcgc tggtagtggc tctggaaaca cgaccacctt cggacccaag   2820
tttgcagatg cctttttgtt tgataagaac gacattgtgc ttattgtgga agacaatgtc   2880
gacatgcgtg aatacatacg acagcttttc gccccttatt gtaccgtact cgaagcttcc   2940
aatggtgaac aggcttacaa tatggctacc caaaaccctc ccaacctcat tttgtcggac   3000
gtgctcatgc ccaaattatc tggtatggag ctactacaaa ggatcagatc ccatcctgac   3060
actcgcattg tgcctatggt ccttatttcg gctattgctg gtgatgagtc tagggttgag   3120
gctctgctaa acggcgctga tgactatctt gccaagcctt tcaaacccaa ggaactcatc   3180
gcgcgtgttc acctgcacat gcaagttggc aagaaacgtg ccaagctcga agcgctatac   3240
gcccaacgcg aaacagaatt gacagctcta tctgactatt gtccgatcgg tatcttccga   3300
ggagacaaat atggccatat tgtttatgcg aacgcagctt ggcgtgcgca gagcggcctt   3360
ttggtgggtg accctaacga ttgggcatct tatgtgcacc cggattcgaa agcgcagctc   3420
ttggaacaat ggaatcagtg gttgaggggg gatttgaagg agttccgagc ggcttggaga   3480
tggtctaatg gcatccctgt caggagcatc ttggtccggt tagatgacgt caaggaaggg   3540
ttttctgggt taattgggtg cgtagtggat gtgtctcatg aagagagacg attaatcgaa   3600
gctgaggaaa gaagaaaaga ggcggaagag agtaaacatc agcaagaact ccttattgac   3660
ttgacaagtc atgaaattag gaccccggtg tcagcaatcc tgcagtgctc agatcttgtt   3720
aaagagaatc ttgtagctct gaaggaccag ttgagaggag cggggccaaa gggctttgtg   3780
ccgagtcaag aattactggc tgatcttgag caggatgtgg aagctttgga aagtatttat   3840
cagtgcggtc ttgtgcagga acgcattgcc ggagatgttc tttcgctggc tcgtatccaa   3900
ctcgatatgc tgagtttgca cgacattgac gtcaacttgc gccgagaagg caggaaagtt   3960
tcgtccatct ttgcatcgga agccaagatg aaggatatcg acctccaatt ggaatttgga   4020
cctactatcg aacagtccaa agtgctggcc atcaagacag atcccgtgag attaggccag   4080
gtggtaacaa atctcatttc caacgccatt cggtttacat cttcgagtga tgtccgaaag   4140
attactatcc aatacgacgt atcgtttgtc cctcctgccg atgactcttg cgccctccct   4200
tcatctgttg gcttgcccga catacttcct gtgaaagaga atactccact atggctgttt   4260
gtcagtgtta ccgattctgg acctggtatg acagagcaag agttatctgt tttgttccaa   4320
aggtttgccc agggcaataa gatgattcat actaagtatg gcggaagcgg tttgggactg   4380
ttcatctgtc gaaagattac agagcttctt ggcggtcgta tcgaagtgct cagccaagtc   4440
gggcacggta gtgttttccg attcttcatt aaaacgcgcg ctgtcgctcc tccgtccgcc   4500
```

-continued

```
atcgctgctc tcgtagaatc ctctcctctc aaaccggtat ccgccacttc accttcttcc   4560

tcgttagcca tgagccgatc gtcttctcgg agcacaaacg tcactacacc tatagagggt   4620

ggtgggaccg agcacgtgtt gatcgtggaa gataacctaa tcaatcagac tgtcctgaag   4680

cgacagctcg tcaaggcggg tttatcgtgc aacgtcgcga gtaatggcct tgaagctctt   4740

aatgtcatcc gtgaagtcca tcggcaacac cgacgcggtg ggccgaaccg taaaaggcta   4800

tttgacgtgg tattgatgga tctcgagatg ccagtgatgg atggtatcac cgccgtacga   4860

gagatacgac agtccgaggc cgcggggaca ttgggcagga atatggtgat tgccctgacg   4920

gggaacgcga gacaaggaca gattgatcat gccttggctt ctggatttga cgatgtcgtc   4980

atcaaaccgt atatcctggt agatttgctg aacaagatca aatctatgaa agttagaaaa   5040

ttggagttgg aaactgcgaa agctcaagaa gagtga                             5076
```

<210> SEQ ID NO 17
<211> LENGTH: 4254
<212> TYPE: DNA
<213> ORGANISM: Cryptococcus neoformans
<220> FEATURE:
<221> NAME/KEY: C_region
<222> LOCATION: (1)..(4254)
<223> OTHER INFORMATION: coding region sequence of SSK2 serotype A H99
strain

<400> SEQUENCE: 17

```
atgtccaacc caacctcccc ctcaaacccc tcagacaccg gcccgtcctc ggcgtccaac     60

gtcacatcct cgtcctcaaa gaccggacgc agatcagtgc gcctctttgc cccagacgag    120

gaggacagct cagacgagga cggcggcctc atcggcgtgc ccgcagagac cacattcaag    180

gacgacgaga tccctccttc caacccacgt tccgcctcct accccgggcc accggcacac    240

acctccccca cctctaaaat ctcaaccatc gtttcgtccg cttctgcagc ccagccaaaa    300

cttgcacgtt caataacata cgtcgcaccc aatgccgtct cctcccggcc ggcatatccc    360

ctcaatcccg cagggtcaga aaccttacac gcctcaggaa ggtcgtatac tgaccccgat    420

ataggatact ttagccacga tgcaggagat gatggttggg gctcagatga tgacgacgaa    480

ttgagatccc ctggctgggg catatcccat cataacatgg actctggagg caagacgaac    540

gggtcaccac agttgcctat aaagcccgcc gatgtcaccg aggatgaagg acaggaacgt    600

ttagattggc aaggcatgct ggaaagtgtc ctcaactcgg atgttctcaa ggtggaggaa    660

caacgtatct acaattccat gccgacagat tcattcagag aagagattgg aaagaccctt    720

tggtggcaaa tccgtgccaa actgcgtggg aggacagagg cggaggagaa gaaacgggtg    780

caagagcgac gagcgagagt ggtggacccg gtgctggaag agataaacga gttcaagtac    840

gacccaaaaa ataacccaga aggcgaagaa gacagtgatg gcgatccgca agacgcgact    900

tcgactgctg caccccaatc caaagctctc aatcaagtca acaccgttct cgccaaactt    960

catgcaatca aaggtcttta tcccaacctc gcagccatgc gagccgacaa ggttctctat   1020

accgatgaaa atttccgcaa acgcgccgac gcattgacct cttggtccat catcgtttca   1080

tccctccaaa cccagctcaa actcttgcaa aaatggacag gttccgatga gcttgacatc   1140

accaagccca acacgaccca cgagaaagca ttggtcggca agtacaagta tcactctatc   1200

gacagcaagg gtacgcccgg cagggatgca gccgatgact cgagtttcct cgatcgtgtg   1260

ataaaagaag ataaccttca acggacattc gagcgtcgag cgtttgtaga catgatcaac   1320

ctcgtgcgca acgccaagga gacggtcatc agctatctcc cccagttcca agaacaaaat   1380
```

-continued

```
cttcccgatt tccagtacga aatcgttcgt cttattggtt tccccggtcg acttatcatt   1440
gaagctgtca aggttcgttt ggatgctgca tcccgactac ttgacccgaa ccctatggtc   1500
gtcgaagact ttatcgaaaa ccttcgtcta tccatttcgc tcgccgtgct aatccggaaa   1560
caatacgacg aaatcatggc acccgatgcc gaggggagat ggaaaatccc gcattgcttg   1620
ccgacagagt acaatgatgt tctgctcgat gcgctgagga cattttttcaa attgttgcat   1680
tggagattac gaggagtggg gaaagcgagt tattacaagg aaacagaagt gttggaagaa   1740
gaggcgccgt tcttgtatga agcggcggag gctattgtag gcggtgatat ggttgttgca   1800
gagcagtatt gcgcgttatc caacaagctc cttatacgtt cagcaaatta tcttgaccag   1860
caacttcggg taccaataca ttccccgtct cgcgacaagg aacgtggtga caaggagcgc   1920
gatggctctt cgtcttctca acgtaaccgt gacggccgtg atagctcgct gcccggccca   1980
ccgaaacaca tgaaagtcga agaactcttc tcatggtact ccaaactcct tgattccgct   2040
cgtatgcgac accgtaaaac ccaacgtttc tgtcgtaaac tcacccaacg attcgataat   2100
tccgccgaat attcaatcga ggagacggag atggacatgc tggtggagac attgcaagat   2160
actggtcatt tcttggtata taccgggaaa tttgaggcga atgggacgta tatcgttgcg   2220
gatgggagtc tctggggtca gccggacgat gtgagacatc tgttgaagag ggtgttttca   2280
gtgacgattc ctggatctcg agtccgtcca aggcagacaa cctcgcaagt atctgtcgga   2340
ggtgcgagcc cgtccaatgg tcaagtcgcg gcgcaacatg atcctgcaga tccgtacccc   2400
gaggcagacg attttgacga cgaagcgctc gcggcttaca tcctcctcat ctccccacgc   2460
caaagttttg tatggtccgg agcggtcatg acgctggatg tggattacat cgactatgaa   2520
ctacctgata accgagtcag attgatcgct gacggtccca ccaagcggtt agcgctgtgc   2580
aaactttatt tcaagcaagc gctcattcac cctgatacgg gcgaaacaat cgacttgcca   2640
tgtgtggttg aggctcaagc gcatttaccg accattcaga aacaacttgt caagattgct   2700
aaatcgagtt atcgtctttc agagtgcatt gtccagtctg caccactcgt ccgcaatgcg   2760
ttcaggggca aaccgggatc acaagagttg gtggagaatt ggtacagttt tgcgacagag   2820
catgggacga gagtgttgat ccatattgag cctagtgtat gggagcgatt caatcggttg   2880
ttgatgcgtc tggcgatcag ttggattagc tttatcagtc aagagtgtaa ccccacagac   2940
cgcaagacgt tccgatggac tgtggcagct ttgacctatg cgttcaacat gacgagaggg   3000
agtaacattc tcgcgcttga tcgatcagaa ttttcgcttt tgaggaggtc gagtatggag   3060
gccaaaaagg aggcagacag gattgaggcg atgaggaggt tacaacggct tcaagaaaac   3120
ctggacgacg aattcctgcc ccggactccg acagagtctg gcgatcaacc acgtatcgac   3180
cgctctataa ggctcacagt cgaagaacgt ctccgtctca ttgccgagct cgaagctcgt   3240
cgtgacgagt tggcacccgc acccgtcggt caagtccttg atgaagaagt ctctgaagac   3300
cgtgcgttgg tgttccttgc agcttccaaa tccaacattt ctatgcgatg gcagcaaggc   3360
gcgtacatcg gtggaggtgc atcgggaagc gtgtacttgg gatactcgtt gcaggataac   3420
actgtgtttg ctgtcaagat cttgccaacg gtggatctgc agagtagtcc ggcgttgtac   3480
gaaagtatca agcgagaatc ggatgtgatg agcttgttga gtcatccgaa tatcgttggt   3540
ttccttgggt tggaagtgca taggaacaga gtttgtcttt tccaagagta ctgtgaagga   3600
gggtcgctgg caggtatgct cgaatatggc aaaattgacg atgaggaagt cgttggagcg   3660
tttacgatcc agctgttacg cggccttgag tatctgcaca ccaaccgcat cgaacaccga   3720
gatctcaaac cagaaaatat tctcatcggc gccaattctg tcctcaagct ggccgacttt   3780
```

ggtaccgcca aaatcatcaa atccaacaag acgctcgccc gtacacgtgg tggcgcgcac 3840
gccaagatgg agggtcttga gggtacaccg atgtacatgg cgccagagat gatcaagaac 3900
cagaggactg gcaagctggg tgcttgtgat atctggggtt taggatgtat cgttttgcag 3960
atgatcactg gtaggaagcc atggagcttc ttggactttg ataatgaatg ggcaatcatg 4020
ttccatcttg gtgcgacaaa ggagccacct cctctacccg atcccaacga gatgtccgac 4080
caaggtatcg aattcattga tcaatgtctt tctttggatc cggaagcgag gccggtggcc 4140
agcgagttat tgcaagatga atggctggtt ccaatgttgg agcagatggt gagttgtctt 4200
tcatgccgag ctggagcaag aataccccga tatattggcg atgggccaaa gtga 4254

<210> SEQ ID NO 18
<211> LENGTH: 1830
<212> TYPE: DNA
<213> ORGANISM: Cryptococcus neoformans
<220> FEATURE:
<221> NAME/KEY: C_region
<222> LOCATION: (1)..(1830)
<223> OTHER INFORMATION: coding region sequence of PBS2 serotype A H99 strain

<400> SEQUENCE: 18
atgacagacc ctacgccccc cgccctggac agtctctccc tggcagacaa ggcgcctact 60
cccgaagaaa gtcccgaaga cgccgctgaa cagcccaagc ccgcggcctc accgtccgca 120
ggcacacccg gccatgacgc ccaaagctca tccacctcgc ccccgcaacg ccctcagtcc 180
atgcagacaa atgacaaggc gccagataca tctgctccgg cttccaggcc ccaaccgcaa 240
catgtccctg catcggcacc tgcgcttccc tctaccaacc ccgtccgtcc acagccgggc 300
gcccgtcctg gagcggcgag gggtatgccc gcgcccatgg gtatgcgggc gcaagcaggc 360
cgaggcgctg gcggccccca gatgcagacc aagatgctgc ccagtttgca ggctaaaatg 420
gacaagatcg cggcgtctcg gcaagggcca cctccctcct ctggcatgca tgatccgaat 480
gccacatcca tgggcgccct cttacgctcc caagccctcc gcgcccccgg cgcatcgcaa 540
gctcctcccg gccccggacc ggcttcaggc cctttcggtc tcgccgctcg gcgcgcagct 600
gctgggggcc ctccgagacc gaatttgggt atgatgggta tgggtgcaag tgcgccgggt 660
gcggttggac ggggatcagg tctggcgggt agacgggggc cccctggagg actgacactg 720
agtgggatga agggtgcgat caaggatgag ggaaacaagt tttcagactt tcagggtgtc 780
atggacccgt ctggatcgct gagattctca aagaaggctg tcctgcatgc aaagggcgtg 840
gactttgagg atgggcaaag tttcaagatc aatatggatg agatcgaggt gcttggagaa 900
ttaggaaagg gcaattacgg ttctgtgcac aaagtcttcc accgtccgac aggcgtcacc 960
atggccatga aggaaatccg gttagaactt gacgattcca agctcaacgg catcattatg 1020
gaactcgaca tcctacaccg ggccgttgct cccgaaatag tcgaattcta cggtgcattc 1080
accattgaat catgcgtcta ctactgtatg gagtacatgg atgccggttc actcgactct 1140
ctcaccggtg gcggtgtggc ggccaaagat caaacaaagg atgaagaaaa cgatgcgaca 1200
aaacgagtgc cggaggatgt attgaggagg attacagcga gaatcgtgaa agggttgagg 1260
ttcttgaagg atgaattgca gatcatccat cgagacgtca aacccacaaa tgtgttaatc 1320
aatggcaagg gagaggtcaa gatgtgtgac tttggcgttt caggtcagct cgaaaagagt 1380
ttggccaaga ccaatatcgg ttgtcaatcc tacatggctc ccgaacgtat caagtctgaa 1440
actgccaacc agaatcctac atatactgtc tcttcagacg tctggtctgt cggtctgtcc 1500

-continued attgtcgagc ttgccaaggg gtgttacccc tacccaccgg agacgtatgc gaatgtgttt 1560
gcgcagttgc aggcgattgt gcatggcact ccgccaacgt tgccacctgg gtacagcgat 1620
aatgcgaatg atttcgttgc caagtgtctt gagaaagatc ccaaccgacg accgacttat 1680
gctcagctct tagaacatcc tttcttggta gcggacaagg gcgcagaagt tgacatggtt 1740
ggatgggtgg aaggggcgtt gaagcgcaag gcagagaggg ggattgcgag cctgaatcct 1800
atccaaccac ctgtcccttt ggaaccataa 1830

<210> SEQ ID NO 19
<211> LENGTH: 1098
<212> TYPE: DNA
<213> ORGANISM: Cryptococcus neoformans
<220> FEATURE:
<221> NAME/KEY: C_region
<222> LOCATION: (1)..(1098)
<223> OTHER INFORMATION: coding region sequence of HOG1 serotype A H99
strain

<400> SEQUENCE: 19
atggccgatt ttgtcaagct ctccatcttt ggaaccgttt ttgaggttac cacgcgttat 60
gtcgacctcc aacctgtcgg tatgggcgct ttcggtctcg tctgttccgc caaggatcag 120
ctgtctggaa cttctgtggc tatcaagaag attatgaagc ccttttcaac ccctgttctt 180
tccaagagga cttaccgaga gctcaagctt cttaagcact tgagacatga gaacattatc 240
tctcttagtg acattttcat ctctcctctc gaagatatct actttgtcac cgagctgctc 300
ggtactgacc ttcatcgact ccttacctct cgccctcttg agaagcaatt catccaatac 360
ttcctttatc aaatcctccg tggtctcaag tatgtccact ctgccggtgt agtccatcga 420
gacttgaagc cttcaaacat tctcgtcaac gagaactgtg acttgaagat ttgcgatttc 480
ggccttgcga ggatccaaga ccctcagatg actggttatg tttctacgag gtactaccga 540
gcacccgaga tcatgttgac atggcaaaag tatgatgtcg cggttgacat ttggagtacc 600
ggctgtatct ttgcggagat gctggagggc aagccattat tccccggaaa ggaccacgtg 660
aaccaattct caatcatcac cgaattgctc ggtactccgc cggacgatgt cattcaaact 720
atcgcctctg aaaacactct ccgtttcgtc cagagtctgc ccaagcgcga aaaggtccca 780
ttctccacca agttccccaa cgccgaccct gtgtctcttg atttgttaga gaagatgctc 840
gtgtttgacc ctcgtacccg tatatccgcc gctgaaggtc tcgcgcacga gtatcttgcg 900
ccttaccatg atcctaccga tgagcctgtt gccgccgagg tgtttgattg gagttttaac 960
gatgcggatt tgccggtgga tacttggaag gtgatgatgt atagtgaaat tcttgacttc 1020
cacaacctcg gagatatttc acagaacgaa gcagagggac ccgttactgg cgaagtcccc 1080
gctgctcctg ccagctaa 1098

<210> SEQ ID NO 20
<211> LENGTH: 3273
<212> TYPE: DNA
<213> ORGANISM: Cryptococcus neoformans
<220> FEATURE:
<221> NAME/KEY: C_region
<222> LOCATION: (1)..(3273)
<223> OTHER INFORMATION: coding region sequence of ENA1(CNAG_00531.2)
serotype A H99 strain

<400> SEQUENCE: 20
atgtcttctg agaaaggaca atcaaataca aacgagaaac aacttattaa ccgcgccgac 60

-continued

```
actggcaaga ctgcagtgtc agactctcct ctccctttca aacctcatac cgctctctct    120
ggcaagatcc tcgaggcttt agggagtaat gttacttctg gtctatcaga tgacgaagca    180
tcaaggagac tccaacaata tggtcccaat aggctgaagc cccctgagag acctagtatt    240
ctcaagatca tcgctaggca agtgggcaat gctatgactc ttgtcctcat cgctgccatg    300
gcaacttcat tgggtaccat ggactggatc agcggtggcg ttattgcggc tctggttatc    360
ctcaatgtat cagtgggagc ctacacagaa tggcaagccg aaaagaccgt ggccagtctc    420
gagtctgttg gagctccgca agctactgta gtccgaactc gcaatggctc tcgcgaggct    480
accgtcaaaa ttatccccgt agaggaagtc gtacccggtg acattattca actcaaaaat    540
ggtgatattg ttcctgcgga cggaagaatc cttgacgggc acctgagtaa cttggaagct    600
gacgaggctt tcctgactgg cgaaagtctg ccggttgcaa aacagactga gcctatcgat    660
gaagaggact gtcctgttgg cgaccgtgtt tgtatggtct tttctggttc ccagatcacc    720
aaaggtcgag ctcgtgccgt cattaccagc actggtatgg ggacagagat tggaaaaatt    780
gctcaagctc ttgaatctaa agctaaaaat aagaaccgtg gatttgctgc tttctggtgg    840
aaagtcaaag ttattttggg tgtcgaggag actactcctt tgcaaatcaa acttaataag    900
ctcgcatact tccttttggc gtgtgccctc gtcatagccg tcattgttgt cgcctccacc    960
ggttttaatg atgtccccct ctctattgcc acctacgctg tcgctgccgc cgtctccatt   1020
ctccccgcct ctttgattgc agttgttagt ttgactttgg cgcgtgcgtc aactgattta   1080
gcatctcgac atgctttggt ccgacgaatg gatgctattg aggctttagc tggtgttgag   1140
aatgtgtgct cggacaagac cggtaccctt actgttggcc gcatggtagt tcgcaaagtc   1200
tgggttcctg ctcttgactg gcgcccccaat gaatttgctc ccctcgacac tagtggtggt   1260
caagcatata gttttgagac cggatctgat cctttctatc ctcgtggtga agtcctggcc   1320
gattcccaga agatcactgg gactgcggag accctcgatc tcaagcaacc tcgtgaccaa   1380
tctgactctt cctcttccga ctctgacccc gatgaacgag acgtagagga acaagaacgg   1440
gtcatccacg ttgaagacat ggaaaacaac cttcgagacc ttgctctctg tatttcgctt   1500
tgtaatcaag cgactctcac tcgtcctgtc aaccaagacg gccaatggga agcaaacggt   1560
gatcctaccg aaacggccct tcaagttgct gcacacaaac ttggtcatgg caagcccttt   1620
cttactcatg ctgccaagcc aagccaccgt gcggattcta tccgatctgg tcacagttct   1680
cgtccccttg ttgctggtat tcgtgggcac tttgttccga taattgagca tcctttcgat   1740
tccaccgtca agcgaatgtc aatcgcttat aaatttgtga gcgaggatcc tcaggattct   1800
cacatcctct gtctccttaa gggtgccatc gagcgtgtct ttgaacgatg caccaagatc   1860
caaggacagc ccatcaccga agagcataag aagaatatca tggtcaaagt tgatgctctc   1920
gccgctcaag gtcttcgggt cctcgctctt tgtggaaagc gacttcctgt cagcatggta   1980
gacgaagtca aatccacccc tcgagacgca ttcgaagccg atttccattt cctcggtctt   2040
gctggtatct tcgatccgcc cagaaaggaa tctgcaggcg ccgttgctga ttgtttcagg   2100
gctggtatca cccctcgaat gttgacaggc gatcatcctg ctaccgctac agctatcgcc   2160
ctcaacattg gtattctcga taagacgtac tcaaaggatt cagtcatgac gggtcagcag   2220
tttgactctt tgagcgaaga cgaaattgat caactgcccg agttgcctct tgtcgttgct   2280
cgctgcgccc ccgaaaccaa agttcgaatg gtcgatgcca ttcatcgacg aggacaaagc   2340
actgtaatga ctggtgatgg tgtcaacgac tctcccgccc tcaagcgtgc tgatgtgggc   2400
gttggcatgg gtactggttc cgatgttgcc aagcagtcag cgcgtatcgt cctcagtgat   2460
```

-continued

```
gacaacttca gcaccatcat tcgggctatt aggaaaggtc gttctgtctt caagaacttg   2520

tctaaattct tgctctactt gctttccggt aacttggctg aaatcatcgt cctcatgatt   2580

ggtctcgctt tcaaggatga caatggtcag gctgttttcc ccctgtcacc tgttgccgct   2640

ctttggatca acactctcgc tgccggacct cctgcccttg ccctaggtct tgaacctaca   2700

gctatcgacg ccatggagca gggacccgag gtataccatc gaatcttcac tcttgaattt   2760

tacgtcgatc tgatcttcta cggtttcctg atgggctcca tcagtttggt caacttcgtc   2820

attgtactat ggggatacta tcctggagac ttaggtcgtc tttgtaacga agatgatccc   2880

agcatctgtg atcccgtcta tcaggctcga gctgcctgtt ttgccaccct cgttattgtc   2940

ctcatgattc atgctttgga gtgtaagcac ttgagcaaag ggttggccca aatcaatttg   3000

cgtgacaaca aggtgttgct gtggtgtgtc gttgccctca gtctttccac tttccctgtc   3060

gtgtacattc ctgtgatcaa taacaaggtg tttttgctca acggtcccag gtgggaatgg   3120

ggtatcatct tcggcatgat cttggtgtat ctcagtgcta ctgagctcta caagtggatc   3180

aaaagaattt ggatccgacg acatgccccc ccttccaaag gaccttccga caagaccctt   3240

aggatggaga gtaccattgc tcctcctgtt tga                                3273
```

<210> SEQ ID NO 21
<211> LENGTH: 2751
<212> TYPE: DNA
<213> ORGANISM: Cryptococcus neoformans
<220> FEATURE:
<221> NAME/KEY: C_region
<222> LOCATION: (1)..(2751)
<223> OTHER INFORMATION: coding region sequence of NHA1 (CNAG_01678.2)
serotype A H99 strain

<400> SEQUENCE: 21

```
atgactgctt tccacccctt tgaagtcaat gcccctcatc tcgcatacac gttcctcggc     60

ggctttgtgg tcatctttgg catgatcagt ttgtttatca aagagaagct ctatgtcggc    120

gaagcaccta tagcaactgt agtcggcatc atcattggtc cccattgcct caatttttttc   180

aatcctgcag gatggggtgg cggggaggaa gaggtcgcga gtgacgttac attggaattc    240

actcgcgttg tcattgctat atccgtattc gccgtcggcg ttgaattgcc caaggcatac    300

atgaagcggc actggcgatc gctcttcttc cttcttggcc cgtgcatggt gtggggatgg    360

atgatctccg ccctgctgat ctggggcctg atacctgacc taacatttct cgcctcgctc    420

gtagttgcgg cgggcgtcac ccccacagat cctatcttgg cccaggcagt tatcggaggc    480

aagttcgccg ataaacatgt tcccgcccac atccgccacc tcctctccgc agaaagtgga    540

agtaacgatg ggccgccttt tcccttcctc tacatcgccc tctacctcct actcgatgcg    600

agcccaggcc atgccgtcgg agaatggttc tacatgactt gggtctacga aattattctt    660

ggtgttatca tcggggccat cctgggattc tgcgcacgca agttgatgaa gttagcggag    720

cgcaaacgtc tcattgatag gcagtcttac gtcgcccagt atgtcagtct ggcagtgctg    780

tcgattggcg ttacaagttt gctcggcagt gacgatttgc tttctgcttt cgcttgcggt    840

tgtgcttttg catgggacgg tttcttcaac aaagctacgg aggatgcggt gttctcgaac    900

gttattgatc tacttttcaa ttgcgccgcc ttcatctata tcggcgctat cattcctttc    960

aatcatttta acgatttgcc cgatctccga gtatggcgat tggttgtgtt ggctatcctc   1020

attcttctag ttcgtcgtct gccttctata atagcgtgtt acaaattcgt tcccgatatc   1080

aagacgttca gagaagctct ttttacggga tggttcgggc ctatgggcgt cggtgctgta   1140
```

```
ttcatctcca ctcttgctcg gtcgtctttg ccagaagggg agcctgaaca gaatacagaa   1200

gcggtggacc gcctaaaaga cgtcatcatg cctgtcacct tatttcttgt attgtcttca   1260

atcgtaactc acggcatgtc aattccattt ttctctcttg gtcgccgggt ccattccatt   1320

acttatactc gatcacgaaa tctttccatg gacacgcgag gcgatgagcc tgcctggaca   1380

actcatgctc ggcgtattat tccaggccag gagatcattg tcaaccgtga tgacgacgac   1440

gaagaaggcg acttgggtgt tagacggatg gacacactca cgagcgattc aaatggtcgt   1500

atcagggaaa agattgagga agaagatagc ggagaaagta gctcatcccg aacaaggcag   1560

ggagaaatga ttgaaatgac agaaaaacgt ggcccggctc gccatggtag ccaggccagc   1620

cagggcgaag cggcggagga aggagagagg tggagaagtt cgggagaaga aagctctgat   1680

cttgcgaatg accctgagac acagagagag gtggaagagg gaatggaaga ggtcgaagat   1740

aaggaaggag gtggtagaag aacgcccccc ctggccaagt acagagaagg aaaccacctc   1800

attgtggaga gaaaagtcaa ggacagtgac gaggttgaag tcgaggtcat ccgaaaccat   1860

ttttccgaca acaagaaaac ggaaagtgac cgcttcactc atccccatcg cctcaagtca   1920

cgagagcttg acgatttgct tcatcacctt cccaaaagcc tcgagcatgc tacttcacgg   1980

gttcaaaatg gcggcaaaga tgcagttgat cgtctcggtc ttgggctgat ggctattaac   2040

actccggaac cgtcaccatc gatcgaatcg cacggcggtc caaggcatga ttatgtcgat   2100

ggcttggaga gaacgcagag cccagagggt cttgcagacg aggataggga tagcgagggc   2160

cggggcgatg tgtcccatgg gggtgattat gaagaaaacg aggccgacta tgaggatgtt   2220

ccgaacgaga ctcgtcggca aaggaggaag aaaatgaaac caccagcaat tgtcgtctct   2280

cggcagaaca gcgccgggct cccgagacga tccatccgct ccaggctgtt cggccgacga   2340

caacattctt ccaactctcc ctcccgtgcc gaagaaggct tagcccctcc caatccatct   2400

cttcttgttc catcctcatc cccttcgcgt cctcaaaaca ttgctgcaga acccgagtcc   2460

atactggcag aagattcgcg cggatcatcc tcaccttccc aatctcaaaa tcttgcgatc   2520

cctctcacaa gaaccctttc agctagccga tcgtcgcctg cggtgcgctt cgccgacgat   2580

gctagtcctt catcggacac agcgcctggg cagtcaaatt atggtactaa cgctccaggt   2640

ttcaagaaga atccggcttt agcaatgtat cgatcggcca gtgtacaaag tacagggtcc   2700

aacaaggatg ggcctagcgt atctttcaaa gaacctgaaa tcaagcgttg a            2751
```

```
<210> SEQ ID NO 22
<211> LENGTH: 170
<212> TYPE: PRT
<213> ORGANISM: Cryptococcus neoformans
<220> FEATURE:
<221> NAME/KEY: PEPTIDE
<222> LOCATION: (1)..(170)
<223> OTHER INFORMATION: an amino acid sequence of Ras1(CNAG_01672.2)
      serotype A H99 strain

<400> SEQUENCE: 22

Met Ser Gly Asn Gly His Tyr Arg Arg Asp Gln Arg Leu Val Val Val
1               5                   10                  15

Gly Cys Gly Ala Phe Arg Glu Tyr Asn Pro Thr Ile Glu Asp Ser Tyr
            20                  25                  30

Arg Lys Gln Val Val Val Asp Asn Glu Ala Thr Thr Leu Glu Ile Leu
        35                  40                  45

Asp Thr Ala Gly Gln Glu Glu Tyr Ala Ala Met Ala Asp Gln Trp Tyr
    50                  55                  60
```

```
Thr Phe Gly Ser Gly Phe Leu Leu Val Tyr Ser Leu Thr Asp Arg Ser
65                  70                  75                  80

Ser Phe Glu Glu Ile Gln Asn Phe His Arg Glu Ile Leu Arg Val Lys
                85                  90                  95

Asp Arg Asp Tyr Val Pro Cys Val Ile Ile Cys Asn Lys Cys Asp Leu
            100                 105                 110

Gln Lys Tyr Arg Ser Val Gly Gln Leu Glu Gly Arg Glu Leu Ala Arg
        115                 120                 125

Ser Val His Ala Pro Phe Ile Glu Cys Ser Ala Ala Glu Arg Val Asn
    130                 135                 140

Val Asp Val Ala Phe Asn Glu Leu Val Lys Leu Val Arg Lys Asp Glu
145                 150                 155                 160

Arg Val Arg Ile Asn Tyr Asp Ile Ala Phe
                165                 170


<210> SEQ ID NO 23
<211> LENGTH: 227
<212> TYPE: PRT
<213> ORGANISM: Cryptococcus neoformans
<220> FEATURE:
<221> NAME/KEY: PEPTIDE
<222> LOCATION: (1)..(227)
<223> OTHER INFORMATION: an amino acid sequence of Ras2(CNAG_04762.2)
      serotype A H99 strain

<400> SEQUENCE: 23

Met Leu Phe Lys Ile Thr Val Leu Gly Asp Gly Gly Val Gly Lys Thr
1               5                   10                  15

Ala Ile Thr Val Gln Thr Cys Lys Thr Tyr Asp Pro Thr Ile Glu Asp
            20                  25                  30

Cys Tyr Arg Lys Gln Trp Val Val Asp Glu Gln Pro Cys Leu Leu Glu
        35                  40                  45

Val Leu Asp Thr Ala Gly Gln Glu Glu Tyr Thr Ala Leu Arg Asp Gln
    50                  55                  60

Trp Ile Arg Glu Gly Glu Gly Phe Leu Ile Val Tyr Ser Ile Thr Ser
65                  70                  75                  80

Arg Pro Thr Phe Glu Arg Val Glu Arg Ile Val Glu Arg Val Leu Arg
                85                  90                  95

Val Lys Asp Glu Ser Gly Leu Pro Leu Pro Pro Leu Ser Ser Ser Leu
            100                 105                 110

Ser Asn Asp Pro Tyr Gly Leu Ala Thr Ser Arg Ser Thr Pro Thr Ser
        115                 120                 125

Ala Gly Gly Gly Gly Gly Ser Gly Gly Gly Gly Met Trp Ala Ala Arg
    130                 135                 140

Val Pro Ile Val Ile Val Gly Asn Lys Lys Asp Met Phe His Ser Arg
145                 150                 155                 160

Glu Val Ser Thr Asp Glu Gly Ala Ser Leu Ala Arg Arg Leu Gly Cys
                165                 170                 175

Glu Phe Tyr Glu Ala Ser Ala Lys Thr Asn Ser Asn Val Glu Ala Ala
            180                 185                 190

Phe Lys Cys Leu Val Lys Lys Ile Lys Leu Ala Lys Gln Gly Gly Val
        195                 200                 205

Ala Val Gln Ala Glu Arg Val Gly Gly Arg Lys Lys Lys Gln Lys Cys
    210                 215                 220

Val Val Leu
225
```

<210> SEQ ID NO 24
<211> LENGTH: 1112
<212> TYPE: PRT
<213> ORGANISM: Cryptococcus neoformans
<220> FEATURE:
<221> NAME/KEY: PEPTIDE
<222> LOCATION: (1)..(1112)
<223> OTHER INFORMATION: an amino acid sequence of Cdc24(CNAG_04243.2)
serotype A H99 strain

<400> SEQUENCE: 24

```
Met Ser Val Ser Gly Pro Ile Ser Arg Arg Arg Ile Gly Ser Val Ser
1               5                   10                  15

Gln Arg Gly Asn Glu Ser Leu Pro Gln Leu Asp Ile Gln Ser Ile Gln
            20                  25                  30

Met Pro Ser Asn Pro Gln Asn Ala Leu Ala Leu Lys Thr Ala Ala Leu
        35                  40                  45

Ser Thr Ser Thr Arg Ser Leu His Gln Ile Cys Ser Ile Leu Lys Lys
    50                  55                  60

Arg Leu Leu Cys Val Asp Gly Phe Lys Ala Phe Leu Glu Gln Pro Pro
65                  70                  75                  80

Asn Ala Glu Pro Leu Asp Val Val Ser His Met Cys His Leu Phe Arg
                85                  90                  95

Leu Gly Ser Pro Leu Cys His Leu Tyr Asn Leu Leu Ile Pro Ser Phe
            100                 105                 110

Val Asp Cys Leu Ser Pro Leu Tyr Ala Asp Leu Pro Ala Pro Ala Lys
        115                 120                 125

Ile Glu Tyr Asp Phe Pro Gln Phe Tyr Asp Ser Pro Asn Gly Val Arg
    130                 135                 140

Asn Trp Ala Lys Arg Pro Glu Asn Ala Lys Pro Cys Gln Arg Tyr Ile
145                 150                 155                 160

Ala Ala Phe Cys Met Ala Met Lys Lys Arg Ile Glu Glu Gly Arg Trp
                165                 170                 175

Thr Ser Asp Met Trp Ala Leu His Glu Leu Trp Gly Lys Ser Thr Gly
            180                 185                 190

Glu Asp Ile Glu Ala Tyr Asp Ser Thr Gly Leu Met Lys Val Leu Ser
        195                 200                 205

Thr Val Glu Glu Met Leu Asp Asn Leu Pro Glu Ser Ala Met Ser Pro
    210                 215                 220

Ile Ser Pro Gln Thr Pro Phe Thr Ala Ser Gly Ser Ile Ala Gln Arg
225                 230                 235                 240

Ala Gln Ser Arg Gln Ser Tyr Asp Leu Pro Phe Ser Met Gly Gly Ile
                245                 250                 255

Gly Ser Gly Ala Ser Ala Val Ala Asn Met Ala Ala Thr Met Asn Gly
            260                 265                 270

Gly Val His Val Glu Thr Gly Pro Ser Glu Asn Ser Pro Thr Ala Ala
        275                 280                 285

Glu Met Gln Arg Gly Leu Ser Thr Ser Leu Ala Glu Ala Asn Ala Phe
    290                 295                 300

Lys Ser Val Glu Glu Leu Val Ala Ser Glu Lys Ser Tyr Val Gln Glu
305                 310                 315                 320

Leu Glu Ile Leu Val Arg Cys Ser Gln Glu Met Leu Glu Ala Gln Leu
                325                 330                 335

Val Ser Thr Glu Thr Asn His Gln Ile Phe Ser Asn Leu Ser Lys Ile
            340                 345                 350
```

-continued

```
Leu Asp Phe His Arg Lys Phe Leu Ile Lys Leu Glu Thr Glu Tyr Glu
        355                 360                 365

Pro Ile Gln Glu Arg Gly Pro Gly Ala Trp Ala Glu Gly Val Trp Gly
    370                 375                 380

Arg Pro Phe Ile Leu Ser Glu Ala Glu Phe Asp Cys Tyr Gly Pro Tyr
385                 390                 395                 400

Cys Ala Asn Tyr Leu Asp Ala Ile Thr Val Val Asn Glu Gln Met Pro
                405                 410                 415

Ile Leu Met Arg Gly Gln Glu Leu Ser Pro Gly Glu Arg Pro Cys Leu
            420                 425                 430

Asp Pro Gln Arg Glu Leu Gln Ala Phe Met Ile Lys Pro Ile Gln Arg
        435                 440                 445

Ile Thr Lys Tyr Gly Leu Leu Leu Asp Ala Ile Leu His Ala Thr Ala
    450                 455                 460

Lys His Glu Tyr Pro Phe Arg Pro Glu Leu Glu Glu Ala Ser Ala Ala
465                 470                 475                 480

Val Lys Arg Ile Ala Ala Gly Ile Asn Glu Val Thr Asp Phe Lys Ala
                485                 490                 495

Lys Gln Ala Thr Val Arg Glu Leu Ile Glu Arg Val Asp Asp Trp Lys
            500                 505                 510

Gly His Asp Val Asp Lys Phe Gly Pro Leu His Ile Asp Asp His Phe
        515                 520                 525

Thr Val Thr Lys Ala Asp Gln Pro Arg Glu Tyr His Val Phe Leu Phe
    530                 535                 540

Glu Lys Met Met Leu Cys Cys Lys Glu Ile Thr Pro Glu Lys Lys Lys
545                 550                 555                 560

Gln Asn Lys Asn Ser Ser Met Leu Arg Lys Asp Arg Gly Thr Ser Lys
                565                 570                 575

Ser Gly Pro Leu Asp Lys Lys Lys Leu Ala Leu Lys Gly Arg Ile Phe
            580                 585                 590

Val Ser Asn Ile Lys Glu Ala Thr Ile Leu Pro Thr Glu Pro Gly Asp
        595                 600                 605

Ala Tyr Gly Val Ala Arg Leu Leu Ile Gly Trp Thr Ile Pro Leu Arg
    610                 615                 620

Asn Gln Asp Gly Tyr His Asp Asp Gln Glu Asp Ser Phe Val Met Ile
625                 630                 635                 640

Gly Lys Ser Glu Glu Gln Met Arg Lys Trp Ser Glu Lys Val Met Glu
                645                 650                 655

Leu Ala Asn Asn Glu Arg Lys Ile Gln Glu Asp Met Arg Ala Ala Arg
            660                 665                 670

Met Lys Ala Gly Arg Phe Ser Gly Ser Glu Arg Gln Tyr Tyr Gln His
        675                 680                 685

Ser Phe Phe Gly Pro Pro Thr Pro Ala Thr Glu His Pro Pro Met Thr
    690                 695                 700

Pro Phe Asn Met Pro Pro Leu Pro Asn Gly Ser Ala Thr Pro Tyr Tyr
705                 710                 715                 720

Ser Glu Asp Glu Asp Pro Glu Gly Leu Arg Ser Gly Arg Thr Thr Pro
                725                 730                 735

Ser Ile Leu Gly His His Pro Tyr Ala Tyr Ser Gly Gln Pro Ser Ala
            740                 745                 750

Ser Arg Arg Val Gln Ser Gln Gln Ser Met Thr Ser Val Met Pro Thr
        755                 760                 765
```

-continued

```
Glu Leu Arg Ala Arg Ala Met Thr Glu Asp Gln Tyr Gly Pro Ser Met
    770                 775                 780

Thr Gln Trp Arg Thr Gln Gln Pro Met Ala Pro Pro Leu Pro Arg Leu
785                 790                 795                 800

Thr Ser Ala Met Ser Gly Met Ser Val Ala Ser Glu Leu Ser Phe Gly
                805                 810                 815

Ser Gly Pro Asn Asn Ile Gly Ile Arg Thr Gly Met Val Arg Gln Met
            820                 825                 830

Ser Ser Thr Arg Leu Pro Arg Ala Thr Glu Val Asp Glu Ala Glu Glu
        835                 840                 845

Asn Pro Val Asp Thr Arg Asp Ser Tyr Gly Arg Tyr Gly Ser Leu Arg
    850                 855                 860

Gly Ile Met Arg Ala Pro Ser His Ala Met Pro Ser Val Pro His Pro
865                 870                 875                 880

Pro Pro Leu Arg Asn Arg Ser Ala Ser Ser Pro Asn Val Tyr Gln Gln
                885                 890                 895

Pro Thr Val Thr Gly Ala Ala Ser Leu Pro Tyr Thr Ala Gly Pro Asn
            900                 905                 910

Gly Thr Trp Thr Thr Ser Pro Leu Ala Ser Thr Leu Gln Met Ser Thr
        915                 920                 925

His Pro Tyr Val Gln Ser Thr Pro Val Pro Gly Phe Gly Pro Ser Ser
    930                 935                 940

Ser Thr Thr Leu Val Gly Gly Thr Ala Tyr Phe Asn Lys Arg Met Ser
945                 950                 955                 960

Asn Glu Lys Arg Ser Ser Gly Glu Ser His His Ser Thr Thr Thr Thr
                965                 970                 975

Asp Thr Ser Asp Gln Thr Ser Pro Ala Thr Pro Tyr Gly Ser Gly Asn
            980                 985                 990

Gly Asp Ile Arg Gly Pro Ser Arg  Gln Asn Ser Gly Asp  Asn Val Ser
        995                 1000                1005

Gly Ser  Val Leu Val Lys Leu  Arg Phe Gly Asn Asp  Gln Phe Ile
    1010                1015                1020

Leu Gly  Val Ser Gln Gly Ile  Asp Phe Ile Thr Leu  Tyr Gln Lys
    1025                1030                1035

Ile His  Lys Lys Ile Arg Leu  Cys Ser Ser Ser Asn  Arg Pro Thr
    1040                1045                1050

Asn Glu  His Asp Lys Leu Gln  Ile Arg Tyr Val Asp  Asn Asp Gly
    1055                1060                1065

Asp Glu  Ile Gln Val Lys Phe  Asp Ser Asp Val Glu  Leu Met Phe
    1070                1075                1080

Glu Asp  Ala Arg Asp Gln Ala  Gly His Ile Asn Leu  Ile Ala Arg
    1085                1090                1095

Trp Ala  Glu Asp Arg Arg Gly  Thr Pro Gln Gly Glu  Ile Tyr
    1100                1105                1110
```

<210> SEQ ID NO 25
<211> LENGTH: 432
<212> TYPE: PRT
<213> ORGANISM: Cryptococcus neoformans
<220> FEATURE:
<221> NAME/KEY: PEPTIDE
<222> LOCATION: (1)..(432)
<223> OTHER INFORMATION: an amino acid sequence of Gpa1(CNAG_04505.2)
      serotype A H99 strain

<400> SEQUENCE: 25

-continued

```
Met Gly Gly Cys Met Ser Thr Pro Glu Ala Pro Arg Lys Ala Ala Glu
1               5                   10                  15

Thr Lys Gln Val Pro Ser Thr Ser Thr Thr Ser Arg Pro Pro Gln Ala
            20                  25                  30

Ser Thr Ser Ala Thr Ala Thr Ala Ala Gly Ala Ser Thr Ser Pro Pro
        35                  40                  45

Asn Gly Thr Ala Asn Gly Ile Lys Gly Asp Thr Thr Ala Ala Asn Arg
    50                  55                  60

Thr Gly Ala Ser Ala Gly Gln Gly Ile Val Ala Ala Leu Ala Ser Thr
65                  70                  75                  80

Glu Pro Pro Gly Ala Gln Asp Ser Lys Gly Asn Lys Asp Arg Ser Asn
                85                  90                  95

Gln Ile Asp Arg Gln Leu Glu Asp Asp Gln Lys Lys Phe Arg Lys Glu
            100                 105                 110

Cys Lys Ile Leu Leu Leu Gly Ser Gly Glu Ser Gly Lys Ser Thr Ile
        115                 120                 125

Val Lys Gln Met Lys Ile Ile His Gln Asn Gly Tyr Ser Lys Asp Glu
    130                 135                 140

Leu Leu Ser Phe Arg Gly Val Ile Tyr Lys Asn Val Leu Asp Ser Ala
145                 150                 155                 160

Gln Ala Leu Ile Met Ala Met Arg Lys Ile Gly Val Asp Pro Glu Asp
                165                 170                 175

Ala Asn Asn Arg Ser Tyr Ala Asp Arg Ile Leu Glu Tyr Arg Met Asp
            180                 185                 190

Ala Asp Leu Asn Ala Val Ile Pro Ser Glu Ile Leu Tyr Asn Ile Glu
        195                 200                 205

Ser Leu Trp His Asp Pro Val Ile Pro Ser Val Met Asp Arg Ser Ser
    210                 215                 220

Glu Phe Tyr Ile Met Asp Ser Ala Thr Tyr Phe Phe Ala Asn Ile Arg
225                 230                 235                 240

Lys Ile Ala Gly Pro Asp Tyr Val Pro Asp Glu Ala Asp Val Leu Arg
                245                 250                 255

Ala Arg Thr Lys Thr Thr Gly Ile Ser Glu Thr Arg Phe Asn Met Gly
            260                 265                 270

Gln Leu Ser Ile His Met Phe Asp Val Gly Gly Gln Arg Ser Glu Arg
        275                 280                 285

Lys Lys Trp Ile His Cys Phe Glu Ala Val Thr Ser Ile Ile Phe Cys
    290                 295                 300

Val Ala Leu Ser Glu Tyr Asp Gln Val Leu Leu Glu Glu Ser Gly Gln
305                 310                 315                 320

Asn Arg Met Gln Glu Ser Leu Val Leu Phe Glu Ser Val Ile Asn Ser
                325                 330                 335

Arg Trp Phe Leu Arg Thr Ser Val Ile Leu Phe Leu Asn Lys Ile Asp
            340                 345                 350

Leu Phe Lys Gln Lys Leu Pro Lys Val Pro Leu Val Gln Tyr Phe Pro
        355                 360                 365

Glu Tyr Thr Gly Gly Ala Asp Ile Asn Lys Ala Ala Lys Tyr Ile Leu
    370                 375                 380

Trp Arg Phe Thr Gln Thr Asn Arg Ala Arg Leu Ser Val Tyr Pro His
385                 390                 395                 400

Leu Thr Gln Ala Thr Asp Thr Ser Asn Ile Arg Leu Val Phe Ala Ala
                405                 410                 415

Val Lys Glu Thr Ile Leu Gln Asn Ala Leu Arg Asp Ser Gly Ile Leu
```

420 425 430

<210> SEQ ID NO 26
<211> LENGTH: 2250
<212> TYPE: PRT
<213> ORGANISM: Cryptococcus neoformans
<220> FEATURE:
<221> NAME/KEY: PEPTIDE
<222> LOCATION: (1)..(2250)
<223> OTHER INFORMATION: an amino acid sequence of Cac1(CNAG_03202.2) serotype A H99 strain

<400> SEQUENCE: 26

Met Pro Met Phe Arg Arg Ser Ala Ser Ser His Ser Thr Ser Asp Ala
1 5 10 15

Ala Ala Pro Pro Thr Ile Thr Asn Val Thr Glu Gly Ser Pro Val Ser
20 25 30

Ser Gly Ser Ile Thr Arg Gln Lys Arg Ser Arg Ser His Gly Gly Gly
35 40 45

Gly Ser Pro Ala Ser Thr Phe Ser Ser Arg Phe Gly Ile Ser Arg His
50 55 60

Leu Ser His Gln Phe Gln Gln Pro His Glu Gln Glu Gln Gly Gln Val
65 70 75 80

Pro Pro Pro Glu Lys Pro Ala Thr Arg Glu Val Pro Val Ser Leu Glu
85 90 95

Pro Glu Ile Tyr Gly Ser Glu Ala Gly Glu Asp Ser Asn Phe Gly Gln
100 105 110

Glu Pro Ala Gly Glu Gln Leu Ile Pro Glu Thr Arg Ser Ser Ser Arg
115 120 125

Gln Ser Arg Arg Ser Ser Arg Glu Leu Ser Val Gln Thr Ile Glu Pro
130 135 140

Ser Ser Asp Asp Glu Ile Arg Ser Pro Glu Lys Arg Arg Val Ser Pro
145 150 155 160

Leu Met Lys Arg Leu Gly Glu Glu Pro Pro Phe Met Leu Pro His Pro
165 170 175

Ser Leu Ser Asp Ser Thr Tyr Gln Ala Tyr Pro Gly Val Val Ile Gly
180 185 190

Ser Phe Ala Gly Gly Gly Pro Asp Thr Leu Phe Gly Asn Gly Met Gln
195 200 205

Leu Glu Gly Thr Val Asp Asp Ile Leu Asp Pro Asn Ala Ala Arg Gln
210 215 220

Glu Asp Arg Gly Asn Gln Val Pro Ala Gly Ala Asn Ile Ala Pro Trp
225 230 235 240

Leu Met Asp Asp Gly Pro Pro Ser Arg Ser Glu Asn Pro Ser Pro Ala
245 250 255

Leu Ser Glu Thr Gln Glu Arg Pro Val Lys Gly Pro Ala Ala Ala Leu
260 265 270

Arg Glu Lys Asp Pro Arg Lys Thr Ser Thr Val Leu Asn His Phe Ser
275 280 285

Ser Val Pro Ser Leu Pro Lys Ile Arg Arg His Gly Arg Ala Ala Thr
290 295 300

Thr Thr Pro Asp Gln Thr Pro Arg Gly Ser Thr His Ser Gln Ser Asn
305 310 315 320

Leu Ala Ser Ser Ser Ser Ser Leu Asn Asn Glu Ser Arg Glu Ser Arg
325 330 335

Ala Gly Ser Asp Asp Ser Ile Gln Thr Thr Leu Thr Gln Lys Gly Arg

```
            340                 345                 350

Arg Gln Ser Pro Gly Glu Trp Gly Gln Ala Ser Ala Val Pro Pro Pro
        355                 360                 365

Ser Lys Gly Thr Arg Pro Gly Arg Phe Gly Ser Thr Ala Ser Ile Ile
    370                 375                 380

Ser Gly Thr Gly Ser Val Gly Glu Lys Lys Lys Ser Leu Phe Gly Gly
385                 390                 395                 400

Leu Leu Lys Arg Lys Thr Asn Pro Asn Leu Ser Leu Asn Pro Ile Ser
                405                 410                 415

His Asp Phe Thr Thr Ser Glu His Arg Gly Ser Ala Gly Ser Ile Pro
            420                 425                 430

Leu Ser Ala Ser Ser Ser Lys Leu Ser Ser Cys Ser Leu Ser Ser Leu
        435                 440                 445

Pro Ser Lys Ser Pro Pro Phe Thr Ser Pro Pro Glu Ala Phe Ser Arg
    450                 455                 460

Gln Phe Leu Pro Ala Asn Tyr Val His Glu Gly Ala Val Ser Pro Leu
465                 470                 475                 480

Gln Glu Ile Ser Glu Ser Pro Phe His Leu Asp Met Asn Leu Asp Asp
                485                 490                 495

Met Glu Gly Ile Ile Asp Pro Ala Lys Ala Gly Leu Pro Ser Thr Val
            500                 505                 510

Ala Tyr Arg Pro Ser Ala Ser Ser Glu Val Thr Thr Asp Ser Ser Ala
        515                 520                 525

Ser Glu Ser Met Arg Leu Glu Glu Ala Leu Asn Gln Thr Ser Ser Phe
    530                 535                 540

Gly Thr Ser Val Ser Gly Ala Ser Arg Gly Ser Asp Gly Thr Lys Met
545                 550                 555                 560

Pro Gly Arg Ile Val Leu Gly Glu Ala Glu Arg Leu Pro Thr Pro Phe
                565                 570                 575

Thr Gly Thr Asp Pro Phe Gln Gln His Arg Glu Ser Ala Ser Thr Thr
            580                 585                 590

Gly Ser Asp Gly Lys Pro Phe Ser Pro Pro Ser Pro His Thr Leu Ser
        595                 600                 605

Pro Lys His His Leu Pro Ser Ser Ser Ala Asn Gln Pro Arg Arg Pro
    610                 615                 620

Ser Ala Leu Arg Asn Val Glu Thr Gly Gln Val Asp Glu Thr Pro Gln
625                 630                 635                 640

Leu Ser Ala Ser Glu Gly Ser Ile Gln Pro Ile Ser Pro Ser Trp Ala
                645                 650                 655

Gly Gly Ser Gly Ile Thr Val Phe Asn Asp Pro Phe Ser Thr Ser Arg
            660                 665                 670

Gln Arg Gln Glu Gln Pro Pro Asn Ser Ala Gly Leu Ser Pro Ser Thr
        675                 680                 685

Thr Ala Tyr Pro Ser Ala Val Thr Gln Pro Gly Pro Ser Thr Ala Arg
    690                 695                 700

Phe Leu Ile Thr Ala Gly Ser Thr Thr Pro Ser Ala Ala Trp Ala Ala
705                 710                 715                 720

Pro Glu Ser Trp Gly Val Glu Ala Asp Glu Ala Pro Ala Glu Glu Ile
                725                 730                 735

Thr Ser Ser Asp Glu Asp Asp Trp Ala Gly Leu Gly Val Glu Glu Val
            740                 745                 750

Ala Ser Ala Ser Pro Thr Ser Asp Thr Leu Pro Ser Pro Pro Thr Ser
        755                 760                 765
```

```
Pro Arg Ala Ser Ser Leu Pro Ser Pro Lys Arg Ala Pro Pro Phe Gly
    770                 775                 780

Phe Lys Ser Gln Gln Arg Ala Lys Pro Gly Thr Ser Gly Thr Thr Asp
785                 790                 795                 800

Ser Thr Thr Ser Ala Ala Gly Arg Arg Lys Gly Lys Arg Val Gly Ser
                805                 810                 815

Ser Gly Arg Pro Ala Thr Gly Arg Pro Gly Thr Ser Gly Ser Ala Tyr
            820                 825                 830

Asn Pro Ser Ser Leu His Trp Ile Arg Ile Tyr Arg Ala Asp Lys Ser
        835                 840                 845

Tyr Met Leu Tyr Asn Leu Pro Leu Asn Thr Ser Thr Gly Glu Leu Leu
    850                 855                 860

Ala Leu Leu Ala Ala Gln Ala Glu Gln Gly Met Val Arg Gly Lys Asn
865                 870                 875                 880

Val Ala Ile Asn Met Lys Leu Tyr Ile Cys Glu Arg Gly Gln Asn Arg
                885                 890                 895

Met Leu Leu Pro Ser Glu Lys Pro Leu Thr Ile Gln His Arg Arg Leu
            900                 905                 910

Leu Gln Leu Gly His Thr Glu Ala Asp His Leu Asp Glu Leu Gly Lys
        915                 920                 925

Asn Asp Met Ala Val Leu Cys Arg Phe Ile Tyr Gln Ala Pro Ile Leu
    930                 935                 940

Pro Ile Met Asp Pro Glu Glu Glu Ser Ser Tyr Asp Ser Phe Glu Phe
945                 950                 955                 960

Ile Asp Ile Ala Ser Arg Asp Leu Gln Thr Ile Pro Ile Phe Leu His
                965                 970                 975

Leu His Ala His Asp Ile Ile Ile Leu Asn Ile Ser Lys Asn Pro Met
            980                 985                 990

Thr Asp Ile Pro Leu Asp Phe Ile  Gln Ala Cys Thr Ser  Leu Lys Glu
        995                 1000                1005

Leu Arg  Met Ser Asn Met Ala  Leu Lys Arg Val Pro  Ile Ser Ile
    1010                1015                1020

Arg Ala  Ser Thr Thr Leu Ala  Arg Leu Asp Val Ser  Cys Asn Arg
    1025                1030                1035

Ile Ala  Asp Leu Glu Ser Val  Ala Leu His Glu Val  Glu Thr Leu
    1040                1045                1050

Val Ser  Leu Lys Val Gln Asn  Asn Lys Leu Thr Ser  Met Pro Ser
    1055                1060                1065

Tyr Phe  Ala Gln Met Lys Ser  Leu Lys Tyr Leu Asn  Ile Ser Asn
    1070                1075                1080

Asn Lys  Phe Glu Thr Phe Pro  Ser Val Val Cys Glu  Met Ser Asn
    1085                1090                1095

Leu Val  Asp Leu Asp Val Ser  Phe Asn Asn Ile Ala  Glu Leu Pro
    1100                1105                1110

Ala Lys  Met Ser Asp Leu Lys  Ser Leu Glu Lys Leu  Gly Leu Tyr
    1115                1120                1125

Ser Asn  Asp Ile Ser Lys Phe  Pro Glu Ser Phe Cys  Thr Leu Ala
    1130                1135                1140

Asn Leu  Arg Ile Leu Asp Val  Arg Arg Asn Lys Ile  Thr Asp Leu
    1145                1150                1155

Ser Ala  Val Tyr Ala Leu Pro  Asn Leu Ala Thr Leu  Gln Ala Asp
    1160                1165                1170
```

```
Asn Asn  Asn Ile Val Thr Leu  Asp Ala Gln Leu Gly  Ala Asn Val
    1175                 1180                 1185

Arg Gln  Phe Ser Val Pro His  Asn Ser Val Thr Arg  Phe Thr Leu
    1190                 1195                 1200

Ala Pro  Pro Pro Asn Met Ala  Val Val Thr Tyr Met  Leu Thr Asn
    1205                 1210                 1215

Leu Asp  Leu Ser His Gly Lys  Ile Ser Thr Leu Ala  Asp Glu Ala
    1220                 1225                 1230

Phe Ser  Gly Leu Thr Asn Leu  Val Thr Leu Asn Leu  Asn Phe Asn
    1235                 1240                 1245

Gln Phe  Thr Lys Leu Pro Ala  Thr Leu Gly Arg Leu  Thr Ser Leu
    1250                 1255                 1260

Glu Val  Phe Ser Cys Thr Asp  Asn Met Leu Asn Leu  Val Pro Ala
    1265                 1270                 1275

Gly Phe  Gly Lys Leu Gln Arg  Leu Arg Met Ile Asn  Leu His Asn
    1280                 1285                 1290

Asn Asn  Leu Lys Ser Leu Pro  Glu Asp Leu Trp Ala  Cys Gly Ala
    1295                 1300                 1305

Leu Glu  Val Phe Asn Ala Ser  Ser Asn Leu Leu Asp  Ser Phe Ile
    1310                 1315                 1320

Pro Pro  Pro Ala Asp Ile Glu  Ser Val Val Gly Arg  Val Gly Ser
    1325                 1330                 1335

Gly Thr  Ser Gln Thr Ser Asn  Gly Arg Lys Lys Tyr  Ser Val Pro
    1340                 1345                 1350

Pro Ile  Gly Leu Ser Ile Arg  Lys Leu Phe Leu Ala  Asp Asn Arg
    1355                 1360                 1365

Leu Asn  Asp Asp Val Phe His  Trp Ile Ser Leu Met  Pro Ser Leu
    1370                 1375                 1380

Arg Ile  Ile Asn Leu Ser Phe  Asn Asp Ile Tyr Glu  Leu Thr Asn
    1385                 1390                 1395

Leu Pro  Ser Glu Asp Leu Glu  Lys Leu Gln Ser Leu  Lys Val Leu
    1400                 1405                 1410

His Leu  Asn Gly Asn Lys Leu  Gln Thr Leu Pro Ser  Glu Leu Gly
    1415                 1420                 1425

Ala Ile  Lys Thr Leu Gln His  Leu Asp Val Gly Ser  Asn Val Leu
    1430                 1435                 1440

Lys Tyr  Asn Ile Ala Asn Trp  Pro Tyr Asp Trp Asn  Trp Asn Trp
    1445                 1450                 1455

Asn Thr  Ser Leu Arg Tyr Leu  Asn Leu Ser Gly Asn  Lys Arg Leu
    1460                 1465                 1470

Glu Ile  Lys Pro Thr Ser Ala  His Glu Met Ser His  Ala Ser Ser
    1475                 1480                 1485

Phe Arg  Lys Glu Leu Ser Asp  Phe Thr Ala Leu Thr  Gln Leu Arg
    1490                 1495                 1500

Val Leu  Gly Leu Met Asp Val  Thr Leu Arg Ile Pro  Ser Leu Pro
    1505                 1510                 1515

Asp Glu  Ser Glu Glu Lys Arg  Val Arg Thr Ser Phe  Ser Asp Ile
    1520                 1525                 1530

Asn Asn  Met Ala Tyr Gly Ile  Ser Asp Met Leu Gly  Ser Ile Asp
    1535                 1540                 1545

Asn Leu  Ala Met Phe Asp Leu  Val Val Pro His Phe  Arg Gly Lys
    1550                 1555                 1560

Glu Asn  Glu Cys Leu Phe Gly  Met Phe Gly Arg Val  Thr Thr Thr
```

```
    1565                1570                1575

Leu Gln Gly Gly Lys Ile Ala Lys Tyr Val Gln Glu Ile Phe Ala
    1580                1585                1590

Glu Thr Leu Thr Ala His Leu His Gln Leu Glu Pro Gly Glu Glu
    1595                1600                1605

Pro Ser Glu Ala Leu Arg Arg Thr Phe Leu Leu Gly Asp Arg Lys
    1610                1615                1620

Ala Phe Glu Phe Phe Ser Asp Lys Leu Gln Leu Glu Lys Glu Arg
    1625                1630                1635

Lys Pro Ser Trp Thr Ser Phe Ala Ser Phe Asp Ser Met Phe Arg
    1640                1645                1650

Gly Trp Thr Pro Gly Val Asn Ser Val Leu Arg Thr Gly Ala Ser
    1655                1660                1665

Gly Ala Val Val Tyr Leu Val Asp Lys Val Leu His Val Gly Ser
    1670                1675                1680

Ile Gly Asp Thr Leu Val Val Leu Ser Arg Lys Gly Asp Ala Glu
    1685                1690                1695

Leu Leu Ser Lys Arg His Asp Pro Thr Asp Arg Glu Glu Ser Ala
    1700                1705                1710

Arg Ile Arg Lys Ala Glu Ala Trp Val Ser Thr Lys Gly Phe Val
    1715                1720                1725

Asn Asp Asp Lys Asp Leu Asp Ile Ser Arg Ala Phe Gly Tyr Trp
    1730                1735                1740

His Glu Cys Pro Ala Val Asn Ala Ala Pro Glu Ile Arg Thr Arg
    1745                1750                1755

Arg Leu Gln Glu Ser Asp Glu Phe Val Ile Ile Gly Asn His Ala
    1760                1765                1770

Leu Trp Gln Phe Cys Ser Tyr Gln Thr Ala Val Asp Ile Ala Arg
    1775                1780                1785

Thr Glu Arg Asp Asp Pro Met Met Ala Ala Gln Lys Leu Arg Asp
    1790                1795                1800

Phe Ala Ile Ser Tyr Gly Ala Glu Gly Asn Val Met Val Met Val
    1805                1810                1815

Val Asn Val Ser Asp Leu Phe Leu Ala Lys Gly Gly Arg Ala Arg
    1820                1825                1830

Gly Pro Ser Lys Gln Thr Ala Thr Asp Ala Asn Ala Asp Val Glu
    1835                1840                1845

Gly Tyr Ala Val Ala Lys Arg Gln Val Arg Arg Arg Tyr Asp Glu
    1850                1855                1860

Val Gly Asp Arg Thr Leu Asn Arg Leu Gln Gln Glu Ile Glu Pro
    1865                1870                1875

Pro Val Gly Gln Val Ala Ile Val Phe Thr Asp Ile Val Asn Ser
    1880                1885                1890

Thr His Leu Trp Glu Thr Asn Pro Ala Met Pro Thr Ala Ile Lys
    1895                1900                1905

Met His His Asn Leu Met Arg Arg Gln Leu Arg Leu Asp Gly Gly
    1910                1915                1920

Tyr Glu Val Lys Thr Glu Gly Asp Ser Phe Met Val Ser Phe Gln
    1925                1930                1935

Ser Val Ala Ser Ala Leu Leu Trp Ser Phe Asn Cys Gln Ile Gly
    1940                1945                1950

Leu Leu Gln Gln Glu Trp Pro Arg Glu Leu Leu Glu Ala His Asp
    1955                1960                1965
```

```
Gly Lys Val Val Tyr Asp Ser Asn Gly Thr Ile Val Gln Arg Gly
    1970                 1975                 1980

Leu Arg Val Arg Met Gly Val His Trp Gly Ala Pro Glu Cys Glu
    1985                 1990                 1995

Lys Asp Pro Ile Thr Arg Arg Met Asp Tyr Tyr Gly Pro Met Val
    2000                 2005                 2010

Asn Arg Ala Ala Arg Ile Asn Ala Ser Ala Asp Gly Gly Gln Leu
    2015                 2020                 2025

Met Ala Ser Gln Asp Val Leu Asn Glu Ile Ala Pro Leu Met Glu
    2030                 2035                 2040

Tyr Leu Asn Ser Ser Asp Glu Gln Val Leu Asn Asp Leu Gln Gly
    2045                 2050                 2055

Asp Leu Lys Arg Glu Val Met Glu Leu Arg Arg Ile Gly Leu Glu
    2060                 2065                 2070

Val Arg Asp Met Gly Asp Arg Lys Leu Lys Gly Leu Glu Val Pro
    2075                 2080                 2085

Glu Arg Leu His Leu Leu Tyr Pro Lys Thr Leu Ala Gly Arg Leu
    2090                 2095                 2100

Glu Ile Ser Asn Glu Ile Arg Ala Glu Val Glu Val Asn Asp Ala
    2105                 2110                 2115

Arg Lys Ser Ala Glu Arg Gln Arg Ser Val Asp Ile Asp Gln Val
    2120                 2125                 2130

Tyr Gln Leu Ser Asp Ile Ala Leu Arg Leu Glu Ala Val Cys Cys
    2135                 2140                 2145

Tyr Asn Pro Thr Pro Ser Ser Pro Gly Asp Thr Pro Thr Ala Gly
    2150                 2155                 2160

Val Met Arg Leu His Pro Pro Ala Ser Tyr Leu Gly Pro Ser Ile
    2165                 2170                 2175

Arg Glu Asp Met Asn Asp Glu Glu Leu Trp Thr Ile Ile Glu Ser
    2180                 2185                 2190

Leu Val Gly Arg Ile Glu Asn Val Met Ser Thr Leu Tyr Leu Lys
    2195                 2200                 2205

Asn Phe Gly Glu Phe Ser Ala Val Leu Ala Ala Leu Glu Ser Ala
    2210                 2215                 2220

Thr Lys Ile Asp Gln Lys Leu Ile Val His Ala Leu Ala Leu Met
    2225                 2230                 2235

Asn Glu Ala Met Gly Lys Asp Glu Glu Asn Ala Ile
    2240                 2245                 2250
```

<210> SEQ ID NO 27
<211> LENGTH: 499
<212> TYPE: PRT
<213> ORGANISM: Cryptococcus neoformans
<220> FEATURE:
<221> NAME/KEY: PEPTIDE
<222> LOCATION: (1)..(499)
<223> OTHER INFORMATION: an amino acid sequence of Aca1(CNAG_05218.2) serotype A H99 strain

<400> SEQUENCE: 27

```
Met Ala Thr Ser Gln Gly Ile His Ser Ile Ser Thr Ile Leu Arg Leu
1               5                   10                  15

Glu Asp Ile Ala Val Thr Gln Ala Pro His Gly Ser Ser Val Lys Ser
            20                  25                  30

Pro Ala Pro Ala Ser Asp Thr Pro Thr Gly Val Ala Pro Pro Ala Pro
        35                  40                  45
```

-continued

```
Pro Pro Pro Pro Ala Pro Glu Ala Pro Lys Ala Ala Glu Met Thr Gln
    50                  55                  60

Pro Ala Gln Ser Pro Ala Ser Lys Val Tyr Gln Asp Glu Ile Ile Asn
65                  70                  75                  80

Gly Ala Leu Asn Asp Phe Leu Ser Lys Ser Lys Glu Val Gly Gly Leu
                85                  90                  95

Val Ala Glu His Ser Ala Leu Ile Gly Pro Leu Cys Glu Ala Gln Leu
            100                 105                 110

Ser Phe Leu Gln Phe Ala Ser Asn His Ala Lys Pro Ala Thr Pro Asn
        115                 120                 125

Ala Leu Ala Pro Leu Leu Glu Pro Gln Gly Lys Ala Ile Glu Ala Ile
    130                 135                 140

Met Glu Thr Lys Asp Lys Leu Ser Arg Ser Lys Glu Gly Arg Glu Trp
145                 150                 155                 160

Gly Val Cys Phe Asn Val Leu Gly Glu Gly Val Pro Ala Trp Gly Trp
                165                 170                 175

Val Gln Val Glu Pro Thr Pro Ala Pro Tyr Val Gly Glu Met Lys Asn
            180                 185                 190

Ala Ala Gln Phe Trp Ser Asp Arg Val Ile Lys Gln Tyr Lys Glu Thr
        195                 200                 205

Asn Ala Ser Ala Val Ala Trp Ala Lys Ser Phe Ile Ala Leu Ile Ala
    210                 215                 220

Ala Leu Glu Ser Tyr Val Lys Gln Trp His Thr Thr Gly Val Val Trp
225                 230                 235                 240

Asn Pro Lys Gly Ser Pro Ala Pro Pro Ser Met Pro Lys Ala Ser Ala
                245                 250                 255

Ser Ala Pro Ser Pro Pro Pro Pro Pro Pro Ser Gly Ser Ala Pro Ala
            260                 265                 270

Ala Pro Thr Ser Gly Ser Gly Ala Ala Ala Leu Leu Ala Asp Leu Asn
        275                 280                 285

Arg Gly Gly Ala Val Thr Ser Gly Leu Arg Lys Val Asp Ser Ser Gln
    290                 295                 300

Met Thr His Lys Asn Pro Ser Leu Arg Ser Ala Gly Thr Val Ser Asp
305                 310                 315                 320

Asn Ala Lys Lys Gly Pro Pro Leu Lys Pro Lys Pro Gly Ala Lys Pro
                325                 330                 335

Ala Lys Lys Pro Ala Lys Ile Glu Leu Glu Asp Gly Asn Lys Trp Ile
            340                 345                 350

Ile Glu Asn Gln Glu Asp Asn Lys Ser Ile Lys Ile Asp Asn Thr Glu
        355                 360                 365

Leu His His Thr Val His Ile Phe Gly Cys Val Asn Ser Val Val Gln
    370                 375                 380

Ile Ser Gly Lys Ile Asn Ala Val Thr Met Ala Gly Cys Lys Lys Thr
385                 390                 395                 400

Ser Val Val Leu Asp Thr Ala Val Ser Ser Phe Ser Ile Thr Ser Ser
                405                 410                 415

Pro Ser Phe Glu Val Gln Ile Ile Gly Ser Ile Pro Thr Ile Gln Ile
            420                 425                 430

Asp Thr Thr Asp Ser Gly Gln Val Tyr Leu Ser Lys Asp Cys Met Glu
        435                 440                 445

Val Val Glu Ile Val Thr Ser Lys Ser Ser Ser Ile Asn Ile Ser Val
    450                 455                 460
```

```
Pro Thr Gly Glu Asp Gly Asp Phe Val Glu Arg Pro Val Pro Glu Gln
465                 470                 475                 480

Met Lys Ser Arg Ile Ile Asp Gly Lys Leu Val Thr Glu Ile Val Glu
                485                 490                 495

His Ser Gly


<210> SEQ ID NO 28
<211> LENGTH: 515
<212> TYPE: PRT
<213> ORGANISM: Cryptococcus neoformans
<220> FEATURE:
<221> NAME/KEY: PEPTIDE
<222> LOCATION: (1)..(515)
<223> OTHER INFORMATION: an amino acid sequence of Pka1(CNAG_00396.2)
      serotype A H99 strain

<400> SEQUENCE: 28

Met Phe Gln Lys Val Ser Asp Lys Phe His Arg Lys Gln Gln Ser Ser
1               5                   10                  15

Thr Ser Pro Gly Lys Thr Gln Gln Val Pro Asn Ser Pro Ser Ser Val
            20                  25                  30

Leu Ala Lys Ala Asn Ser Gln Ala Gln Gln Ala Tyr Ser Ser Gln Asp
        35                  40                  45

His Ser Pro Met Glu Gly Ile Gln Ser Asp Ser Thr His Ile Gln Gln
    50                  55                  60

Pro Met Ala Thr Gln Lys Ala Pro Ile Val Gly Pro Ser Thr Ser Thr
65                  70                  75                  80

Ser Leu Ser Thr Val Pro Val Gln Asp Gly Thr Leu Pro Leu Thr Pro
                85                  90                  95

Gly Ala Gln Gly Met Leu Ala Gly Thr Thr Asp Gly His Arg Gln Val
            100                 105                 110

Gln Ser Pro Val Ser Arg Ser Ser Ser Ala Gly Glu Asp Lys Met Arg
        115                 120                 125

Glu Lys Ala Arg Asp Ala Gln Glu Gln Ala Ala Gln Ala Gln Ala Asn
    130                 135                 140

Leu His Arg Val Thr Gln Gln Ala Arg Val Ala Ala Ile Asn Ala Ala
145                 150                 155                 160

Ala Thr Gln Ala Ala Leu Glu Thr Ala Thr Gln Leu Pro Ala Thr Ala
                165                 170                 175

Arg Val Pro Thr Ser Gly Thr Gly Ala Glu Pro Gly Gln Ala Arg Arg
            180                 185                 190

Lys Thr Ala Gly Arg Tyr Ala Leu Ser Asp Phe Leu Ile Glu Arg Thr
        195                 200                 205

Leu Gly Thr Gly Ser Phe Gly Arg Val His Leu Val Arg Ser Arg His
    210                 215                 220

Asn Gly Arg Phe Tyr Ala Val Lys Val Leu Asn Lys Glu Lys Val Ile
225                 230                 235                 240

Lys Met Lys Gln Val Glu His Thr Asn Ser Glu Arg Glu Met Leu Val
                245                 250                 255

Arg Val Arg His Pro Phe Leu Val Asn Leu Trp Gly Thr Phe Gln Asp
            260                 265                 270

Val Asn Asn Leu Tyr Met Val Met Asp Phe Val Ala Gly Gly Glu Leu
        275                 280                 285

Phe Ser Leu Leu Arg Lys Ser Gln Arg Phe Pro Asn Ser Val Ala Lys
    290                 295                 300

Phe Tyr Ala Ala Glu Val Ala Leu Ala Leu Asp Tyr Leu His Ser Leu
```

```
305                 310                 315                 320

Asp Ile Ile Tyr Arg Asp Leu Lys Pro Glu Asn Leu Leu Leu Gly Ala
                325                 330                 335

Asp Gly His Val Lys Val Thr Asp Phe Gly Phe Ala Lys Tyr Val Pro
            340                 345                 350

Asp Ile Thr Trp Thr Leu Cys Gly Thr Pro Asp Tyr Leu Ala Pro Glu
        355                 360                 365

Val Val Gln Ser Lys Gly Tyr Asn Lys Ser Val Asp Trp Tyr Ala Leu
    370                 375                 380

Gly Val Leu Ile Phe Glu Met Leu Ala Gly Tyr Pro Pro Phe Phe Thr
385                 390                 395                 400

Glu Asp Gly Asn Pro Met Lys Leu Tyr Glu Lys Ile Ile Ala Gly Lys
                405                 410                 415

Val Arg Tyr Pro Thr Tyr Phe Asp Val Leu Ala Lys Glu Leu Leu Lys
            420                 425                 430

Asn Leu Leu Ile Gly Asp Leu Thr Lys Arg Tyr Gly Asn Leu Arg Ala
        435                 440                 445

Gly Ser Ser Asp Ile Phe Ala His Gly Trp Phe Ala Glu Val Asp Trp
    450                 455                 460

Asp Lys Leu Tyr Arg Arg Glu Ile Pro Ala Pro Tyr Val Pro Lys Ile
465                 470                 475                 480

Asp Gly Glu Gly Asp Ala Ser Gln Phe Asp Arg Tyr Gln Glu Ala Asp
                485                 490                 495

Val Ser Ala Tyr Gly Lys Val Gly Asn Gly Pro Tyr Asp His Phe Phe
            500                 505                 510

Val Glu Phe
        515


<210> SEQ ID NO 29
<211> LENGTH: 83
<212> TYPE: PRT
<213> ORGANISM: Cryptococcus neoformans
<220> FEATURE:
<221> NAME/KEY: PEPTIDE
<222> LOCATION: (1)..(83)
<223> OTHER INFORMATION: an amino acid sequence of Hsp12(CNAG_03143.2)
      serotype A H99 strain

<400> SEQUENCE: 29

Met Ser Asp Ala Gly Arg Gln Ser Phe Thr Asp Lys Ala Gly Ala Ala
1               5                   10                  15

Met Lys Pro Asp Ser Glu Lys Ser Tyr Leu Glu Gln Ala Lys Asp Thr
            20                  25                  30

Ile Gly Gly Lys Ala Asp Ser Ala Ala Ser Thr Gly Gln Pro Gln Ser
        35                  40                  45

Gln Lys Ser Tyr Thr Gln Glu Ile Gly Asp Ala Phe Ser Gly Asn Lys
    50                  55                  60

Asn Asp Asn Gln Glu Ser Leu Thr Asp Lys Ala Lys Asn Ala Phe Gly
65                  70                  75                  80

Ala Asn Gln


<210> SEQ ID NO 30
<211> LENGTH: 70
<212> TYPE: PRT
<213> ORGANISM: Cryptococcus neoformans
<220> FEATURE:
<221> NAME/KEY: PEPTIDE
<222> LOCATION: (1)..(70)
```

-continued

```
<223> OTHER INFORMATION: an amino acid sequence of Hsp122(CNAG_01446.2)
      serotype A H99 strain

<400> SEQUENCE: 30

Met Ser Asp Ala Gly Arg Gln Ser Leu Ala Asp Lys Ala Ser Ser Ser
1               5                   10                  15

Met Lys Pro Asp Ser Glu Lys Ser Tyr Val Glu Gln Ala Ser Asp Phe
            20                  25                  30

Ile Ser Gly Lys Leu Asp Ser Ala Ala Ser Ala Val Gln Pro Gln Gln
        35                  40                  45

Glu Lys Ser Thr Thr Gln Lys Ile Gly Asp Ala Val Ser Gly Asp Asn
    50                  55                  60

Arg Asn Arg Asp Val Ala
65                  70
```